(12) United States Patent
Courty et al.

(10) Patent No.: US 8,497,349 B2
(45) Date of Patent: Jul. 30, 2013

(54) USE OF MULTIVALENT SYNTHETIC LIGANDS OF SURFACE NUCLEOLIN FOR TREATING CANCER OR INFLAMMATION

(75) Inventors: José Courty, Villecresnes (FR); Ara Hovanessian, Bourg la Reine (FR); Jean Paul Briand, Strasbourg (FR); Gilles Guichard, Wolfisheim (FR); Yamina Hamma, Le Kremlin Bicetre (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 1203 days.

(21) Appl. No.: 12/298,511

(22) PCT Filed: Apr. 22, 2007

(86) PCT No.: PCT/FR2007/000730
§ 371 (c)(1),
(2), (4) Date: Oct. 24, 2008

(87) PCT Pub. No.: WO2007/125210
PCT Pub. Date: Nov. 8, 2007

(65) Prior Publication Data
US 2011/0065649 A1 Mar. 17, 2011

(30) Foreign Application Priority Data
Apr. 27, 2006 (FR) ...................................... 06 03813

(51) Int. Cl.
A61K 38/10 (2006.01)
C12N 9/78 (2006.01)
A61P 35/00 (2006.01)
A61K 38/16 (2006.01)
A61K 38/03 (2006.01)

(52) U.S. Cl.
USPC .......... 530/323; 530/326; 530/332; 514/21.4; 514/21.3; 514/19.3; 435/227

(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,340,535 A | 7/1982 | Voisin et al. | |
| 4,366,241 A | 12/1982 | Tom et al. | |
| 4,472,509 A | 9/1984 | Gansow et al. | |
| 5,021,236 A | 6/1991 | Gries et al. | |
| 6,235,716 B1* | 5/2001 | Ben-Sasson | 514/13.3 |
| 7,741,280 B2* | 6/2010 | Guichard et al. | 514/2.4 |
| 2004/0002457 A1 | 1/2004 | Hovanessian et al. | |
| 2004/0186056 A1 | 9/2004 | Ruoslahti et al. | |
| 2005/0026860 A1 | 2/2005 | Lin et al. | |
| 2008/0234464 A1* | 9/2008 | Ikeda et al. | 530/323 |
| 2011/0065649 A1 | 3/2011 | Courty et al. | |

FOREIGN PATENT DOCUMENTS

| | | |
|---|---|---|
| WO | WO 95/29190 | 11/1995 |
| WO | WO 00/61597 | 10/2000 |
| WO | WO 03/102207 | * 12/2003 |
| WO | WO 2005/035579 | 4/2005 |
| WO | WO 2005/035579 A1 | 4/2005 |
| WO | WO 2007/125210 | 4/2007 |
| WO | WO 2007/125210 | 11/2007 |
| WO | WO 2009/141687 | 5/2008 |

OTHER PUBLICATIONS

Nisole, 2002, the Journal of Biological Chemistry, 277, 20877-20886.*
Nisole, 2002, Journal of Biological Chemistry, 277, 20877-20886.*
Fazekas, 2001, Microvascular Research, 62, 440-444.*
Callebaut, 1996, Virology, 218, 181-192.*
Hovanessian et al., Exp. Cell Res. (2000), vol. 261, pp. 312-328.
Zanotti et al., Drugs (2002), vol. 11, pp. 1061-1075.
Nisole, S., et al., "The anti-HIV pentameric Pseudopeptide HB-19 binds the C-terminal end of nucleolon and prevents anchorage of virus particles in the plasma membrane of target cells," J. Biol. Chem., 2002, vol. 277, No. 23, pp. 20877-20886.
Seko, Y., et al., "The role of cytokine mRNA stability in the pathogenesis of autoimmune disease," Autoimmun Rev, 2006, vol. 5, pp. 299-305.
Semenkovich, C. F., et al., "A protein partially expressed on the surface of HepG2 cells that binds lipoproteins specifically is nucleolin," Biochemistry, 1990, vol. 29, pp. 9708-9713.
Shun, C.T., et al., "Glucosyltransferases of viridans streptococci are modulins of interleukin-6 induction in infective endocarditis," Infec. Immun., 2005, vol. 73, No. 6, pp. 3261-3270.
Srivastava, M., et al., "Molecular dissection of nucleolin's role in growth and cell proliferation: new insights," FASEB J., 1999, vol. 13, pp. 1911-1922.
Krust et al., "The anti-HIV pentameric pseudopeptide HB-19 is preferentially taken up in vivo by lymphoid organs where it forms a comples with nucleolin," PNAS, Nov. 20, 2001, vol. 98, No. 24, pp. 14090-14095.
Merrifield, R. B., Solid Phase Peptide Synthesis. I. The Synthesis of a Tetrapeptide, J. Am. Chem. Soc., 85(14), p. 2149-2154, 1963.
Axen et al., Chemical Coupling of Peptides and Proteins to Polysaccharides by Means of Cyanogen Halides, Nature, vol. 214, pp. 1302-1304, 1967.
Goldenberg, D. M. et al., Use of Radiolabeled Antibodies to Carcinoembryonic Antigen for the Detection and Localization of Diverse Cancers by External Photoscanning, The New England Journal of Medicine, vol. 298, p. 1384-1388, 1978.
Goldenberg, D. M. et al., Experimental Radioimmunotherapy of a Zenografted Human Colonic Tumor (GW-39) Producing Carcinoembryonic Antigen, Cancer Research, vol. 41, p. 4353-4360, 1981.

(Continued)

Primary Examiner — Satyanarayana R Gudibane
(74) Attorney, Agent, or Firm — McCarter & English, LLP

(57) ABSTRACT

A method for treating disorders involving deregulation of cell proliferation and/or angiogenesis comprising the administration of an effective amount of a multivalent synthetic compound comprising a support on which at least 3 pseudopeptide units are grafted, said compound being of formula (I).

11 Claims, 24 Drawing Sheets

OTHER PUBLICATIONS

Herlyn, M. et al., Monoclonal Antibody Detection of a Circulating Tumor-Associated Antigen. I. Presence of Antigen in Sera of Patients with Colorectal, Gastric, and Pancreatic Carcinoma, Journal of Clinical Immuology, vol. 2, pp. 135-140, 1982.

Pimm, M. V. et al., Tumour Localization of Monoclonal Antibody Against a Rat Mammary Carcinoma and Suppression of Tumour Growth with Adrianmycin-Antibody Conjugates, Cancer Immunol. Immunother., vol. 12, pp. 125-134, 1982.

Ettinger, D. S. et al., Phase I-II Study of Isotopic Immunogiobulin Therapy for Primary Liver Cancer, Cancer Treatment Reports, vol. 66, p. 289-297, 1982.

Herlyn, D. et al., IgG2a Monoclonal Antibodies Inhibit Human Tumor Growth Through Interactdion with Effector Cells, Proc. Natl. Acad. Sci., USA, vol. 79, pp. 4761-4765, 1982.

Hedin, a. et al., A Monoclonal Antibody-Enzyme Immunoassay for Serum Carcinoembryonic Antigen with Increased Specificity for Carcinomas, Proc. Natl. Acad. Sci., USA, vol. 80, pp. 3470-3474, 1983.

Bast, R. C. et al., A Radioimmunoassay Using a Monoclonal Antibody to Monitor the Course of Epithelial Ovarian Cancer, The New England Journal of Medicine, vol. 309, pp. 883-887, 1983.

Goldenberg, D. M. et al., Radioimmunodetection of Prostatic Cancer, J. A. M. A., vol. 250, pp. 630-635, 1983.

Goldenberg, D. M. et al., Carcinoembryonic Antigen Radioimmunodetection in the Evaluatioin of Colorectal Cancer and in the Detection of Occult Neoplasms, Gastroenterology, vol. 84, pp. 524-532, 1983.

Uhr, J. W. et al., The Use of Immunotoxins for the Treatment of Cancer, Monoclonal Antibodies and Cancer, Academic Press, Inc., pp. 85-98, 1983.

Vitetta, E. S. et al., Immunotoxins: A New Approach to Cancer Therapy, Science, vol. 219, pp. 644-650, 1983.

Schulz, G. et al., Monoclonal Antibody-Directed Effector Cells Selectively Lyse Human Melanoma Cells in vitro and in vivo, Proc. Natl. Acad. Sci., USA, vol. 80, pp. 5407-5411, 1983.

Capone, P. M. et al., Experimental Tumoricidal Effects of Monoclonal Antibody Against Solid Breast Tumors, Proc. Natl. Acad. Sci, USA, vol. 80, pp. 7328-7332, 1983.

Stewart, J. M. et al., Solid Phase Peptide Synthesis, Second Edition, Rockford, Pierce Chemical Company, 91, 1984.

Klug, T. L. et al., Monoclonal Antibody Immunoradiometric Assay for an Antigenic Determinant (CA 125) Associated with Human Epithelial Ovarian Carcinomas, Cancer Research, vol. 44, pp. 1048-1053, 1984, Mar. 1984.

Metzgar, R. S. et al., Detection of a Pancreatic Cancer-Associated Antigen (DU-PAN-2 Antigen) in Serum and Ascites of Patients with Adenocarcinoma, Proc. Natl. Acad. Sci., USA, vol. 81, pp. 5242-5246, 1984.

Papsidero, L. D. et al., Expression of Ductal Carcinoma Antigen in Breast Cancer Sera as Defined Using Monoclonal Antibody F36/22, Cancer. Research, vol. 44, pp. 4653-4657, 1984.

Pekary, A. E. et al., A New Monoclonal-Antibody Two-Site Solid-Phase Immunoradiometric Assay for Human Thyrotropin Evaluated, Clin. Chem., vol. 30/7, pp. 1213-1215, 1984.

Bellet, D. H. et al., Serum α-Fetoprotein Levels in Human Disease: Perspective From A Highly Specific Monoclonal Radioimmunoassay, Proc. Natl. Acad. Sci., USA, vol. 81, pp. 3869-3873, 1984.

Embleton, M. J. et al., Antigenicity and Drug Susceptibility of Human Osteogenic Sarcoma Cells "Escaping" A Cytotoxic Methotrexate-Albumin-Monoclonal Antibody Conjugate, Br. J. Cancer, vol. 49, pp. 559-565, 1984.

Vitetta, E. S. et al., Immunotoxins: A New Approach to Cancer Therapy, Biotechnology and Biol. Frontiers, Ed. P. H. Abelson, p. 73-85, 1984.

Carrasquillo, J. A. et al., Diagnosis of and Therapy for Solid Tumors with Radiolabeled Antibodies and Immune Fragments, Cancer Treatment Reports, vol. 68, pp. 317-328, 1984.

Zalcberg, J. R. et al., Tumor Immunotherapy in the Mouse with the Use of $^{131}$I-Labeled Monoclonal Antibodies, J. Natl. Cancer Inst., vol. 72, pp. 697-704, 1984.

Courtenay-Luck, N. et al., Antiboedy-Guided Irradiation of Malignant Lesions: Three Cases Illustrating a New Method of Treatment, The Lancet, vol. 1, p[. 1441-1443, 1984.

Nepom, G. T. et al., Induction of Immunity to a Human Tumor Marker by in vivo Administration of Anti-Idiotypic Antibodies in Mice, Proc. Natl. Acad. Sci., USA, vol. 81, pp. 2864-2867, 1984.

Kaprowski, H. et al., Human Anti-Idiotype Antibodies in Cancer Patients: Is the Modulation of the Immune Response Beneficial for the Patient, Proc. Natl. Acad. Sci., USA, vol. 81, pp. 216-219, 1984.

Hayes, D. F. et al., Use of a Murine Monoclonal Antibody for Detectioin of Circulating Plasma DF3 Antigen Levels in Breast Cancer Patients, J. Clin. Invest., vol. 75, pp. 1671-1678, 1985.

Killian, C. S. et al., Prognostic Importance of Prostate-Specific Antigen for Monitoring Patients with Stage $B_2$ to $D_1$ Prostate Cancer, Cancer Research, vol. 45, pp. 886-891, 1985.

Epenetos, A. A. et al., $^{123}$I Radioiodinated Antibody Imaging of Occult Ovarian Cancder, Cancer, vol. 55, p. 984-987, 1985.

Chiou, R. et al., Localization of Human Renal Cell Carcinoma Xenografts with a Tumor-Preferential Monoclonal Antibody, Cancer Research, vol. 45, p. 6140-6146, 1985.

Deguchi, T. et al., Effects of Lymphokines, Antibodies and Immunotherapeutic Agents on Tumors, Federal Proceedings, vol. 44, p. 1684, 1985.

Jones, D. H. et al., Therapeutic Application of a Radiolabelled Monoclonal Antibody in Nude Mice Xenografted with Human Neuróblastoma: Tumoricidal Effects and Distribution Studies, Int. J. Cancer, vol. 35, pp. 715-720, 1985.

Lange, P. H. et al., Monoclonal Antibodies in Human Renal Cell Carcinoma and Their Use in Radioimmune Localization and Therapy of Tumor Xenografts, Surgery, vol. 98, pp. 143-150, 1985.

Liu, M.A. et al., Heteroantibody Duplexes Target Cells for Lysis by Cytotocis T Lymphocytes, Proc. Natl. Acad. Sci., USA, vol. 82, pp. 8648-8652, 1985.

Sears, H. F. et al., Phase II Clinical Trial of a Murine Monoclonal Antibody Cytotoxic for Gastrointestinal Adenocarcinoma, Cancer Ressearch, vol. 45, pp. 5910-5913, 1985.

Houghton, A. N. et al., Mouse Monoclonal IgG3 Antibody Detecting $G_{D3}$ Antibody Detecting $G_{D3}$ Ganglioside: A Phase I Trial in Patients with Malignant Melanoma, Proc. Natl. Acad. Sci., USA, vol. 82, pp. 1242-1246, 1985.

Remington's Pharmaceutical Sciences, $17_{th}$ Edition, Title page and Prefaces, Mack Publishing Co., A. R. Gennaro edit, 1985.

Killian, C. S. et al., Relative Reliability of Five Serially Measured Markers for Prognosis of Progression in Prostate Cancer, J. Natl. Cancer Inst., vol. 76, pp. 179-185, 1986.

Siccardi, A. G. et al., Multicenter Study of Immunoscintigraphy with Radiolabeled Monoclonal Antibodies in Patients with Melanoma, Cancer Research, vol. 46, pp. 4817-4822, 1986.

Philben, V. J. et al., The Effect of Tumor CEA Content and Tumor Size on Tissue Uptake of Indium 111-Labeled Anti-CEA Monoclonal Antibody, Cancer, vol. 57, pp. 571-576, 1986.

Hwang, K. M. et al., Dynamic Interaction of $^{111}$Indium-Labeled Monoclonal Antibodies With Surface Antigens of Solid Tumors Visualized In Vivo by External Scintigraphy, J. Natl. Cancer Inst., vol. 76, p. 849-855, 1986.

Deguchi, T. et al., Effect of Methotrexate-Monoclonal Anti-Prostatic Acid Phosphatase Antibody Conjugate on Human Prostate Tumor, Cancer Research, vol. 46, pp. 3751-3755, 1986.

Kaltovich, F. A. et al., Radioimmunotherapy (RAIT) of Human Colonic Cancer Xenocrafts With Anti-Carcinoembryonic Antigen (CEA) Antibody, J. Nucl. Med., vol. 27, p. 897, 1986.

Perez, P. et al., Specific Targeting of Human Peripheral Blood T Cells by Heteroaggregates Containing Anti-T3 Crosslinked to Anti-Target Cell Antibodies, J. Exper. Med., vol. 163, pp. 166-178, 1986.

Feuerstein, N. et al., Identificaiotn of Numatrin, the Nuclear Matrix Protein Associated with Induction of Mitogenesis, as the Nucleolar Protein B23. Implication for the Role of the Nucleolus in Early Transduction of Mitogenic Signals, J. Biol. Chem., 263(22), p. 10608-10612, 1988.

Atherton, E. et al., Solid Phase Peptide Synthesis: A Practical Approach, Title page and Contents, Oxford, England, IRL Press, 1989.

M. Cushman, et al., Development of Methodology for the Synthesis of Stereochemically Pure PheΨ[CH2N]Pro Linkages in HIV Protease Inhibitors, J Org. Chem. 56, pp. 4161-4167, 1991.

Okawa et al., Journal of Immunological Methods, vol. 149, pp. 127, 1992.

Rot, A., Neutrophil Attractant/Activation Protein-1 (Intrleukin-8) Induces in vitro Neutrophil Migration by Haptotactic Mechanism, Eur. J. Immunol., vol. 23, pp. 303-306, 1993.

Gregoriadis (Editor), Liposome Technology, $2^{nd}$ Edition, vols. I-III, CRC Press, Boca Raton, Florida, Ann Arbor, Michigan, London, United Kingdom, Tokyo, Japan, 1993.

Carpino, L. A., 1-Hydroxy-7-azabenzotriazole. An efficient Peptide Coupling Additive, J. Am. Chem. Soc., 115(10), pp. 4397-4398, 1993.

Kreuter et al., Passage of Peptides Through the Blood-Brain Barrier with Colloidal Polymer Particles (Nanoparticles), Brain Research, vol. 674, pp. 171-174, 1995.

Pardridge et al., Vector-Mediated Delivery of a Polyamide ("Peptide") Nucleic Acid Analogue Through the Blood-Brain Barrier in vivo, NPNAS USA, vol. 92, pp. 5592-5596, 1995.

Boado, Antisense Drug Delivery Through the Blood-Braiin Barrier, Advanced Drug Delivery Reviews, vol. 15, pp. 73-107, 1995.

Lasic et al., The "Stealth" Liposome: A Prototypical Biomaterial, Chemical Reviews, vol. 95, pp. 2601-2627, 1995.

Ishiwata et al., Physical-Chemistry Characteristics and Biodistribution of Poly(ethylene glycol)-Coated Liposomes Using Poly(oxyethylene) Cholesteryl Ether, Chem. Pharm. Bull, vol. 43, pp. 1005-1011, 1995.

Majno, G. et al., Apoptosis, Oncosis, and Decrosis. An Overview of Cell Death, American Journal Pathology, 146(1), pp. 3-15, 1995.

Engleton et al., Bioavailability and Transport of Peptides and Peptide Drugs into the Brain, Peptides, vol. 9, pp. 1431-1439, 1997.

O'Reilly, M. S. et al., Endostatin: An Endogenous Inhibitor of Angiogenesis and Tumor Growth, Cell, 88(2), pp. 277-285, 1997.

Larrucea, S. et al., Cellular Adhesion Mediated by Factor J, A Complement Inhibitor. Evidence for Nucleolin Involvement, J. Biol. Chem., 273(48), pp. 31718-31725, 1998.

Boado et al., Drug Delivery of Antisense Molecules to the Brain for Treatment of Alzheimer's Disease and Cerebral AIDS, Journal of Pharmaceutical Sciences, vol. 87, pp. 1308-1315, 1998.

Aldrian-Herrada et al., A Peptide Nucleic Acid (PNA) is more Rapidly Internalized in Cultured Neurons When Coupled to a Retro-Inverso Delivery Peptide. The Antisense Activity Depresses the Target mRNA and Protein in Magnocellular Oxytocin Neurons, Nucleic Acids Res., vol. 26, pp. 4910-4916, 1998.

Jolliet-Riant, et al., Drug Transfer Across the Blood-Brain Barrier and Improvement of Brain Delivery, Fundam. Clin. Pharmacol., vol. 13, pp. 16-26, 1999.

Emerich, D. F. et al., Cell Transplant, vol. 8, pp. 47-59, 1999.

Schroeder, et al., Diffusion Enhancement of Drugs by Loaded Nanoparticles in Vitro, Prog. Neuropsychopharmacol. Biol. Psychiatry, vol. 23, pp. 941-949, 1999.

Dumler, I. et al., Urokinase-Induced Mitogenesis is Mediated by Casein Kinase 2 and Nucleolin, Curr. Bio., 9(24), pp. 1468-1476, 1999.

Emerich, D. F. et al., Bicompatibility of Poly (D-Lactide-co-Glycolide) Microspheres Implanted Into the Brain, Cell Transplant, vol. 8, pp. 47-58, 1999.

Tyler et al., Specific Gene Blockade Shows that Peptide Nucleic Acids Readily Enter Neuronal Cells in vivo, FEBS Letters, vol. 421, pp. 280-284, 1999.

Tyler et al., Peptide Nucleic Acids Targeted to the Neurotensin Receptor and Administered I.P. Cross the Blood-Braiin Barrier and Specifically Reduce Gene Expression, PNAS USA, vol. 96, pp. 7053-7058, 1999.

Dhanabal, M. et al., Endostatin Induces Endothelial Cell Apoptosis, J. Biol. Chem., 274(17), pp. 11721-11726, 1999.

Xu et al., Inhibition of DNA Replication and Induction of S Phase Cell Cycle Arrest by G-Rich Oligonucleotides, J. Biol. Chem., vol. 276, pp. 43221-43230, 2001.

Harms, G. et al., Identification of Nucleolin as a New L-Selectin Ligand, Biochem. J., 360(Pt 3), pp. 531-538, 2001.

Sengupta, T. K. et al., Identification of nucleolin as an AU-Rich Element Binding Protein Involved in bcl-2 mRNA Stabilization, J. Biol. Chem., 279(12), pp. 10855-10863, 2004.

Otake, Y. et al., Retinoid-Induced Apoptosis in HL-60 Cells is Associated with Nucleolin Down-Regulation and Destabilization of Bcl-2 mRNA, Mol. Pharmacol., 67(1), pp. 319-26, 2005.

Takagi, M. et al., Regulation of p53 Translation and Induction After DNA Damage by Ribosomal Protein L26 and Nucleolin, Cell, 123(1), pp. 49-63, 2005.

Chan, H. J. et al., Nucleophosmin/B23-Binding Peptide Inhibits Tumor Growth and Up-Regulates Transcriptional Activity of p53, Biochem. Biophys. Res. Commun., 333(2), pp. 396-403, 2005.

Alete et al., Febs J., vol. 273, pp. 4668-4681, 2006.

Tate, A. et al., Met-Independent Hepatocyte Growth Factor-mediated regulation of cell adhesion of human prostate cancer cells, BMC Cancer, vol. 6, p. 197, 2006.

Turck, N. et al., Effect of Laminin-1 on Intestinal Cell Differentiation Involves Inhibition of Nuclear Nucleolin, J. Cell. Physio., 2006(2), pp. 545-55, 2006.

Grinstein, E. et al., Cell Cycle-Controlled Interaction of Nucleolin with the Retinoblastoma Protein and Cancerous Cell Transformation, J. Biol. Chem., 281(31), pp. 22223-22235, 2006.

Blondet, B. et al., Exogeneous Pleiotrophin Applied to Lesioned Nerve Impairs Muscle Reinnervation, Neurochem. Res., 31(7), pp. 907-913, 2006.

Otake, Y. et al., Overexpression of Nucleolin in Chronic Lymphocytic Leukemia Cells Induces Stabilization of bcl2 mRNA, Blood, 109(7), pp. 3069-3075, 2007.

Ugrinova, I. et al., Inactivation of Nucleolin Leads to Nucleolar Disruption, Cell Cycle Arrest and Defects in Centrosome Duplication, BMC Molecular Biology, 8(1), pp. 1-16, 2007.

Shi, H. et al., Nucleolin is a Receptor that <ediates Antiangiogenic and Antitumor Activity of Endostatin, Blook, 110(8), pp. 1899-1906, 2007.

Di Segni, A. et al., Identification of Nucleolin as New ErbB Receptor Interacting Protein, PLoS One, 3(6), e2310, pp. 1-9, 2008.

Stepanova, V. et al., Nuclear Translocation of Urokinase-Type Plasminogen Activator, Blood, 112(1), pp. 100-110, 2008.

Reyes-Reyes, E. M. et al., Cell-Surface Nucleolin is a Signal Transducing P-Selectin Binding Protein for Human Colon Carcinoma Cells, Exp. Cell Res., 314(11-12), pp. 2212-2223, 2008.

Destouches, D. et al., Suppression of Tumor Growth and Angiogenesis by a Specific Antagonist of the Cell-Surface Expressed Nucleolin, PLoS One, 3(6), e2518, pp. 1-12, 2008.

Soundararajan, S. et al., The Nucleolin Targeting Aptamer AS1411 Destabilizes BcI-2 Messenger RNA in Human Breast Cancer Cells, Cancer Res., 68(7), pp. 2358-2365, 2008.

Qi, W. et al., NSC348884, A Nucleophosmin Inhibitor Disrupts Oligomer Formation and Induces Apoptosis in Human Cancer Cells, Oncogene, 27(30), pp. 4210-4220, 2008.

Pierce Chemical Company, Catalog No. 22980, 2002.

Bates, P. J. et al., Discovery and Development of the G-Rich Oligonucleotide AS1411 as A Novel Treatment for Cancer, Experimental and Molecular Pathology, 86(3), pp. 151-164, 2009.

Drecoll, E. et al., Treatment of Peritoneal Carcinomatosis by Targeted Delivery of the Radio-L6beled Tumor Homing Peptide bi-DTPA-[F3]2 into the Nucleus of Tumor Cells, PloS One, 4(5), e5715, pp. 1-9, 2009.

Fogal, V. et al., Cell Surface Nucleolin Antagonist Causes Endothelial Cell Apoptosis and Normalization of Tumor Vasculature, Angiogenesis, 12(1), pp. 91-100, 2009.

Page, N. et al., The Spliceosomal Phosphopeptide P140 Controls the Lupus Disease by Interacting with the HSC70 Protein and via a Mechanism Mediated by Hammadelta T Cells, PLos One, 4(4), e5273, pp. 1-13, 2009.

Ling, Y. et al., Endostar Induces Apoptotic Effects in HUVECs Through Activation of Caspase-3 and Decrease of BcI-2, Anticancer Res., 29(1), pp. 411-417, 2009.

Inder, K. L. et al., Nucleophosmin and Nucleolin regulate K-Ras Plasma Membrane Interactions and MAPK Signal Transduction, J. Biol. Chem., 284(41), pp. 28410-28933, 2009.

PCT International Search Report for Wo 2007/125210 dated Jun. 30, 2008.

PCT International Search Report for WO 2009/141687 dated Sep. 2, 2009.

Rot, Neutrophil Attractant/Activation Protein-1 (Interleukin-8) Induces in vitro Neutrophil Migration by Haptotactic Mechanism, Eur. J. Immunol., 1993, vol. 23, pp. 303-306.

Bucklin, et al., An Interleukin-6-Induced Acute-Phase Response Does Not Confer Protection Against Lipopolysaccharide Lethality, Infection and Immunity, Aug. 1993, pp. 31-84-3189.

Callebaut, et al., Pseudopeptide TASP Inhibitors of HIV Entry Bind Specifically to a 95-kDa Cell Surface Protein, The Journal of Biological Chemistry, vol. 272, No. 11, Issue of Mar. 14, 1997, pp. 7159-7166.

Callebaut, et al., Identification of V3 Loop-Binding Proteins as Potential Receptors Implicated in the Binding of HIV Particles to CD4+ Cells, The Journal of Biological Chemistry, vol. 273, No. 34, Issue of Aug. 21, 1998, pp. 21988-21997.

Karima, et al., The Molecular Pathogenesis of Endotoxic Shock and Organ Failure, Molecular Medicine Today, Mar. 1999, pp. 123-132.

Ginisty, et al., Structure and Functions of Nucleolin, Journal of Cell Structure, 112, pp. 761-772, 1999.

Bates, et al., Antiproliferative Activity of G-Rich Oligonucleotides Correlates with Protein Binding, The Journal of Biological Chemistry, vol. 274, No. 37, Issue of Sep. 10, 1999, pp. 26369-26377.

Nisole, et al., The Anti-HIV Pseudopeptide HB-19 Forms a Complex with the Cell-Surface-Expressed Nucleolin Independent of Heparan Sulfate Proteoglycans, The Journal of Biological Chemistry, vol. 274, No. 39, Issue of Sep. 24, 1999, pp. 27875-27884.

Nisole, et al., The HB-19 Pseudopeptide 5[KΨ(CH$_2$ N)PR]-TASP Inhibits Attachment of T Lymphocyte- and Macrophage-Tropic HIV to Permissive Cells, Aids Research and Human Retroviruses, vol. 16, No. 3, 2000, pp. 237-249.

Kevil, et al., Essential Role of ICAM-1 in Mediating Monocyte Adhesion to Aortic Endothelial Cells, Am. J. Physiol. Cell Physiol., 281: C1442-C1447, 2001.

Said, The Anti-HIV Cytokine Midkine Binds the Cell Surface-Expressed Nucleolin as a Low Affinity Receptor, The Journal of Biological Chemistry, vol. 277, No. 40, Issue of Oct. 4, 2002, pp. 37492-37502.

Elass, et al., Lactoferrin Inhibits the Lipopolysaccharide-Induced Expression and Proteoglycan-Binding Ability of Interleukin-8 in Human Endothelial Cells, Infection and Immunity, Apr. 2002, pp. 1860-1866.

Kabbinavar, et al., Phase II, Randomized Trial Comparing Bevaelzumab Plus Fluorouracil (FU)/Leucovorin (LV) With FU/LV Alone in Patients with Metastatic Colorectal Cancer, Journal of Clinical Oncology, vol. 21, No. 1, Jan. 1, 2003, pp. 60-65.

Hurwitz, New Agents in Colon Cancer, Advances in Oncology, Clinical Advances in Hematology & Oncology, vol. 1, Issue 7, Jul. 2003, pp. 404-405.

Legrand, Surface Nucleolin Participates in Both the Binding and Endocytosis of Lactoferring in Target Cells, Eur. J. Biochem., 271, pp. 303-317, 2004.

Christian, et al., Nucleolin Expressed at the Cell Surface is a Marker of Endothelial Cells in Angiogenic Blood Vessels, The Journal of Cell Biology, vol. 163, No. 4, Nov. 24, 2005, pp. 871-878.

Kannan, et al., Animal Models of Rheumatoid Arthritis and Their Relevance to Human Disease, Pathophysiology, 12, 2005, pp. 167-181.

Siad, et al., Pleiotrophin Inhibits HIV Infection by Binding the Cell Surface-Expressed Nucleolin, FEBS Journal, 272, 2005, pp. 4646-4659.

Fournel, et al., $C_3$-Symmetric Peptide Scaffolds are Functional Mimetics of Trimeric CD4OL, Nature Chemical Biology, vol. 1, No. 7, Dec. 2005, pp. 377-382.

Huang, et al., The Angiogenic Function of Nucleolin is Mediated by Vascular Endothelial Growth Factor and Nonmuscle Myosin, Blood, vol. 107, No. 9, May 1, 2006, pp. 3564-3571.`

Peifer, et al, New Approaches to the Treatment of Inflammatory Disorders Small Molecule Inhibitors of p38 MAP Kinase, Current Topices in Medicinal Chemistry, 6, 113-149, 2006.

Hruby et al. , Conformational and Topographical Considerations in Designing Agonist Peptidomimetics from Peptide Leads, *Current Medicinal Chemistry*, 2000, 7, pp. 945-970.

Hovanessian, et al., Surface Expressed Nucleolin is Constantly Induced in Tumor Cells to Mediate Calcium-Dependent Ligand Internalization, PLoS ONE Dec. 2010, 5(12) : pp. 1-13.

El Khoury et al., Targeting Surface Nucleolin with a Multivalent Pseudopeptide Delays Development of Spontaneous Melanoma in RET Transgenic Mice, *BMC Cancer* 2010, 10:325, pp. 1-12.

Krust et al., Suppression of Tumorigenicity of Rhabdoid Tumor Derived G401 Cells by the Multivalent HB-19 Pseudopeptide that Targetrs Surface Nucleolin, Biochimie. Mar. 2011;93(3):426-433.

Krust et al., Targeting Surface Nucleolin with Multivalent HB-19 and Related Nucant Pseudopeptides Results in Distinct Inhibitory Mechanisms Depending on the Malignant Tumor Cell Type, BMC Cancer 2011,'11:333, pp. 1-22.

Destouches et al., A Simple Approach to Cancer Therapy Afforded by Multivalent Pseudopeptides that Target Cell-Surface Nucleoproteins, Cancer Res 2011;71:3296-3305.

\* cited by examiner

A

HB-19

B

Nucant 01

C

```
         Lys Ψ[CH₂-N]-Pro-Arg    Lys Ψ[CH₂-N]-Pro-Arg    Lys Ψ[CH₂-N]-Pro-Arg    Lys Ψ[CH₂-N]-Pro-Arg    Lys Ψ[CH₂-N]-Pro-Arg
              |                       |                       |                       |                       |
Ac-Aib-Lys-Aib-Gly-Aib-Lys-Aib-Gly-Aib-Lys-Aib-Gly-Aib-Lys-Aib-Gly-Aib-Lys-Aib-Gly-CONH₂
```

Nucant 2

D

```
         Lys Ψ[CH₂-N]-Pro-Arg    Lys Ψ[CH₂-N]-Pro-Arg    Lys Ψ[CH₂-N]-Pro-Arg    Lys Ψ[CH₂-N]-Pro-Arg    Lys Ψ[CH₂-N]-Pro-Arg
              |                       |                       |                       |                       |
Ac-Lys-Aib-Gly-Lys-Aib-Gly-Lys-Aib-Gly-Lys-Aib-Gly-Lys-Aib-Gly-CONH₂
```

Nucant 3

Ac-Lys-Aib-Gly-Lys-Aib-Gly-Lys-Aib-Gly-Lys-Aib-Gly-Lys-Aib-Gly-Lys-Aib-Gly-CONH$_2$ with LysΨ[CH$_2$-N]-Pro-Arg branches on each Lys

Nucant 6

F

Ac-Lys-Ala-Lys-Pro-Gly-Lys-Ala-Lys-Pro-Gly-Lys-Ala-Lys-Pro-Gly-CONH$_2$ with LysΨ[CH$_2$-N]-Pro-Arg branches on each Lys

Nucant 7

SEQUENCE LISTING

<160> NUMBER OF SEQ ID NOS: 21

<210> SEQ ID NO 1
<211> LENGTH: 10
<212> TYPE: PRT

-continued

<213> ORGANISM: Artificial Sequence
<220> FEATURE:
<223> OTHER INFORMATION: Synthetic peptide

<400> SEQUENCE: 1

Lys Lys Lys Gly Pro Lys Glu Lys Gly Cys
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Lys Lys Lys Lys Gly Cys
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide

<400> SEQUENCE: 3

Lys Lys Lys Lys Gly Pro Lys Lys Lys Gly Ala
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: Xaa represents the (2S)-2-aminohexanamide

<400> SEQUENCE: 4

Lys Lys Lys Gly Pro Lys Glu Lys Xaa
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Lysinyl proline
<220> FEATURE:
<221> NAME/KEY: BINDING
<222> LOCATION: (3)..(3)
<223> OTHER INFORMATION: Lys is modified with N6-Arg-Pro-Lysinyl
<220> FEATURE:
<221> NAME/KEY: BINDING
<222> LOCATION: (5)..(5)
<223> OTHER INFORMATION: Lys is modified with N6-Arg-Pro-Lysinyl
<220> FEATURE:
<221> NAME/KEY: BINDING
<222> LOCATION: (8)..(8)
<223> OTHER INFORMATION: Lys is modified with N6-Arg-Pro-Lysinyl
<220> FEATURE:
<221> NAME/KEY: BINDING
<222> LOCATION: (10)..(10)
<223> OTHER INFORMATION: Lys is modified with N6-Arg-Pro-Lysinyl
<220> FEATURE:

```
<221> NAME/KEY: MOD_RES
<222> LOCATION: (11)..(11)
<223> OTHER INFORMATION: Xaa represents the (2S)-2-aminohexanamide

<400> SEQUENCE: 5

Pro Arg Lys Lys Lys Gly Pro Lys Glu Lys Xaa
1               5                   10

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Aib (2-aminoisobutyric acid)
<220> FEATURE:
<221> NAME/KEY: MOD_RES
<222> LOCATION: (3)..(3)
<223> OTHER INFORMATION: Xaa is Aib (2-aminoisobutyric acid)

<400> SEQUENCE: 6

Xaa Lys Xaa Gly
1

<210> SEQ ID NO 7
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is Aib (2-aminoisobutyric acid)

<400> SEQUENCE: 7

Lys Xaa Gly
1

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Aib (2-aminoisobutyric acid)
<220> FEATURE:
<221> NAME/KEY: MOD_RES
<222> LOCATION: (3)..(3)
<223> OTHER INFORMATION: Xaa is Aib (2-aminoisobutyric acid)
<220> FEATURE:
<221> NAME/KEY: MOD_RES
<222> LOCATION: (5)..(5)
<223> OTHER INFORMATION: Xaa is Aib (2-aminoisobutyric acid)
<220> FEATURE:
<221> NAME/KEY: MOD_RES
<222> LOCATION: (7)..(7)
<223> OTHER INFORMATION: Xaa is Aib (2-aminoisobutyric acid)
<220> FEATURE:
<221> NAME/KEY: MOD_RES
<222> LOCATION: (9)..(9)
<223> OTHER INFORMATION: Xaa is Aib (2-aminoisobutyric acid)
<220> FEATURE:
<221> NAME/KEY: MOD_RES
<222> LOCATION: (11)..(11)
<223> OTHER INFORMATION: Xaa is Aib (2-aminoisobutyric acid)
<220> FEATURE:
<221> NAME/KEY: MOD_RES
```

```
<222> LOCATION: (13)..(13)
<223> OTHER INFORMATION: Xaa is Aib (2-aminoisobutyric acid)
<220> FEATURE:
<221> NAME/KEY: MOD_RES
<222> LOCATION: (15)..(15)
<223> OTHER INFORMATION: Xaa is Aib (2-aminoisobutyric acid)
<220> FEATURE:
<221> NAME/KEY: MOD_RES
<222> LOCATION: (17)..(17)
<223> OTHER INFORMATION: Xaa is Aib (2-aminoisobutyric acid)
<220> FEATURE:
<221> NAME/KEY: MOD_RES
<222> LOCATION: (19)..(19)
<223> OTHER INFORMATION: Xaa is Aib (2-aminoisobutyric acid)

<400> SEQUENCE: 8

Xaa Lys Xaa Gly Xaa Lys Xaa Gly Xaa Lys Xaa Gly Xaa Lys Xaa Gly
1               5                   10                  15

Xaa Lys Xaa Gly
            20

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is Aib (2-aminoisobutyric acid)
<220> FEATURE:
<221> NAME/KEY: MOD_RES
<222> LOCATION: (5)..(5)
<223> OTHER INFORMATION: Xaa is Aib (2-aminoisobutyric acid)
<220> FEATURE:
<221> NAME/KEY: MOD_RES
<222> LOCATION: (8)..(8)
<223> OTHER INFORMATION: Xaa is Aib (2-aminoisobutyric acid)
<220> FEATURE:
<221> NAME/KEY: MOD_RES
<222> LOCATION: (11)..(11)
<223> OTHER INFORMATION: Xaa is Aib (2-aminoisobutyric acid)
<220> FEATURE:
<221> NAME/KEY: MOD_RES
<222> LOCATION: (14)..(14)
<223> OTHER INFORMATION: Xaa is Aib (2-aminoisobutyric acid)

<400> SEQUENCE: 9

Lys Xaa Gly Lys Xaa Gly Lys Xaa Gly Lys Xaa Gly Lys Xaa Gly
1               5                   10                  15

<210> SEQ ID NO 10
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Aib (2-aminoisobutyric acid)
<220> FEATURE:
<221> NAME/KEY: BINDING
<222> LOCATION: (2)..(2)
<223> OTHER INFORMATION: Lys modified with N6-Arg-Pro-Lysinyl
<220> FEATURE:
<221> NAME/KEY: MOD_RES
<222> LOCATION: (3)..(3)
<223> OTHER INFORMATION: Xaa is Aib (2-aminoisobutyric acid)
<220> FEATURE:
<221> NAME/KEY: MOD_RES
<222> LOCATION: (5)..(5)
<223> OTHER INFORMATION: Xaa is Aib (2-aminoisobutyric acid)
<220> FEATURE:
```

```
<221> NAME/KEY: BINDING
<222> LOCATION: (6)..(6)
<223> OTHER INFORMATION: Lys modified with N6-Arg-Pro-Lysinyl
<220> FEATURE:
<221> NAME/KEY: MOD_RES
<222> LOCATION: (7)..(7)
<223> OTHER INFORMATION: Xaa is Aib (2-aminoisobutyric acid)
<220> FEATURE:
<221> NAME/KEY: MOD_RES
<222> LOCATION: (9)..(9)
<223> OTHER INFORMATION: Xaa is Aib (2-aminoisobutyric acid)
<220> FEATURE:
<221> NAME/KEY: BINDING
<222> LOCATION: (10)..(10)
<223> OTHER INFORMATION: Lys modified with N6-Arg-Pro-Lysinyl
<220> FEATURE:
<221> NAME/KEY: MOD_RES
<222> LOCATION: (11)..(11)
<223> OTHER INFORMATION: Xaa is Aib (2-aminoisobutyric acid)
<220> FEATURE:
<221> NAME/KEY: MOD_RES
<222> LOCATION: (13)..(13)
<223> OTHER INFORMATION: Xaa is Aib (2-aminoisobutyric acid)
<220> FEATURE:
<221> NAME/KEY: BINDING
<222> LOCATION: (14)..(14)
<223> OTHER INFORMATION: Lys modified with N6-Arg-Pro-Lysinyl
<220> FEATURE:
<221> NAME/KEY: MOD_RES
<222> LOCATION: (15)..(15)
<223> OTHER INFORMATION: Xaa is Aib (2-aminoisobutyric acid)
<220> FEATURE:
<221> NAME/KEY: MOD_RES
<222> LOCATION: (17)..(17)
<223> OTHER INFORMATION: Xaa is Aib (2-aminoisobutyric acid)
<220> FEATURE:
<221> NAME/KEY: BINDING
<222> LOCATION: (18)..(18)
<223> OTHER INFORMATION: Lys modified with N6-Arg-Pro-Lysinyl
<220> FEATURE:
<221> NAME/KEY: MOD_RES
<222> LOCATION: (19)..(19)
<223> OTHER INFORMATION: Xaa is Aib (2-aminoisobutyric acid)

<400> SEQUENCE: 10

Xaa Lys Xaa Gly Xaa Lys Xaa Gly Xaa Lys Xaa Gly Xaa Lys Xaa Gly
1               5                   10                  15

Xaa Lys Xaa Gly
            20

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Lys modified with N6-Arg-Pro-Lysinyl
<220> FEATURE:
<221> NAME/KEY: MOD_RES
<222> LOCATION: (2)..(2)
<223> OTHER INFORMATION: Xaa is Aib (2-aminoisobutyric acid)
<220> FEATURE:
<221> NAME/KEY: BINDING
<222> LOCATION: (4)..(4)
<223> OTHER INFORMATION: Lys modified with N6-Arg-Pro-Lysinyl
<220> FEATURE:
<221> NAME/KEY: MOD_RES
<222> LOCATION: (5)..(5)
<223> OTHER INFORMATION: Xaa is Aib (2-aminoisobutyric acid)
<220> FEATURE:
<221> NAME/KEY: BINDING
<222> LOCATION: (7)..(7)
<223> OTHER INFORMATION: Lys modified with N6-Arg-Pro-Lysinyl
<220> FEATURE:
```

```
<221> NAME/KEY: MOD_RES
<222> LOCATION: (8)..(8)
<223> OTHER INFORMATION: Xaa is Aib (2-aminoisobutyric acid)
<220> FEATURE:
<221> NAME/KEY: BINDING
<222> LOCATION: (10)..(10)
<223> OTHER INFORMATION: Lys modified with N6-Arg-Pro-Lysinyl
<220> FEATURE:
<221> NAME/KEY: MOD_RES
<222> LOCATION: (11)..(11)
<223> OTHER INFORMATION: Xaa is Aib (2-aminoisobutyric acid)
<220> FEATURE:
<221> NAME/KEY: BINDING
<222> LOCATION: (13)..(13)
<223> OTHER INFORMATION: Lys modified with N6-Arg-Pro-Lysinyl
<220> FEATURE:
<221> NAME/KEY: MOD_RES
<222> LOCATION: (14)..(14)
<223> OTHER INFORMATION: Xaa is Aib (2-aminoisobutyric acid)

<400> SEQUENCE: 11

Lys Xaa Gly Lys Xaa Gly Lys Xaa Gly Lys Xaa Gly Lys Xaa Gly
1               5                   10                  15

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide

<400> SEQUENCE: 12

Lys Ala Lys Pro Gly
1               5

<210> SEQ ID NO 13
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl lysine
<220> FEATURE:
<221> NAME/KEY: MOD_RES
<222> LOCATION: (15)..(15)
<223> OTHER INFORMATION: Amide glycine

<400> SEQUENCE: 13

Lys Ala Lys Pro Gly Lys Ala Lys Pro Gly Lys Ala Lys Pro Gly
1               5                   10                  15

<210> SEQ ID NO 14
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Aib (2-aminoisobutyric acid) or Acetyl
      lysine
<220> FEATURE:
<221> NAME/KEY: MOD_RES
<222> LOCATION: (2)..(2)
<223> OTHER INFORMATION: Acetyl lysine
<220> FEATURE:
<221> NAME/KEY: MOD_RES
<222> LOCATION: (3)..(3)
<223> OTHER INFORMATION: Xaa is Aib (2-aminoisobutyric acid)
<220> FEATURE:
```

```
<221> NAME/KEY: MOD_RES
<222> LOCATION: (5)..(5)
<223> OTHER INFORMATION: Xaa is Aib (2-aminoisobutyric acid)
<220> FEATURE:
<221> NAME/KEY: MOD_RES
<222> LOCATION: (7)..(7)
<223> OTHER INFORMATION: Xaa is Aib (2-aminoisobutyric acid)
<220> FEATURE:
<221> NAME/KEY: MOD_RES
<222> LOCATION: (9)..(9)
<223> OTHER INFORMATION: Xaa is Aib (2-aminoisobutyric acid)
<220> FEATURE:
<221> NAME/KEY: MOD_RES
<222> LOCATION: (11)..(11)
<223> OTHER INFORMATION: Xaa is Aib (2-aminoisobutyric acid)
<220> FEATURE:
<221> NAME/KEY: MOD_RES
<222> LOCATION: (13)..(13)
<223> OTHER INFORMATION: Xaa is Aib (2-aminoisobutyric acid)
<220> FEATURE:
<221> NAME/KEY: MOD_RES
<222> LOCATION: (15)..(15)
<223> OTHER INFORMATION: Xaa is Aib (2-aminoisobutyric acid)
<220> FEATURE:
<221> NAME/KEY: MOD_RES
<222> LOCATION: (17)..(17)
<223> OTHER INFORMATION: Xaa is Aib (2-aminoisobutyric acid)
<220> FEATURE:
<221> NAME/KEY: MISC_FEATURE
<222> LOCATION: (19)..(19)
<223> OTHER INFORMATION: Xaa is any naturally occurring amino acid
<220> FEATURE:
<221> NAME/KEY: MOD_RES
<222> LOCATION: (21)..(21)
<223> OTHER INFORMATION: Xaa is Aib (2-aminoisobutyric acid)
<220> FEATURE:
<221> NAME/KEY: MOD_RES
<222> LOCATION: (23)..(23)
<223> OTHER INFORMATION: Xaa is Aib (2-aminoisobutyric acid)
<220> FEATURE:
<221> NAME/KEY: MOD_RES
<222> LOCATION: (24)..(24)
<223> OTHER INFORMATION: Amide glycine

<400> SEQUENCE: 14

Xaa Lys Xaa Gly Xaa Lys Xaa Gly Xaa Lys Xaa Gly Xaa Lys Xaa Gly
1               5                   10                  15

Xaa Lys Xaa Gly Xaa Lys Xaa Gly
            20

<210> SEQ ID NO 15
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl lysine
<220> FEATURE:
<221> NAME/KEY: MOD_RES
<222> LOCATION: (2)..(2)
<223> OTHER INFORMATION: Xaa is Aib (2-aminoisobutyric acid)
<220> FEATURE:
<221> NAME/KEY: MOD_RES
<222> LOCATION: (5)..(5)
<223> OTHER INFORMATION: Xaa is Aib (2-aminoisobutyric acid)
<220> FEATURE:
<221> NAME/KEY: MOD_RES
<222> LOCATION: (8)..(8)
<223> OTHER INFORMATION: Xaa is Aib (2-aminoisobutyric acid)
<220> FEATURE:
<221> NAME/KEY: MOD_RES
<222> LOCATION: (11)..(11)
<223> OTHER INFORMATION: Xaa is Aib (2-aminoisobutyric acid)
<220> FEATURE:
```

-continued

```
<221> NAME/KEY: MOD_RES
<222> LOCATION: (14)..(14)
<223> OTHER INFORMATION: Xaa is Aib (2-aminoisobutyric acid)
<220> FEATURE:
<221> NAME/KEY: MOD_RES
<222> LOCATION: (17)..(17)
<223> OTHER INFORMATION: Xaa is Aib (2-aminoisobutyric acid)
<220> FEATURE:
<221> NAME/KEY: MOD_RES
<222> LOCATION: (18)..(18)
<223> OTHER INFORMATION: Amide glycine

<400> SEQUENCE: 15

Lys Xaa Gly Lys Xaa Gly Lys Xaa Gly Lys Xaa Gly Lys Xaa Gly Lys
1               5                   10                  15

Xaa Gly

<210> SEQ ID NO 16
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Lys is Acetyl lysine or Lys modified with
      N6-Arg-Pro-Lysinyl
<220> FEATURE:
<221> NAME/KEY: MOD_RES
<222> LOCATION: (2)..(2)
<223> OTHER INFORMATION: Xaa is Aib (2-aminoisobutyric acid)
<220> FEATURE:
<221> NAME/KEY: BINDING
<222> LOCATION: (4)..(4)
<223> OTHER INFORMATION: Lys modified with X-Pro-Arg-Lys. X represents
      the (-CH2NH-) binding
<220> FEATURE:
<221> NAME/KEY: MOD_RES
<222> LOCATION: (5)..(5)
<223> OTHER INFORMATION: Xaa is Aib (2-aminoisobutyric acid)
<220> FEATURE:
<221> NAME/KEY: BINDING
<222> LOCATION: (7)..(7)
<223> OTHER INFORMATION: Lys modified with N6-Arg-Pro-Lysinyl
<220> FEATURE:
<221> NAME/KEY: MOD_RES
<222> LOCATION: (8)..(8)
<223> OTHER INFORMATION: Xaa is Aib (2-aminoisobutyric acid)
<220> FEATURE:
<221> NAME/KEY: BINDING
<222> LOCATION: (10)..(10)
<223> OTHER INFORMATION: Lys modified with N6-Arg-Pro-Lysinyl
<220> FEATURE:
<221> NAME/KEY: MOD_RES
<222> LOCATION: (11)..(11)
<223> OTHER INFORMATION: Xaa is Aib (2-aminoisobutyric acid)
<220> FEATURE:
<221> NAME/KEY: BINDING
<222> LOCATION: (13)..(13)
<223> OTHER INFORMATION: Lys modified with N6-Arg-Pro-Lysinyl
<220> FEATURE:
<221> NAME/KEY: MOD_RES
<222> LOCATION: (14)..(14)
<223> OTHER INFORMATION: Xaa is Aib (2-aminoisobutyric acid)
<220> FEATURE:
<221> NAME/KEY: BINDING
<222> LOCATION: (16)..(16)
<223> OTHER INFORMATION: Lys modified with N6-Arg-Pro-Lysinyl
<220> FEATURE:
<221> NAME/KEY: MOD_RES
<222> LOCATION: (17)..(17)
<223> OTHER INFORMATION: Xaa is Aib (2-aminoisobutyric acid)
<220> FEATURE:
<221> NAME/KEY: MOD_RES
<222> LOCATION: (18)..(18)
<223> OTHER INFORMATION: Amide glycine
```

-continued

```
<400> SEQUENCE: 16

Lys Xaa Gly Lys Xaa Gly Lys Xaa Gly Lys Xaa Gly Lys Xaa Gly Lys
1               5                   10                  15

Xaa Gly

<210> SEQ ID NO 17
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Lys is Acetyl lysine or Lys modified with
      N6-Arg-Pro-Lysinyl
<220> FEATURE:
<221> NAME/KEY: BINDING
<222> LOCATION: (3)..(3)
<223> OTHER INFORMATION: Lys modified with N6-Arg-Pro-Lysinyl
<220> FEATURE:
<221> NAME/KEY: BINDING
<222> LOCATION: (6)..(6)
<223> OTHER INFORMATION: Lys modified with N6-Arg-Pro-Lysinyl
<220> FEATURE:
<221> NAME/KEY: BINDING
<222> LOCATION: (8)..(8)
<223> OTHER INFORMATION: Lys modified with N6-Arg-Pro-Lysinyl
<220> FEATURE:
<221> NAME/KEY: BINDING
<222> LOCATION: (11)..(11)
<223> OTHER INFORMATION: Lys modified with N6-Arg-Pro-Lysinyl
<220> FEATURE:
<221> NAME/KEY: BINDING
<222> LOCATION: (13)..(13)
<223> OTHER INFORMATION: Lys modified with N6-Arg-Pro-Lysinyl
<220> FEATURE:
<221> NAME/KEY: MOD_RES
<222> LOCATION: (15)..(15)
<223> OTHER INFORMATION: Amide glycine

<400> SEQUENCE: 17

Lys Ala Lys Pro Gly Lys Ala Lys Pro Gly Lys Ala Lys Pro Gly
1               5                   10                  15

<210> SEQ ID NO 18
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Aib (2-aminoisobutyric acid) or is
      Acetyl lysine
<220> FEATURE:
<221> NAME/KEY: MOD_RES
<222> LOCATION: (3)..(3)
<223> OTHER INFORMATION: Xaa is Aib (2-aminoisobutyric acid)
<220> FEATURE:
<221> NAME/KEY: MOD_RES
<222> LOCATION: (5)..(5)
<223> OTHER INFORMATION: Xaa is Aib (2-aminoisobutyric acid)
<220> FEATURE:
<221> NAME/KEY: MOD_RES
<222> LOCATION: (7)..(7)
<223> OTHER INFORMATION: Xaa is Aib (2-aminoisobutyric acid)
<220> FEATURE:
<221> NAME/KEY: MOD_RES
<222> LOCATION: (9)..(9)
<223> OTHER INFORMATION: Xaa is Aib (2-aminoisobutyric acid)
<220> FEATURE:
<221> NAME/KEY: MOD_RES
```

```
<222> LOCATION: (11)..(11)
<223> OTHER INFORMATION: Xaa is Aib (2-aminoisobutyric acid)
<220> FEATURE:
<221> NAME/KEY: MOD_RES
<222> LOCATION: (13)..(13)
<223> OTHER INFORMATION: Xaa is Aib (2-aminoisobutyric acid)
<220> FEATURE:
<221> NAME/KEY: MOD_RES
<222> LOCATION: (15)..(15)
<223> OTHER INFORMATION: Xaa is Aib (2-aminoisobutyric acid)
<220> FEATURE:
<221> NAME/KEY: MOD_RES
<222> LOCATION: (17)..(17)
<223> OTHER INFORMATION: Xaa is Aib (2-aminoisobutyric acid)
<220> FEATURE:
<221> NAME/KEY: MOD_RES
<222> LOCATION: (19)..(19)
<223> OTHER INFORMATION: Xaa is Aib (2-aminoisobutyric acid)
<220> FEATURE:
<221> NAME/KEY: MOD_RES
<222> LOCATION: (20)..(20)
<223> OTHER INFORMATION: Amide glycine

<400> SEQUENCE: 18

Xaa Lys Xaa Gly Xaa Lys Xaa Gly Xaa Lys Xaa Gly Xaa Lys Xaa Gly
1               5                   10                  15

Xaa Lys Xaa Gly
            20

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl lysine
<220> FEATURE:
<221> NAME/KEY: MOD_RES
<222> LOCATION: (2)..(2)
<223> OTHER INFORMATION: Xaa is Aib (2-aminoisobutyric acid)
<220> FEATURE:
<221> NAME/KEY: MOD_RES
<222> LOCATION: (5)..(5)
<223> OTHER INFORMATION: Xaa is Aib (2-aminoisobutyric acid)
<220> FEATURE:
<221> NAME/KEY: MOD_RES
<222> LOCATION: (8)..(8)
<223> OTHER INFORMATION: Xaa is Aib (2-aminoisobutyric acid)
<220> FEATURE:
<221> NAME/KEY: MOD_RES
<222> LOCATION: (11)..(11)
<223> OTHER INFORMATION: Xaa is Aib (2-aminoisobutyric acid)
<220> FEATURE:
<221> NAME/KEY: MOD_RES
<222> LOCATION: (14)..(14)
<223> OTHER INFORMATION: Xaa is Aib (2-aminoisobutyric acid)
<220> FEATURE:
<221> NAME/KEY: MOD_RES
<222> LOCATION: (15)..(15)
<223> OTHER INFORMATION: Amide glycine

<400> SEQUENCE: 19

Lys Xaa Gly Lys Xaa Gly Lys Xaa Gly Lys Xaa Gly Lys Xaa Gly
1               5                   10                  15

<210> SEQ ID NO 20
<211> LENGTH: 20
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MOD_RES
<222> LOCATION: (1)..(1)
<223> OTHER INFORMATION: Xaa is Aib (2-aminoisobutyric acid) or is
      Acetyl lysine
<220> FEATURE:
<221> NAME/KEY: BINDING
<222> LOCATION: (2)..(2)
<223> OTHER INFORMATION: Lys modified with N6-Arg-Pro-Lysinyl
<220> FEATURE:
<221> NAME/KEY: MOD_RES
<222> LOCATION: (3)..(3)
<223> OTHER INFORMATION: Xaa is Aib (2-aminoisobutyric acid)
<220> FEATURE:
<221> NAME/KEY: MOD_RES
<222> LOCATION: (5)..(5)
<223> OTHER INFORMATION: Xaa is Aib (2-aminoisobutyric acid)
<220> FEATURE:
<221> NAME/KEY: BINDING
<222> LOCATION: (6)..(6)
<223> OTHER INFORMATION: Lys modified with N6-Arg-Pro-Lysinyl
<220> FEATURE:
<221> NAME/KEY: MOD_RES
<222> LOCATION: (7)..(7)
<223> OTHER INFORMATION: Xaa is Aib (2-aminoisobutyric acid)
<220> FEATURE:
<221> NAME/KEY: MOD_RES
<222> LOCATION: (9)..(9)
<223> OTHER INFORMATION: Xaa is Aib (2-aminoisobutyric acid)
<220> FEATURE:
<221> NAME/KEY: BINDING
<222> LOCATION: (10)..(10)
<223> OTHER INFORMATION: Lys modified with N6-Arg-Pro-Lysinyl
<220> FEATURE:
<221> NAME/KEY: MOD_RES
<222> LOCATION: (11)..(11)
<223> OTHER INFORMATION: Xaa is Aib (2-aminoisobutyric acid)
<220> FEATURE:
<221> NAME/KEY: MOD_RES
<222> LOCATION: (13)..(13)
<223> OTHER INFORMATION: Xaa is Aib (2-aminoisobutyric acid)
<220> FEATURE:
<221> NAME/KEY: BINDING
<222> LOCATION: (14)..(14)
<223> OTHER INFORMATION: Lys modified with N6-Arg-Pro-Lysinyl
<220> FEATURE:
<221> NAME/KEY: MOD_RES
<222> LOCATION: (15)..(15)
<223> OTHER INFORMATION: Xaa is Aib (2-aminoisobutyric acid)
<220> FEATURE:
<221> NAME/KEY: MOD_RES
<222> LOCATION: (17)..(17)
<223> OTHER INFORMATION: Xaa is Aib (2-aminoisobutyric acid)
<220> FEATURE:
<221> NAME/KEY: BINDING
<222> LOCATION: (18)..(18)
<223> OTHER INFORMATION: Lys modified with N6-Arg-Pro-Lysinyl
<220> FEATURE:
<221> NAME/KEY: MOD_RES
<222> LOCATION: (19)..(19)
<223> OTHER INFORMATION: Xaa is Aib (2-aminoisobutyric acid)
<220> FEATURE:
<221> NAME/KEY: MOD_RES
<222> LOCATION: (20)..(20)
<223> OTHER INFORMATION: Amide glycine

<400> SEQUENCE: 20

Xaa Lys Xaa Gly Xaa Lys Xaa Gly Xaa Lys Xaa Gly Xaa Lys Xaa Gly
1               5                   10                  15

Xaa Lys Xaa Gly
            20

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MOD_RES
<222> LOCATION: (1)..(1)
<223> OTHER INFORMATION: Lys is Acetyl lysine or modified with
      N6-Arg-Pro-Lysinyl
<220> FEATURE:
<221> NAME/KEY: MOD_RES
<222> LOCATION: (2)..(2)
<223> OTHER INFORMATION: Xaa is Aib (2-aminoisobutyric acid)
<220> FEATURE:
<221> NAME/KEY: BINDING
<222> LOCATION: (4)..(4)
<223> OTHER INFORMATION: Lys modified with N6-Arg-Pro-Lysinyl
<220> FEATURE:
<221> NAME/KEY: MOD_RES
<222> LOCATION: (5)..(5)
<223> OTHER INFORMATION: Xaa is Aib (2-aminoisobutyric acid)
<220> FEATURE:
<221> NAME/KEY: BINDING
<222> LOCATION: (7)..(7)
<223> OTHER INFORMATION: Lys modified with N6-Arg-Pro-Lysinyl
<220> FEATURE:
<221> NAME/KEY: MOD_RES
<222> LOCATION: (8)..(8)
<223> OTHER INFORMATION: Xaa is Aib (2-aminoisobutyric acid)
<220> FEATURE:
<221> NAME/KEY: BINDING
<222> LOCATION: (10)..(10)
<223> OTHER INFORMATION: Lys modified with N6-Arg-Pro-Lysinyl
<220> FEATURE:
<221> NAME/KEY: MOD_RES
<222> LOCATION: (11)..(11)
<223> OTHER INFORMATION: Xaa is Aib (2-aminoisobutyric acid)
<220> FEATURE:
<221> NAME/KEY: BINDING
<222> LOCATION: (13)..(13)
<223> OTHER INFORMATION: Lys modified with N6-Arg-Pro-Lysinyl
<220> FEATURE:
<221> NAME/KEY: MOD_RES
<222> LOCATION: (14)..(14)
<223> OTHER INFORMATION: Xaa is Aib (2-aminoisobutyric acid)
<220> FEATURE:
<221> NAME/KEY: MOD_RES
<222> LOCATION: (15)..(15)
<223> OTHER INFORMATION: Amide glycine

<400> SEQUENCE: 21

Lys Xaa Gly Lys Xaa Gly Lys Xaa Gly Lys Xaa Gly Lys Xaa Gly
1               5                   10                  15
```

USE OF MULTIVALENT SYNTHETIC LIGANDS OF SURFACE NUCLEOLIN FOR TREATING CANCER OR INFLAMMATION

CROSS-REFERENCE TO RELATED APPLICATIONS

The present application claims the benefit of PCT/FR2007/000730, titled: Use of Multivalent Synthetic Ligands of Surface Nucleolin for Treating Cancer or Inflammation, filed: 27 Apr. 2007; which claims priority to French Patent Application FR 0603813, filed: 27 Apr. 2006.

INCORPORATION BY REFERENCE

In compliance with 37 C.F.R. §1.52(e)(5), an electronic CRF of the sequence listing is filed herewith: file name: D24262—Seq listing_US_ST25.txt; size 17 KB; created on: Jan. 3, 2011; using PatentIn-3.5, and Checker 4.4.0 is hereby incorporated by reference in its entirety. The data in the Computer Readable Form of the Sequence Listing submitted herewith contains no new matter, and is fully supported by the priority application, PCT/FR2007000730 filed 27 Apr. 2007.

FIELD OF THE INVENTION

The present invention relates to the use of a multivalent synthetic compound, which is significantly more resistant to at least one protease than a standard peptide bond, for preparing a medication intended for the treatment of a diseases involving deregulation of cell proliferation and/or angiogenesis, and preferably acting as a surface nucleolin ligand.

BACKGROUND

Cell division, or mitosis, is the process which allows cells to multiply in order to repair or regenerate tissues and replace dead cells. In cancer cells, regulation of this process is defective and this is why these cells divide anarchically and give rise to tumours. Thus, one effective therapeutic route to prevent the development of cancer consists in blocking the division of cancerous cells using molecules with anti-mitotic properties.

Nevertheless, current anti-mitotic molecules (paclitaxel, better known under the name taxol, or colchicine for example) act without cell specificity on all cells without distinction, thus causing many unwanted side effects. It is therefore essential to develop anti-mitotic molecules with fewer harmful effects.

Every tumour needs nutrients and oxygen in order to grow. These elements are provided by intratumoral blood vessels which result from a mechanism known as angiogenesis. In fact, if these vessels are absent, tumour cells undergo a cell necrosis process, and tumour growth slows down then stops. An example of another therapeutic route to combat cancer therefore consists in blocking the angiogenesis process by blocking the molecules controlling this mechanism.

The plurality of current anti-angiogenic molecules are specific to one angiogenic factor. This monospecificity gives rise to resistance phenomena Inhibition of one angiogenic factor type produces expression of another type by angiogenic compensation mechanisms. It is therefore beneficial to have available anti-angiogenic molecules with a broad spectrum of activity against the factors implicated.

However, inhibition of the angiogenesis process alone is generally found to be insufficient to effectively block tumour growth. In addition, it does not block the formation of metastases.

It would therefore be extremely useful to have available new anti-cancer molecules capable of inhibiting both tumour cell proliferation and the angiogenesis process in the tumour. In fact, a recent study has shown that a combination of two therapeutic molecules, one anti-mitotic and the other anti-angiogenic, produces a synergetic effect and significantly increases the efficacy of overall treatment compared to treatment with only one of these molecules.

No molecule with both these effects, anti-mitotic and anti-angiogenic, has yet been reported.

Moreover, the majority of current anti-cancer agents are not truly specific to tumour cells and therefore also target healthy cells, thus giving rise to many, and at times serious, side effects. This problem has been resolved in some cases by the development of antibodies which target the surface molecules of some tumours. However, the use of antibodies poses other serious problems and the development of effective therapeutic antibodies that are non-toxic is a lengthy, uncertain and expensive procedure. Moreover, the production of antibodies on a large scale and under strict health and safety conditions is particularly difficult. As a result, treatments based on specific antibodies are still far and few between and extremely costly.

Another problem linked to conventional anti-cancer drugs, such as paclitaxel, is that these molecules are often highly hydrophobic which makes it necessary to develop complicated and expensive pharmaceutical formulations in order to achieve acceptable bioavailability in vivo. The problem of in vivo bioavailability is all the more acute in the case of treatment using nucleic acids since it is extremely difficult for them to reach their target cells in an efficacious and specific manner.

It would therefore be extremely useful to have available new anti-cancer molecules which present the following characteristics: much improved efficacy as a result of their dual inhibitory action on tumour proliferation and angiogenesis such that they can be effective alone, without the use of conventional chemotherapy or radiotherapy and thus greatly the limit side effects linked to these types of treatment, a fairly broad spectrum of activity against angiogenic factors to prevent resistance to treatment, very few side effects as a result of greater specificity towards tumour cells, a synthesis process that is easily adaptable to an industrial scale, easier to use, notably as a result of better bioavailability and/or longer half-life in vivo, in particular as a result of direct specificity for tumour cells, with good solubility in aqueous media and improved resistance to in vivo breakdown processes.

DESCRIPTION

The present invention relates to the use of a multivalent synthetic compound comprising or consisting of a support on which at least 3 pseudopeptide units are grafted, said compound being of formula (I):

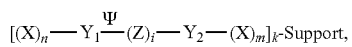

$$[(X)_n - Y_1 \overset{\Psi}{-} (Z)_i - Y_2 - (X)_m]_k\text{-Support,} \quad (I)$$

where each X independently represents any amino acid; $Y_1$ and $Y_2$ are selected independently from amino acids having a basic side chain; Z is selected from proline, optionally substituted at γ, β or δ; a natural or non N-alkylamino acid; a dialkylamino acid; a cyclic dialkylamino acid; pipecolic acid or a derivative thereof; n and i independently are 0 or 1; m is an integer between 0 and 3; k is an integer greater than or equal to 3; and Ψ represents a modified peptide bond which is significantly more resistant to at least one protease than a standard peptide bond, for preparing a medication intended for the treatment of a diseases involving deregulation of cell proliferation and/or angiogenesis, and preferably acting as a surface nucleolin ligand.

Figure 1:
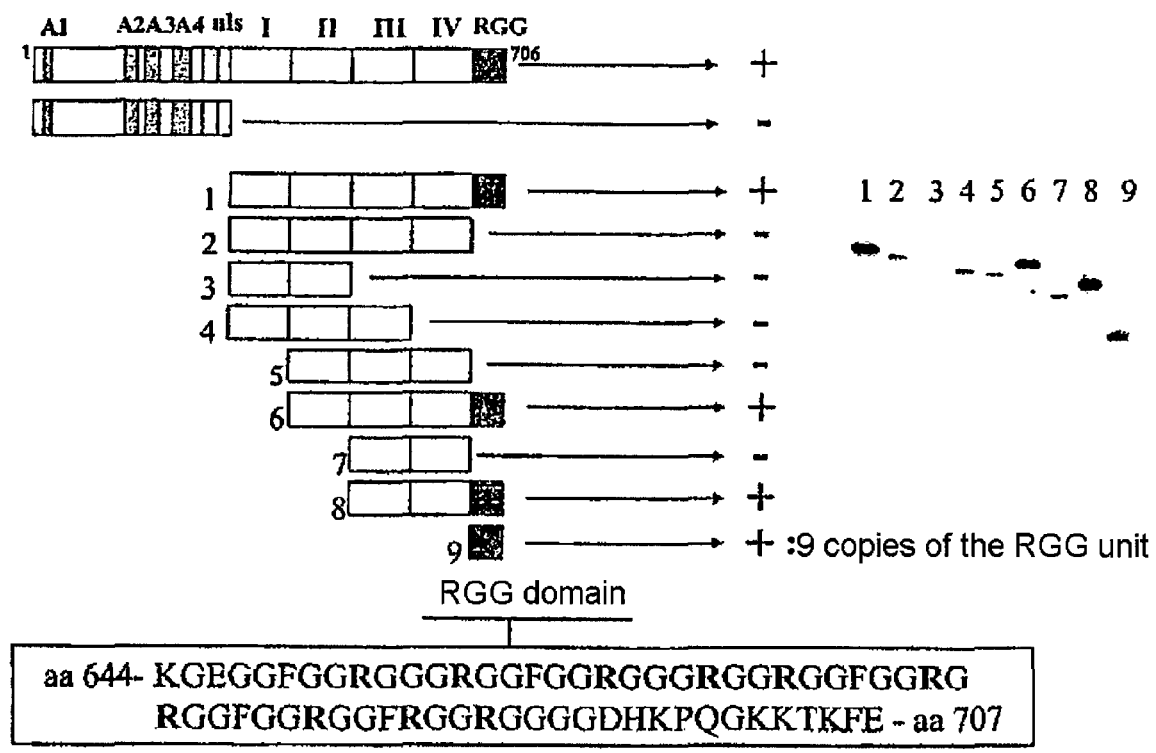
FIG. 1. A. Structure of nucleolin protein. Human nucleolin consists of 707 amino acids. Nucleolin can be broken down into two main parts: (3,4): N-terminal (aa 1-308) and C-terminal (309-706). The N-terminal domain consists of 4 long acid domains, consisting of an uninterrupted repetition of glutamic acid and aspartic acid (A1, A2, A3, A4). The C-terminal domain, consisting of alternating hydrophobic and hydrophilic regions forming 4 areas of binding to RNA called RBDs (for <<RNA Binding Domains>>: I, II, III, IV) and its extremity (aa 644-707) carries the highly basic RGG domain comprised of Arg-Gly-Gly repetitions. B. Identification of the binding domain of compound HB19 to nucleolin: the RGG domain. Nucleolin constructions corresponding to the N- and C-terminal areas were obtained by in vitro transcription/translation in a system using rabbit reticulocyte lysates. Thus, whole nucleolin and the N- and C-terminal parts contain amino acids 1-707, 1-308 and 309-707 respectively labelled with [$^{35}$S] Met/Cys were produced. The labelled crude product was then incubated with biotinylated HB19 and the complexes were purified on an avidine-agarose column. As expected, whole nucleolin interacts with HB19. On the other hand, the N-terminal part of the nucleolin rich in acid residues does not interact at all with the compound whereas the C-terminal part of nucleolin contains the target for HB19 (14). Having identified that the C-terminal part of the nucleolin contains the target for HB19, various constructions (No. 1 to 9) of this region were made up. The first construction corresponds to cDNA coding for the C-terminal part of human nucleolin including the 4 RBDs and the RGG domain, in fusion with GST protein (Glutathione S-Transferase) to allow detection with anti-GST antibodies. The other constructions, also in fusion with GST, correspond to this same part but one or more domains shorter. All these proteins are produced by *E. coli*. The capacity of HB19 to interact with each construction was tested by incubating crude bacterial extracts, expressing different nucleolin constructions, with biotinylated HB19 which was then purified by fixing to Avidine-agarose. These samples were then analysed by polyacrylamide gel and GST, and revealed by immunodetection (Western Blot) using anti-GST antibodies. The results show that the presence of the RGG domain is necessary for the interaction between HB19 with the C-terminal part of nucleolin. Moreover, the RGG domain alone is enough for this interaction.

Nucleolin (see structure in FIG. 1A) was initially described as a nuclear protein present in the majority of eukaryotic cells. More recently, it has been shown that in spite of the absence of a transmembrane domain allowing its attachment to the plasma membrane, another molecular form of this protein is also present on the cell surface (1-4). This surface nucleolin is closely associated with intracellular actin microfilaments. This association most probably takes place indirectly via a transmembrane partner.

In the resting cell, nucleolin is found mainly in the nucleolus but also partially in the cytoplasm and on the cell surface. Following activation of cell proliferation, cytoplasmic nucleolin is translocated towards the membrane surface by means of an active transport, non-conventional mechanism independent of the endoplasmic reticulum and Golgi apparatus (1).

The degree of surface nucleolin expression is therefore greatly increased following activation of cells, especially activation of cell proliferation. Surface nucleolin therefore constitutes a marker for activated cells in the proliferation phase. In the particular case of human immunodeficiency virus (HIV), which targets activated cells, it has been shown that surface nucleolin might be involved in cell infection by HIV (2,5).

Moreover, it has also been shown that surface nucleolin is expressed at the surface of tumour cells, such as tumour cells derived from hepatic carcinoma (6), T-lymphocyte leukaemia (7 and 8) and uterine cancer cells (7), as well as at the surface of activated endothelial cells (9), cells which are involved in the angiogenesis process. Moreover, surface nucleolin constitutes a receptor with weak affinity for various ligands, namely for several growth factors such as midkine (MK), heparin affin regulatory peptide (HARP, also known as pleiotrophin: PTN) and lactoferrin (10-12).

Recently, it was suggested in patent application WO 2005/035579 that it was possible to treat cancer using nucleolin binding agents, such as anti-nucleolin antibodies, anti-nucleolin interfering RNA or antisense anti-nucleolin oligonucleotides. The main results presented show that surface nucleolins can be considered to be a marker for cancer cells, which in itself does not make for a good target. Only preliminary results in mice show that the addition of anti-nucleolin antibodies can improve tumour regression by taxol. However, no results have been published proving the efficacy of such antibodies alone and the dose required to obtain this improvement in combination with taxol is not given. Moreover, use of antibodies in vivo in humans, as mentioned previously, poses serious problems in terms of administration.

Anti-nucleolin agents can act along different pathways. In particular, such agents may or may not act by binding to the protein nucleolin. For interfering RNA type agents or antisense anti-nucleolin oligonucleotides, these agents may possibly act at the level of intracellular nucleic acid and not at the level of binding to nucleolin. For example, in patent application US 2005/0026860, antisense nucleolin oligonucleotides are described as having a positive effect on tumour regression in vivo in a murine model. Nevertheless, the effect observed in mice is partial, with a smaller tumour developing in spite of this, and no effect on angiogenesis is described or suggested. While these results suggest that nucleolin could be considered to be a target in the treatment of cancer, suggest average efficacy not likely to lead to the possibility of treatment with an anti-nucleolin agent alone but rather simply as adjuvant treatment in addition to conventional chemotherapy. Moreover, as mentioned earlier, the use of oligonucleotides in vivo poses serious bioavailability problems.

Figure 2:
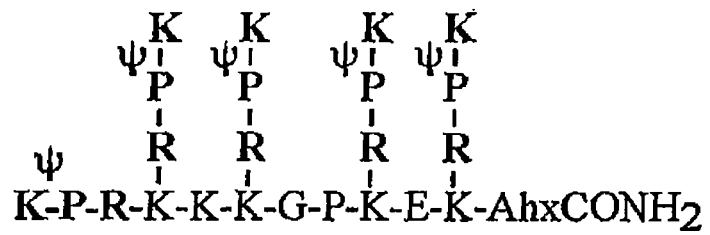
FIG. 2. A. Structure of compound HB19. B. Structure of trivalent compound Nucant 01 with a cyclic hexapeptide consisting of alternating alanine residues (A) of configuration D and lysine residues (K) of configuration L as the support. Three pseudopeptide units KΨPR (with Ψ=CH$_2$—N) are covalently bound to the e amino group of each of the lysine residues. C. Structure of pentavalent compound Nucant 2 (SEQ ID NO:10) with a linear peptide as a support having a helicoidal structure of sequence SEQ ID NO:8 in which 5 pseudopeptide units KΨPR (with Ψ=CH$_2$—N) are covalently bound to the ε amino group of each of the 5 lysine residues, Ac represents a CH$_3$—CO— group. D. Structure pentavalent compound Nucant 3 (SEQ ID NO:11) with a linear peptide as a support having a helicoidal structure of sequence SEQ ID NO:9 in which 5 pseudopeptide units KΨPR (with Ψ=CH$_2$—N) are covalently bound to the ε amino group of each of the 5 lysine residues, Ac represents a CH$_3$—CO— group. E. Structure of hexavalent compound Nucant 6 (SEQ ID NO:16) with a linear peptide as a support having a helicoidal structure of sequence SEQ ID NO:15 in which 5 pseudopeptide units KΨPR (with Ψ=CH$_2$—N) are covalently bound to the ε amino group of each of the 6 lysine residues, Ac represents a CH$_3$—CO— group. F. Structure of hexavalent compound Nucant 7 (SEQ ID NO:17) with a linear peptide as a support having a helicoidal structure of sequence SEQ ID NO:13 in which 6 pseudopeptide units KΨPR (with Ψ=CH$_2$—N) are covalently bound to the ε amino group of each of the 6 lysine residues, Ac represents a CH$_3$—CO— group.
Figure 2:
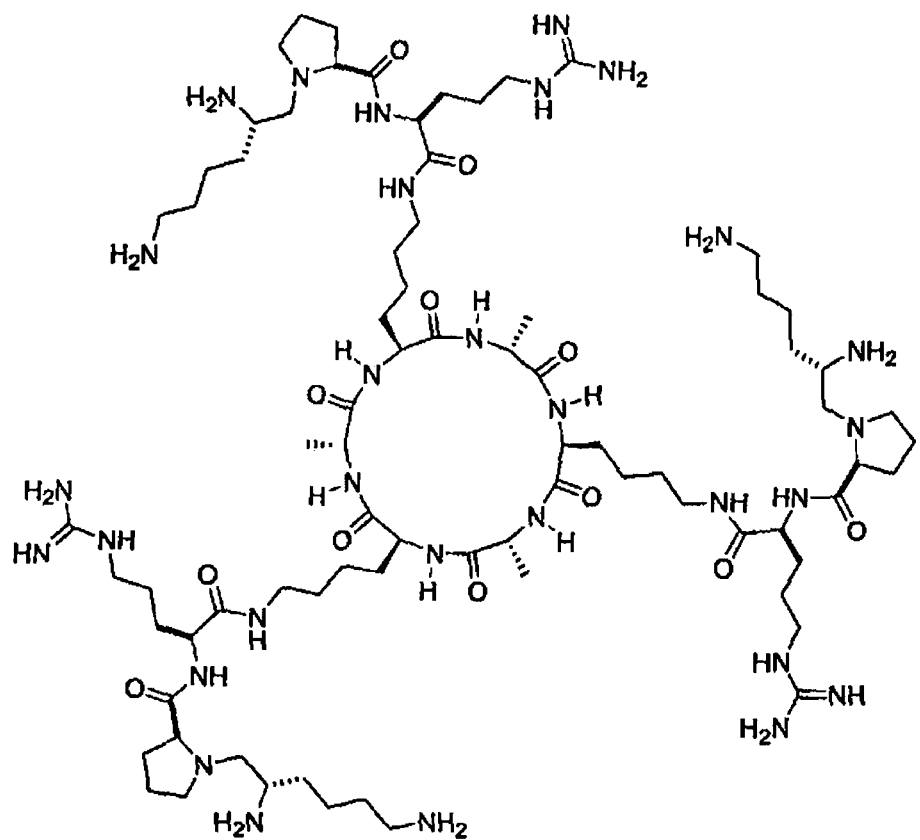

An anti-nucleolin agent can also bind directly to nucleolin protein. Various nucleolin ligands have been described in the literature: peptide F3 (or tumour-homing peptide) is a peptide corresponding to a 34 amino acid fragment of protein HMG2N which binds to activated endothelial cells of the vessels of various types of tumour. Recently, it has been shown that peptide F3 binds to nucleolin expressed in endothelial cells and is then internalised and transported into the nucleus by means of an active process. Binding to nucleolin and internalisation are blocked by anti-nucleolin antibodies. It has been reported that peptide F3 binds to the N-terminal area of nucleolin which contains several amino acid rich regions (9). In this application, the inventors show that peptide F3 is incapable of inhibiting cell proliferation of NIH-3T3 cells triggered by growth factor HARP (see example 1.1.1). Simply binding to surface nucleolin and being internalised is therefore not enough to confer the capacity to inhibit tumour cell proliferation on this peptide;

Multivalent compound HB19 (see FIG. 2A), synthesised and described by the inventors, is also a surface nucleolin ligand (7, 8, 13, 14) which interacts with the RGG domain (see FIG. 1B). It has been shown that this compound might make it possible to inhibit the infection of cells activated by HIV (13) as well as the binding of other natural ligands to nucleolin (10-12). However, no result has been reported demonstrating its possible ability to reduce and/or inhibit tumour growth or angiogenesis; patent application WO 00/61597 described guanine-rich oligonucleotides (GROs) as binding to a protein likely to be nucleolin and inhibiting the proliferation of tumour cells in vitro at doses greater than or equal to 15 μM (15). In vivo, only the existence of a certain synergy alongside conventional chemotherapy treatment is mentioned. No effect on angiogenesis is described or suggested. Moreover, it would seem that GROs bind mainly to intracellular nucleolin; in an article published by the team which registered patent WO 00/61597, another mixed oligonucleotide called MIX1, which includes G and T bases such as GROs in their samesense sequence but also A and C bases, is described as binding to nucleolin with the same efficacy as GROs but with no effect on cell proliferation, which once again suggests that simply binding to nucleolin is not enough to confer the ability to inhibit cell proliferation (15); recently, a team has shown that it is possible to inhibit angiogenesis induced by VEGF by means of a preparation containing anti-nucleolin polyclonal antibodies (16). However, although the anti-nucleolin polyclonal antibody preparation blocks the formation of tubules by endothelial cells, it does not block the proliferation of endothelial cells. In addition, only angiogenesis induced by VEGF was tested whereas there are many other factors involved in angiogenesis and no result showing inhibition of cell proliferation is described nor suggested.

It is clear from the description above that not all ligands of nucleolin show anti-tumour activity and none of the above-cited documents suggests that any of these ligands is likely to inhibit both the proliferation of tumour cells in general and angiogenesis triggered by various factors.

Moreover, it is crucial to note that the results presented, whether taken singly or together, in no way suggest that these ligands might possess sufficient activity to be used alone, without being combined with conventional anti-cancer treatments (radiotherapy or, more especially, conventional chemotherapy such as taxol).

However, the inventors have surprisingly shown that the pentavalent peptide compound HB19, or other compounds with at least 3 pseudopeptide units of the same type grafted on a support, make it possible to inhibit the proliferation of tumour cells in general, whether they are dependently or independently anchored (proliferation that is characteristic of transformed cells) or triggered by various growth factors, as well angiogenesis triggered by various factors. Moreover and more importantly, the inventors show in a murine model that pentavalent compound HB19 allows in vivo inhibition of both tumour proliferation and angiogenesis but also that the anti-tumour effect of compound HB19 at the usual dose for a peptide (5 mg/kg) is greater than that of taxol at 10 mg/kg, which is one of the standard molecules used in anti-tumour treatment.

Therefore while the other previously described ligands of surface nucleolin appear to have only a partial effect likely to lead to adjuvant type treatment, compound HB19 in vivo in mice shows greater efficacy than taxol, the standard anti-cancer molecule, suggesting the possibility of using it alone and not in combination with a conventional chemotherapy molecule. Notably, the taxol dose administered does lead to tumour regression but the regression is not total since a tumour was found and weighed once mice were sacrified. To the contrary, with multivalent ligand HB19 at a dose that is 2 times lower, no tumour was found in mice after their death, thus demonstrating full regression.

Multivalent compound HB19 therefore appears to be a highly powerful anti-cancer agent. This effect is probably linked to its dual ability as demonstrated by the inventors to inhibit both the proliferation of tumour cells, whether triggered by several distinct growth factors or even independently of anchorage, and the angiogenesis process triggered by 2 distinct angiogenic factors.

In addition, no toxic effect was found by the inventors, whether on cells cultured in vitro for several weeks in the presence of compound HB19 or in vivo in mice treated with compound HB19. Moreover, purification of proteins bound to multivalent compound HB19 after in vivo administration makes it possible to obtain over 90% surface nucleolin, suggesting great specificity of interaction between multivalent compound HB19 and nucleolin. This greatly limits the possibility of the occurrence of side effects. The inventors have also shown that although peptide HB19 can be internalised after binding to surface nucleolin, it does not reach the nucleus, an important fact to explain the absence of toxicity for healthy cells.

Compound HB19 and derivatives or analogues thereof are also easily synthesised, even on an industrial scale, under easily controllable health safety conditions.

Finally, its specificity for nucleolin as well as for tumour cells and activated endothelial cells, its pseudopeptide nature and its high solubility in aqueous media means that it has very good bioavailability in vivo. The specificity of compound HB19 for surface nucleolin does not require any coupling with a target molecule. Moreover, the presence of a modified peptide bond (reduced in the case of compound HB19) between the lysine and proline of each KPR unit presented in the case of HB19 confers on it good resistance to proteases in vivo and an in vivo half life of over 24 hours, contrary to conventional peptides whose in vivo half life does not exceed half an hour. In addition, compound HB19 is totally soluble in aqueous media which makes its administration much easier as no particular pharmaceutical form is required for its circulation and targeting in vivo.

Pentavalent compound HB19 therefore presents all the necessary characteristics needed to resolve the various technical problems of supplying new anti-cancer compounds:

which are capable of having high anti-tumour efficacy alone as a result of a dual effect on tumour proliferation and angiogenesis, efficacy that makes it possible to envisage a single treatment without being combined with a conventional chemotherapy molecule such as taxol;

which do not have specificity for a particular type of cancer but rather a broad spectrum of activity against tumour cells and activated endothelial cells;

which have very few side effects in vivo as a result of specificity for tumour cells and activated endothelial cells compared to healthy cells;

which have a synthesis process that can be easily adapted to an industrial scale; and which have sufficient bioavailability in vivo in order not to require the development of particular pharmaceutical forms.

The invention therefore relates to the use of a multivalent synthetic compound comprising or constituted of a support on which is grafted at least 3 pseudopeptide units, said compound being of formula (I):

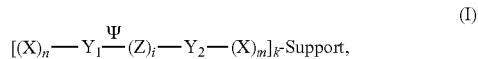

$$[(X)_n - Y_1 \overset{\Psi}{-} (Z)_i - Y_2 - (X)_m]_k\text{-Support},\qquad (I)$$

Wherein each X independently represents any amino acids;

$Y_1$ and $Y_2$ are independently selected from basic natural chain amino acids;

Z is selected from: proline, possibly substituted at $\gamma$, $\beta$ or $\delta$ by hydroxyl, amine, $C_1$-$C_{10}$ alkyl, $C_1$-$C_{10}$ alkenyl, $C_1$-$C_{10}$ alkynyl, $C_5$-$C_{12}$ aryl, $C_5$-$C_{14}$ aralkyl, $C_5$-$C_{12}$ heteroaryl (advantageously $C_5$ heteroaryl) groups, these groups being themselves possibly substituted by 1 to 6 substituents selected from a halogen atom, $NO_2$, OH, $C_1$-$C_4$ alkyl, $NH_2$, CN, trihalomethyl, $C_1$-$C_4$ alkyloxy, $C_1$-$C_4$ dialkylamino, guanidino group, thiol group;

N-alkylamino acid, natural or not;

dialkylamino acid;

cyclic dialkylamino acid; or pipecolic acid or derivatives thereof;

n and i are independently 0 or 1;

m is an integer between 0 and 3; k is an integer greater than or equal to 3; and Ψ represents a modified peptide bond significantly more resistant to at least one protease than a standard peptide bond, for the manufacture of a medication intended for the treatment of disorders involving deregulation of cell proliferation and/or angiogenesis.

Preferably, such a multivalent synthetic compound acts as a ligand for the surface nucleolin.

In the context of the invention, the term "support" refers to any pharmaceutically acceptable molecule, in other words without intrinsic toxicity, on which at least 3 pseudopeptide units of formula (I) can be grafted. An acceptable support therefore has to be of sufficient size to allow at least 3 pseudopeptide units of formula (I) to be grafted on it, preferably 3 to 8 pseudopeptide units of formula (I). Such an acceptable support should also preferably be large enough to allow at least 3, preferably 3 to 8, pseudopeptide units of formula (I) can come together to interact in the RGG domain of one or more nucleolin molecules. In addition, the support must not be immunogenic.

Such a support can be selected from a linear peptide or cyclic peptide, a peptoid (N-substituted glycine oligomer) that is linear or cyclic, a foldamer (oligomer or polymer with a strong tendency to adopt a compact, well-defined and predictable conformation in solution), a linear polymer or a spherical dendromer (macromolecule consisting or polymers which combine according to a tree like process around a multifunctional central core) a sugar or a nanoparticle. Advantageously, said support is selected from a linear or a cyclic peptide or even a linear or cyclic peptoid.

The use of a linear peptide (see structure of HB19 in FIG. 2A) allows the support to be synthesised easily and the results obtained by the inventors with compound HB19 show that such a support does in effect resolve the technical problems posed by this application. A linear peptide acting as a support in the invention can advantageously contain a proportion of lysine greater than 25%. More precisely, when a linear peptide is used as a support in the invention, the pseudopeptide units are preferably grafted in position ☐☐☐ of lysine. When a linear peptide is used as the support in the invention, it therefore preferably includes at least as many lysine as the number of pseudopeptide units which are to be grafted on.

For example, a support linear peptide can have a sequence selected from KKKGPKEKGC (SEQ ID NO:1), KKKKGC (SEQ ID NO:2), KKKKGPKKKKGA (SEQ ID NO:3) or KKKGPKEKAhxCONH₂ (SEQ ID NO:4), wherein Ahx represents hexanoic amino acid and CONH₂ represents the fact that the acid group is replaced by an amide group, Ahx-CONH₂, representing (2S)-2-aminohexanamide, or a linear sequence consisting of 2-4 units (KAKPG, SEQ ID NO:12), namely sequence AcKAKPGKAKPGKAKPGCONH₂ (SEQ ID NO:13, where Ac represents an acetyl group CH₃—CO—, and CONH₂ means that the acid group COOH of glycine is replaced by an amide group CONH₂). Advantageously, the support linear peptide can be peptide KKKGPKEKAhx-CONH₂ (see for example HB19 in FIG. 2A, SEQ ID NO:5, which has this linear peptide as support.), or peptide AcK-AKPGKAKPGKAKPGCONH₂ (SEQ ID NO:4, where Ac represents an acetyl group CH₃—CO— and CONH₂ means that the acid group COOH of glycine is replaced by an amide group CONH₂, for example, Nucant 7 in FIG. 2F, SEQ ID NO:17, which has this linear peptide as a support).

Among the linear peptides, some are known to adopt a helicoidal structure. These linear peptides can also be used as supports in the invention. Such linear peptide supports from a helicoidal structure comprised of supports consisting of an integer greater than or equal to 3, namely 3 to 8, repetitions of the peptide units of sequence Aib-Lys-Aib-Gly (SEQ ID NO:6) or Lys-Aib-Gly (SEQ ID NO:7) respectively where Aib represents 2-amino-isobutyric acid. As each of these units consists of a single lysine residue (Lys), as many repetitions of these units are needed as are to be grafted on pseudopeptide units of formula (I).

For example, to obtain a pentavalent compound with 5 pseudopeptide units of formula (I), the support can be a linear peptide forming a helicoidal structure of formula Aib-Lys-Aib-Gly-Aib-Lys-Aib-Gly-Aib-Lys-Aib-Gly-Aib-Lys-Aib-Gly-Aib-Lys-Aib-Gly (SEQ ID NO:8) or Lys-Aib-Gly-Lys-Aib-Gly-Lys-Aib-Gly-Lys-Aib-Gly-Lys-Aib-Gly (SEQ ID NO:9). Advantageously, a linear peptide forming a helicoidal structure of formula derived from SEQ ID NO:8 and 9 is used. This formula is selected from Ac-Aib-Lys-Aib-Gly-Aib-Lys-Aib-Gly-Aib-Lys-Aib-Gly-Aib-Lys-Aib-Gly-Aib-Lys-Aib-Gly-CONH₂ (SEQ ID NO:18, where Ac represents an acetyl group CH₃—CO— and CONH₂ means that the COOH acid group of glycine is replaced by an amide group CONH₂, see for example Nucant 2 in FIG. 2C, SEQ ID NO:20, which has this peptide as a support) or Ac-Lys-Aib-Gly-Lys-Aib-Gly-Lys-Aib-Gly-Lys-Aib-Gly-Lys-Aib-Gly-CONH₂ (SEQ ID NO:19, where the Ac group represents an acetyl group CH₃—CO— and CONH₂ means that the COOH acid group of glycine is replaced by an amide group CONH₂, see for example Nucant 3 in FIG. 2D, SEQ ID NO:21, which has this peptide as a support).

Alternatively, to obtain a hexavalent compound with 6 pseudopeptide units of formula (I), the support used can be a linear peptide forming a helicoidal structure of formula Ac-Aib-Lys-Aib-Gly-Aib-Lys-Aib-Gly-Aib-Lys-Aib-Gly-Aib-Lys-Aib-Gly-Aib-Lys-Aib-Gly-Aib-Lys-Aib-Gly-CONH₂ (SEQ ID NO:14, where Ac represents a CH₃—CO— group and CONH₂ means that the acid group COOH of glycine is replaced by an amide group CONH₂) or Ac-Lys-Aib-Gly-Lys-Aib-Gly-Lys-Aib-Gly-Lys-Aib-Gly-Lys-Aib-Gly-Lys-Aib-Gly-CONH₂ (SEQ ID NO:15, where Ac represents a CH₃—CO— group and CONH₂ means that the acid group COOH of glycine is replaced by an amid group CONH₂, see for example Nucant 6 in FIG. 2E, SEQ ID NO:17, which has this peptide as a support).

A cyclic peptide or peptoid can also be advantageously used as support. In particular, this allows the flexibility of the structure to be restricted. A support cyclic peptide or peptoid can be mainly be selected from hexa-, octa-, deca- or dodeca-cyclic peptide, preferably consisting of amino acid residues in the L (levorotatory) and D (dextrorotatory) configuration in alternation (D,L-cyclopeptide) or a chain of N-alkyl Glycine residue (cyclic peptoid). An example of a compound with such a support is a cyclic hexapeptide consisting of alternate alanine (A) residues of configuration D and lysine residues (K) of configuration L with 3 KPR units with a Ψ (Ψ= (CH₂N—)) bond between K and P as shown in FIG. 2B (compound Nucant 01).

Advantageously, the support for a compound of formula (I) according to the invention is a support selected from a cyclic hexapeptide consisting of alternating alkaline (A) residues of configuration D and Lysine (K) residues of configuration L or a linear peptide of sequence SEQ ID NO:1, SEQ ID NO:2, SEQ ID NO:3, SEQ ID NO:4, SEQ ID NO:8, SEQ ID NO:9, SEQ ID NO:13, SEQ ID NO:14, SEQ ID NO:15, SEQ ID NO:18, or SEQ ID NO:19.

In the context of the invention, the term "grafted" for the pseudopeptide units means being bound to the support by means of a covalent bond, either directly or through the intermediate of a spacer compound between the pseudopeptide and support. As a result of this, in one particular embodiment, the pseudopeptide units are grafted directly on the support without a spacer compound between them and the support. In another embodiment, the pseudopeptide units are grafted on the support through the intermediate of a spacer. Examples of acceptable spacers include compounds of the type ethylene glycol, piperazine or an amino acid of the type aminohexanoic acid or beta-alanine.

In the case where the support is a linear or cyclic peptide and where the pseudopeptide units are grafted directly on the peptide, bonding between the peptide and the pseudopeptide units is preferably carried out at the lysine residue of the peptide support, at the amino group in the α or ε position, preferably at the amino group in the ε position (on the side chain) of lysine. Thus, direct grafting of pseudopeptide units on the peptide support is advantageously carried out by means of an amide bond between the acid group COOH of the amino acid in the C-terminal position of the pseudopeptide unit and an amino group of the lysine residue, preferably the amino group in the ε position (on the side chain) of lysine.

In the compounds according to the invention, at least 3 pseudopeptide units are grafted on the support. In fact, the inventors' results show the importance of binding to the RGG domain of nucleolin (see FIG. 1) for exceptional anti-tumour efficacy of compound HB19 and derivative compounds or analogues. Binding to the RGG domain of nucleolin is obtained by means of multivalent presentation of several pseudopeptide units such as those incorporated into formula (I). For compounds for which the support is a linear peptide of sequence KKKGPKEKGC, KKKKGC, KKKKGPKKKKGA or KKKGPKEKAhxCONH$_2$, the inventors have shown that below 3 units (k<3), the efficacy of binding to nucleolin is lower and anti-tumour efficacy is probably less. The compounds according to the invention therefore include at least 3 pseudopeptide units grafted on the support, k being an integer greater than or equal to 3. The compounds according to the invention therefore advantageously present 3-8 pseudopeptide units ($3 \leq k \leq 8$) grafted on the support. Moreover, the inventors have shown that activity was optimal with 5 or 6 pseudopeptide units grafted on the support (k=5), since the efficacy of binding to nucleolin does not increase with a higher number of pseudopeptide units. Advantageously, in the compounds of formula (I), k is therefore between 3 and 8, preferably between 4 and 7, between 4 and 6, between 4 and 5, or between 5 and 6. Even more advantageously, in compounds of formula (I), k is equal to 5 or even better 6.

In the context of the invention, the term "any amino acid" means any natural or synthetic amino acid, possibly modified by the presence of one or more substituents. More precisely the term amino acid means an alpha aminated amino acid with the following general structure:

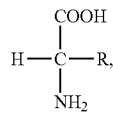

where R represents the side chain of the amino acid. In the context of the invention, R therefore represents the side chain of a side or non-side amino acid. The term "natural amino acid" means any amino acid which is found naturally in vivo in a living being. Natural amino acids therefore include amino acids coded by mRNA incorporated into proteins during translation but also other amino acids found naturally in vivo which are a product or by-product of a metabolic process, such as for example ornithine which is generated by the urea production process by arginase from L-arginine. In the invention, the amino acids used can therefore be natural or not. Namely, natural amino acids generally have the L configuration but also, according to the invention, an amino acid can have the L or D configuration. Moreover, R is of course not limited to the side chains of natural amino acid but can be freely chosen.

In the pseudopeptide units of compounds of formula (I), Z is either absent (i=0), or present (i=1) and is then selected from:

proline, possibly substituted at γ, β or δ by hydroxyl groups, amine, $C_1$-$C_{10}$ alkyl, $C_1$-$C_{10}$ alkenyl, $C_1$-$C_{10}$ alkynyl, $C_5$-$C_{12}$ aryl, $C_5$-$C_{14}$ aralkyl, $C_5$-$C_{12}$ heteroaryl (advantageously a $C_5$ heteroaryl), these groups themselves possibly being substituted by 1 to 6 substituents selected from a halogen atom, $NO_2$, OH, $C_1$-$C_4$ alkyl, $NH_2$, CN, trihalomethyl, $C_1$-$C_4$ alkyloxy, $C_1$-$C_4$ dialkylamino, guanadino group, thiol group; N-alkylamino acid, natural or not; dialkylamino acid (for example isobutyric amino acid); cyclic dialkylamino acid; or pipecolic acid or derivatives thereof.

The term "$C_1$-$C_i$ alkyl" means a linear or branched saturated hydrocarbon radical of formula —$C_jH_{2j+1}$, where $1 \leq j \leq i$. The $C_1$-$C_{10}$ alkyl therefore includes $C_1$ alkyls (methyl), $C_2$ (ethyl), $C_3$ (n-propyl, or isopropyl), $C_4$ (n-butyl, isobutyl, sec-butyl or tert-butyl), $C_5$ (eg: n-pentyl, neopentyl, isopentyl, tert-pentyl), and $C_6$ to $C_{10}$ alkyls. The term "$C_1$-$C_{10}$ alkanyl" means a linear or branched unsaturated hydrocarbon radical consisting of 1 to 10 carbon atoms and including at least one C=C double bond. The term "$C_1$-$C_{10}$ alkynyl" means a linear or branched unsaturated hydrocarbon radical with 1 to 10 carbon atoms and at least one C≡C triple bond. The term "$C_5$-$C_{12}$ aryl" means an aromatic polycyclic or monocyclic hydrocarbon radical with 5-12 carbon atoms. The term "$C_5$-$C_{14}$ alalkyl" means a combination of an alkyl and an aryl with a total of 5 to 14 carbon atoms. The term "$C_5$-$C_{12}$ heteroaryl" means an aryl group where at least one carbon atom on the hydrocarbon chain normally carrying 5 to 12 carbon atoms is substituted by another atom selected from N, O, or S. The term "$C_5$ heteroaryl" therefore means an aryl group where at least 1 of the 5 carbon atoms on the hydrocarbon chain is substituted by another atom selected from N, O or S. The term "$C_1$-$C_4$ alkyloxy" means a group of formula —O(O)C—($C_1$-$C_4$ alkyl), —O(O)C—($C_4$-$C_{12}$cycloalkyl), —O(O)C—($C_4$-$C_{12}$ aryl), —O(O)C—($C_4$-$C_{12}$ arylalkyl, or —O(O)C—($C_4$-$C_{12}$ heteroaryl). Advantageously, in the compound of formula (I), such an "$C_1$-$C_4$ alkyloxy" is selected from the group of formula —O(O)C—($C_1$-$C_4$ alkyl), —O(O)C—($C_4$ cycloalkyl), —O(O)C—($C_4$ aryl) —O(O)C—($C_4$ arylalkyl), or —O(O)C—($C_4$ heteroaryl). The term "$C_1$-$C_4$ dialkylamino" means a radical of formula —N($C_1$-$C_4$ alkyl)$_2$ where each alkyl is identical or different.

The term "N-alkylamino acid" means any amino acid in which one of the hydrogen atoms in the amine group is substituted by a $C_1$-$C_{10}$ alkyl chain or a $C_5$-$C_{14}$ arylalkyl group, preferably $C_5$-$C_{10}$, namely $C_{10}$, possibly substituted. Examples of N-alkylamino acids include N-methylglycine or sarcosine, N-methylisoleucine acid, N-methylvaline acid, etc.. . . . The term "dialkylamino acid" means any amino acid in which 2 hydrogen atoms (on the central carbon or amine groups) are substituted by a $C_1$-$C_{10}$ alkyl chain or a $C_5$-$C_{14}$ arylalkyl group, preferably $C_5$-$C_{10}$, namely $C_{10}$, possibly substituted. Examples of dialkylamino acids include 2-amino-isobutyric acid (Aib), aminocyclopropane carboxylic acid, etc.

Advantageously, Z is present and therefore i=1. Also advantageously, when Z is present (i=1), then Z is a proline, possibly substituted at γ, β or δ as described previously.

In the pseudopeptide units of the compound of formula (I), $Y_1$ and $Y_2$ are selected from amino acids with a basic side chain. The term "amino acid with a basic side chain" means any natural or non-natural amino acid whose side chain R has a pKa value greater than 7 (pKa(R)>7). Thus, any amino acid can be used for $Y_1$ and $Y_2$, as long as its side chain has a pKa value greater than 7, preferably greater than 7.5, greater than 8, greater than 8.5 or greater than 9. In particular, among the natural amino acids those whose side chain has a pKa value greater than 7 include lysine (K, pKa(R)≈10.5), arginine (R, pKa(R)≈12.5), ornithine (inferior homologue of lysine, pKa (R)≈10.8), generally considered to be natural basic amino acids. Thus, in an advantageous embodiment, $Y_1$ and $Y_2$ are independently selected from arginine (R), lysine (K) and ornithine. Even more advantageously, $Y_1$ is a lysine (K) and $Y_2$ is an arginine (R). However, other non-natural amino acids can be used instead as long as the pKa value of their side chain R is greater than 7, preferably greater than 7.5, greater than 8, greater than 8.5, or greater than 9.

In the compounds of the invention, the pseudopeptide unit that is essential for binding to the RGG domain of nucleolin is the sub-unit of formula (II)

(II)

wherein $Y_1$ and $Y_2$ are as defined above. Nevertheless, the presence at one or the other end of this essential sub-unit consisting of several amino acids as defined above is not such that it would prevent binding to nucleolin. This is why the essential sub-unit of formula (II) can include at one and/or the other end 0 to 3 of any amino acids represented in the formula (I) by (X)n and (X)m respectively, where n is equal to 0 or 1 and m is an integer between 0 and 3. Advantageously, the number of the amino acids present at one and/or other end of the essential sub-unit of formula (II) is low, in other words, n is advantageously 0 and m is advantageously an integer between 0 and 2, advantageously 0 or 1, advantageously 0. Thus in an advantageous embodiment, n and m are equal to 0.

In the compounds of the invention, the sub-unit of formula (II) includes a modified peptide bond Ψ, significantly more resistant to at least one protease than a standard peptide.

The term "standard peptide bond" means an amide bond of formula (—CONH—) which is normally present between 2 amino acids in a natural protein. Such a bond is sensitive to the action of proteases. The term "modified peptide bonds Ψ" means a chemical bond between 2 amino acids of chemical formula distinct from the standard peptide bond of formula (—CONH—). This modified bond Ψ is such that it is significantly more resistant to at least one protease than a standard peptide bond of formula (—CONH—). The term "protease", also known as "peptidase" or "proteolytic enzyme", means any enzyme which cleaves the standard peptide bonds in proteins. This process is known as proteolytic cleavage. This involves the use of a water molecule which is what leads to proteases being classified as hydrolases. The proteases namely include proteases known as N-peptidases which carry out the cleavage of the N-terminal end of proteins. These proteases are particularly inconvenient in terms of the in vivo stability of peptides without modified peptide bonds. This is why pseudopeptide units of the compounds of formula (I) include a modified bond Ψ between $Y_1$ and Z (if i=1) or $Y_1$ and $Y_2$ (if i=0) such that the resistance of the sub-unit of formula (II) is significantly increased which is essential for binding to nucleolin, namely to these N-peptidases. The Ψ bond should therefore make it possible to significantly increase resistance to at least one N-peptidase. This makes it possible to significantly increase the half-life of compounds of formula (I) in vivo and in vitro. Namely, compound HB19 which has a modified bond Ψ, has a half-life of more than 24 hours in human serum or foetal calf serum at 37° C. whereas the same compound with a standard peptide bond instead of the Ψ bond only has a half-life of one hour under these same conditions.

Moreover, the inventors have found that the presence of this modified bond Ψ also makes it possible to significantly increase the efficacy of binding to nucleolin. This phenomenon may be due to the fact that this allows compound HB19 to form an irreversible complex with nucleolin.

Various chemical bonds likely to significantly increase resistance to at least one protease are known. Thus, in an advantageous embodiment, Ψ represents a reduced bond (—CH$_2$NH—) or (—CH$_2$N—) in the case where bonding takes place at the level of a secondary amine group as is the case with the bond with proline), a retro-inverso bond (—NHCO—), a methyleneoxy bond (—CH$_2$—O—), a thiomethylene bond (—CH$_2$—S—), a carba bond (—CH$_2$—CH$_2$—), a ketomethylene bond (—CO—CH$_2$—), a hydroxyethylene bond (—CHOH—CH$_2$—), a (—N—N—) bond, an E-alkene bond or a (—CH═CH—) bond. Namely, the inventors have shown that using a reduced bond (—CH$_2$—NH—) makes it possible to significantly increase resistance to at least one protease. Advantageously, Ψ therefore represents a reduced bond (—CH$_2$NH—).

Although only the Ψ between $Y_1$ and Z (if i=1) or $Y_1$ and $Y_2$ (if i=0) is systematically present in compounds of formula (I), it is also possible that other peptide bonds of the pseudopeptide units may be modified as described earlier. In particular, in the context of the invention, the bonds between the amino acids which are not specified can equally well be standard peptide bonds or modified Ψ bonds as described earlier. The presence of additional Ψ bonds may make it possible to further increase resistance to proteases of compounds of formula (I). Nevertheless, the increase linked to the presence of the first Ψ bond between $Y_1$ and Z (if i=1) or $Y_1$ and $Y_2$ (if i=0) is already highly significant and the addition of other Ψ bonds complicates synthesis of the pseudopeptide units and therefore of compounds of formula (I). The presence of additional Ψ bonds is therefore possible but optional.

Examples of compounds that can be used in the invention include in particular the compounds (see FIG. 2 and examples 1, 2, 3 and 4):

HB19 (FIG. 2A, SEQ ID NO: 5, a compound which has as a support a linear peptide of SEQ ID NO:4 in which the 5 pseudopeptide units K Ψ PR (with Ψ=CH$_2$—N) are covalently bound to the e amino group of each of the 5 lysine residues), Nucant 01 (FIG. 2B), a compound which has a support a cyclic hexapeptide consisting of alternating alanine residues (A) of configuration D and lysine residue (K) of configuration L, where the 3 pseudopeptide units K Ψ PR (with Ψ=CH$_2$—N) are covalently bound to the e amino group of each of the 3 lysine residues (K); see FIG. 2B), Nucant 2 (FIG. 2C, SEQ ID NO: 20, a compound which has as a support a linear peptide with a helicoidal structure of sequence SEQ ID NO:18 in which 5 pseudopeptide units K Ψ PR (with Ψ=CH$_2$—N) are covalently bound to the e amino group of each of the 5 lysine residues), Nucant 3 (FIG. 2D, SEQ ID NO: 21, a compound which has as a support a linear peptide with a helicoidal structure of sequence SEQ ID NO:19 in which 5 pseudopeptides K Ψ PR (with Ψ=CH$_2$—N) are covalently bound to the ε amino group of each of the 5 lysine residues), Nucant 6 (FIG. 2E, SEQ ID NO: 16, a compound which has as a support a linear peptide with a helicoidal structure of sequence SEQ ID NO:15 in which 6 pseudopeptide units K Ψ PR (with Ψ=CH$_2$—N) are covalently bound to the e amino group of each of the 6 lysine residues), Nucant 7 (FIG. 2F, SEQ ID NO: 17, a compound which has a support a linear peptide of sequence SEQ ID NO:13 in which 6 pseudopeptide units K Ψ PR (with Ψ=CH$_2$—N) are covalently bound to the ε amino group of each of the 6 lysine residues).

The compounds described above are used for the manufacture of a medication for use in the treatment of a disease involving deregulation of cell proliferation and/or angiogenesis. The term "disease involving deregulation of cell proliferation and/or angiogenesis" means, in the context of the invention, any human or animal disease affecting one or more organs in which one or more abnormal cell proliferation phenomena are observed, as well as groups of cells or tissues and/or abnormal neovascularisation. Evidently, such diseases include all types of cancer, such as adenoma, sarcoma, carcinoma, lymphoma, and especially cancer of the ovary, breast, pancreas, lymphatic ganglion, skin, blood, lung, brain, kidney, liver, nasopharyngeal cavity, thyroid, central nervous system, prostate, colon, rectum, uterine neck, testicles or bladder. They also include non-cancerous diseases of the skin such as epidermal or dermal cysts, psoriasis, angiomas, as well as ocular diseases such as age related macular degeneration (ARMD), diabetic retinopathy or neovascular glaucoma. Neurodegenerative diseases such as multiple sclerosis, Parkinson's and Alzheimer's or autoimmune diseases such as lupus or rheumatoid polyarthritis, as well as diseases related to atherosclerosis.

Advantageously, said disease involving deregulation of cell proliferation and/or angiogenesis is cancer, in particular one of those cited above.

The invention also relates to a method for screening molecules that inhibit both cell proliferation and angiogenesis, comprising:

contacting cells expressing surface nucleolin with a test molecule, and determining the capacity of said test molecule to bind to the RGG domain of nucleolin.

It is possible to produce a synthetic RGG domain of 60 amino acids of nucleolin by chemical synthesis or by using genetic engineering via the expression of its nucleic DNA sequence. Determination of the capacity of said test molecule to bind to the RGG domain of nucleolin can then be carried out by various technologies known to the man skilled in the art.

Notably, they can be carried out by measuring binding to a synthetic RGG domain of 60 amino acids using a surface plasmonic resonance technique, in particular with a Biacore® 3000 apparatus. The BIACORE® system is a biosensor using the physical principle of surface plasmonic resonance (SPR). It allows measurement in real time and without specific labelling of the kinetic constants of interaction (Ka and Kd) between two molecules on a biospecific surface. To this end, one of the molecules (ligand) is immobilized on the sensor surface and the other (analyte) is injected. The principle of detection by SPR is quantification of changes in the refractive index close to the surface, linked to variations in the mass on the surface of the biosensor resulting from the formation and dissociation of molecular complexes. When monochromatic, polarized light arrives at the interface between two media with different refractive indexes and this interface is coated with a fine layer of metal, the intensity of reflected light is clearly reduced for a particular incidence angle. This results from the fact that one electromagnetic component of light, the evanescent wave, is propagated perpendicularly to the interface, up to 1 μm. The resonance angles varies, namely as a function of the weight of molecules located near the surface. Consequently, monitoring of the SPR angle as a function of time makes it possible to observe association and dissociation of the ligand and analyte in real time. The signal obtained is recorded (sensogram). It is quantified in resonance units (RU). A change of 1000 RU corresponds to a 0.1° shift in the angle and is equivalent to binding of 1 ng of protein per mm$^2$. This technology therefore makes it possible not only to establish the capacity of the test molecule to bind to the RGG domain but also the efficacy of binding (affinity constant) of said molecule to the RGG domain of nucleolin.

It is also possible to generate a synthetic RGG domain labelled with biotin or fused to a peptide or protein such as GST (Glutathione S-transferase). The presence of biotin or GST then makes it possible to detect, by means of a labelled avidine/streptavidine ligand (fluorescent, luminescent, radioactive, etc.), whether the RGG domain is biotinylated and/or if there are anti-GST antibodies if the RGG domain is fused with GST. Although less accurate, these technologies allow faster and easier screening of a larger number of molecules for their capacity to bind to the RGG domain of nucleolin, after which more precise determination of the efficacy of binding to the RGG domain of nucleolin can be carried out using the previously mentioned surface plasmonic resonance technique.

Thus, it is preferable to firstly carry out quick and easy screening of the capacity to bind to RGG domain of nucleolin. Next, the analysis is refined by determining the efficacy of binding to the RGG domain of candidates capable of binding to the RGG domain by the surface plasmonic resonance technique. However, in the case where only a small number of compounds are to be tested, their efficacy of binding to the RGG domain can be measured directly using the surface plasmonic resonance technique.

The invention further relates to a compound as defined earlier, with the exception of compounds whose support is a non-cyclic peptide including an amino acid sequence selected from KPG, KGP, KGC, or KX$_1$KX$_4$KX$_1$K, where X$_1$ is optional and selected from lysine (K), valine (V), alanine (A), glutamic acid (E) and isoleucine (I), and X$_4$ is optional and selected from valine (V), alanine (A), glutamic acid (E) and isoleucine (I).

Notably, the support (with the exception of those excluded in the preceding paragraph), the manner in which the pseudopeptide units are grafted on the support and amino acids X, Y$_1$ and Y$_2$, n and m, or Y can be in the form of any previously-described embodiment.

The invention also relates to a compound as described earlier with the exception of compounds whose support is a linear peptide. In particular, the support (with the exception of linear peptides), the manner in which the pseudopeptide units are grafted on the support and amino acids X, Y$_1$ and Y$_2$, n and m, or Y can be in the form of any previously-described embodiment.

Notably, the support can be selected from a linear peptide comprising an amino acid sequence selected from Aib-K-Aib-G (SEQ ID NO: 6) or K-Aib-G (SEQ ID NO: 7), a cyclic peptide, a linear or cyclic peptoid, a foldamer, a linear polymer or spherical dendrimer, a sugar or a nanoparticle.

In some advantageous cases, the support can be a linear peptide consisting of an amino acid sequence selected from SEQ ID NO: 8 and SEQ ID NO: 9, SEQ ID NO: 14, SEQ ID NO: 15, SEQ ID NO:18, and SEQ ID NO:19.

The compounds according to the invention can include, in particular, compounds whose support is a cyclic peptide such as Nucant 01 (FIG. 2B), or a linear peptide with a helicoidal structure such as Nucant 2 (SEQ ID NO: 20 and FIG. 2C) and Nucant 3 (SEQ ID NO: 21 and FIG. 2D), described earlier. They can also include the compound Nucant 6 (SEQ ID NO: 16, see example 4 and figure E).

The invention also relates to the compound Nucant 7 (SEQ ID NO: 17 and FIG. 2F) as the compound.

The invention further relates to a compound as defined earlier, with the exception of compounds whose support is a non-cyclic peptide including an amino acid sequence selected from KPG, KGP, KGC, or $KX_1KX_4KX_1K$, where $X_1$ is optional and selected from lysine (K), valine (V), alanine (A), glutamic acid (E) and isoleucine (I), and $X_4$ is optional and selected from valine (V), alanine (A), glutamic acid (E) and isoleucine (I).

Notably, the support (with the exception of those excluded in the preceding paragraph), the manner in which the pseudopeptide units are grafted on the support and amino acids X, $Y_1$ and $Y_2$, n and m, or Y can be in the form of any previously-described embodiment.

The invention also relates to a compound as described earlier with the exception of compounds whose support is a linear peptide for use as medication. In particular, the support (with the exception of linear peptides), the manner in which the pseudopeptide units are grafted on the support and amino acids X, $Y_1$ and $Y_2$, n and m, or Y can be in the form of any previously-described embodiment.

Notably, the support can be selected from a linear peptide comprised of an amino acid sequence selected from Aib-K-Aib-G (SEQ ID NO: 6) or K-Aib-G (SEQ ID NO: 7), a cyclic peptide, linear or cyclic peptoid, foldamer, linear polymer or spherical dendrimer, sugar or nanoparticle.

In some advantageous cases, the support can be a linear peptide consisting of an amino acid sequence selected from SEQ ID NO: 8 and SEQ ID NO: 9, SEQ ID NO: 14, SEQ ID NO: 15, SEQ ID NO:18, and SEQ ID NO: 19.

Such compounds, for use as medication, particularly include compounds whose support is a cyclic peptide such as Nucant 01 (FIG. 2B), or a linear peptide with a helicoidal structure such as Nucant 2 (SEQ ID NO: 20 et FIG. 2C) and Nucant 3 (SEQ ID NO: 21 and FIG. 2D), described earlier. They can also include the compound Nucant 6 (SEQ ID NO: 16, see example 4 and FIG. 2E).

The invention also relates to the compound Nucant 7 (SEQ ID NO: 17 and FIG. 2F) for use as medication.

The invention further relates to a pharmaceutical composition comprising a compound as defined earlier, with the exception of compounds whose support is a non-cyclic peptide including an amino acid sequence selected from KPG, KGP, KGC, or $KX_1KX_4KX_1K$, where $X_1$ is optional and selected from lysine (K), valine (V), alanine (A), glutamic acid (E) and isoleucine (I), and $X_4$ is optional and selected from valine (V), alanine (A), glutamic acid (E) and isoleucine (I).

Notably, the support (with the exception of those excluded in the preceding paragraph), the manner in which the pseudopeptide units are grafted on the support and amino acids X, $Y_1$ and $Y_2$, n and m, or Y can be in the form of any previously-described embodiment.

The invention also relates to a pharmaceutical composition as described earlier with the exception of compounds whose support is a linear peptide. In particular, the support (with the exception of linear peptides), the manner in which the pseudopeptide units are grafted on the support and amino acids X, $Y_1$ and $Y_2$, n and m, or Y can be in the form of any previously-described embodiment.

Notably, the support can be selected from a linear peptide comprised of an amino acid sequence selected from Aib-K-Aib-G (SEQ ID NO: 6) or K-Aib-G (SEQ ID NO: 7), a cyclic peptide, linear or cyclic peptoid, foldamer, linear polymer or spherical dendrimer, sugar or nanoparticle.

In some advantageous cases, the support can be a linear peptide consisting of an amino acid sequence selected from SEQ ID NO: 8 and SEQ ID NO: 9, SEQ ID NO: 14, SEQ ID NO: 15, SEQ ID NO:18, and SEQ ID NO:19.

The pharmaceutical compositions according to the invention can include, in particular, compounds whose support is a cyclic peptide such as Nucant 01 (FIG. 2B), or a linear peptide with a helicoidal structure such as Nucant 2 (SEQ ID NO: 20 et FIG. 2C) and Nucant 3 (SEQ ID NO: 21 and FIG. 2D), described earlier. They can also include the compound Nucant 6 (SEQ ID NO: 16, see example 4 and FIG. 2E).

The invention also relates to a pharmaceutical composition containing the compound Nucant 7 (SEQ ID NO: 17 and FIG. 2F).

Such pharmaceutical compositions combine the compound(s) according to the invention with a pharmaceutically acceptable support.

This invention also relates to the use of a synthetic multivalent compound including or consisting of a support on which at least 3 pseudopeptide units are grafted, said compound being of formula (I):

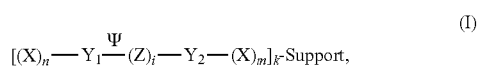

$$[(X)_n \!-\! Y_1 \!\overset{\Psi}{-}\! (Z)_i \!-\! Y_2 \!-\! (X)_m]_k\text{-Support},\qquad (I)$$

wherein each X independently represents any amino acid; $Y_1$ and $Y_2$ are independently selected from basic side chain amino acids; Z is selected from proline, possibly substituted at γ, β or δ; a natural or non N-alkylamino acid; dialkylamino acid; cyclic dialkylamino acid; pipecolic acid or derivatives thereof; n and i are independently 0 or 1; m is an integer between 0 and 3; k is an integer greater than or equal to 3 and Ψ represents a modified peptide bond, significantly more resistant to at least one protease than a standard peptide bond, for the manufacture of a medication intended for the treatment of inflammatory diseases.

It is now well-established that chronic inflammatory diseases, namely autoimmune diseases with cellular mediation, are partly triggered by cytokines. Results obtained with various experimental animal models have revealed the role played by cytokines in the pathogenesis of disease (17). For example, proinflammatory cytokines such as tumour necrosis factor α (TNF-α), interleukin 1(IL-1), IL-6, IL-15 and IL-18 regulate the immune and inflammatory responses in patients with rheumatoid polyarthritis. In particular, TNF-α and IL-1β promote the destruction of cartilage and bone marrow.

Moreover, in the course of the inflammatory process, the vascular endothelium expresses different chemokines and adhesion molecules which participate in the recruitment of leukocytes in the inflammatory focus (18).

IL-8 is a C—X—C chemokine which triggers the activation and selective recruitment of leukocytes in tissues which are the site of inflammation. When high levels are expressed, IL-8 can have pathological consequences for the body. Lipopolysaccharide (LPS) and proinflammatory cytokines such as TNF-α and IL-1 trigger the secretion of IL-8 by many cell types, particularly endothelial cells (19).

Intercellular Adhesion Molecule-1 (ICAM-1) is an immunoglobulin type protein expressed at the surface of several cell types including endothelial cells and cells involved in the immune response. It plays an important role in the adhesion and migration of leukocytes to the sites of inflammation (20).

Proinflammatory cytokines are also involved in the general inflammatory response (septic shock) triggered by bacterial infections. Lipopolysaccharide (LPS) is an integral component of the external membrane of gram-negative bacteria. This immuno-stimulating molecule is a factor which largely contributes to triggering the general inflammatory response, called septic shock, which often accompanies gram-negative bacterial infections. LPS has the biological property of stimulating the production of cytokines, such as TNF-α, IL-1 and IL-6, by the lymphoreticular cells. The induction of these cytokines plays a pivotal role in the development of septic syndrome because the administration of TNF-α alone can lead to a septic condition and death since TNF-α can trigger the production of IL-1 and IL-6 in vivo. Moreover, in animal models, pretreatment with anti-TNF-α antibodies and the IL-1 receptor agonist makes it possible to protect animals against the lethal effects of LPS (21).

Severe septicaemia is associated with an aggressive inflammatory reaction and organ deficiencies. It is frequently linked to a high mortality rate. It can follow on from a bacterial, fungal or viral infection. This reaction is marked by sequential secretion of proinflammatory then inflammatory cytokines. TNF-α and IL-β are among the most proinflammatory cytokines. Up until now, no clinical trials involving anti-LPS or anti-cytokine reagents have met with success (22, 23).

The proinflammatory cytokines also appear to play a physiopathological role in patients with carditis or inflammation of the heart, which manifests itself in the form of inflammation of the endocardium (endocarditis) or pericardium (pericarditis) or cardiac muscle (myocarditis). For example, serum levels of IL-6 are significantly higher in patients with infectious endocarditis which can be caused, in particular, by a *Staphylococcus aureus* infection. In this way, high IL-6 levels in the serum can suggest the existence of infectious pericarditis and can be used as a tool for the diagnosis and follow-up of treatment for this disease (24, 25)

In view of the important of the role of proinflammatory cytokines such as TNF-α, IL-1 and IL-6 in inflammatory disease, anti-inflammatory cytokine therapies which involve anti-TNF-α, anti-IL-1 and anti-IL-6 reagents have been developed for the treatment of patients suffering from inflammatory diseases (26).

Various clinical trials involving anti-inflammatory cytokine reagents in the treatment of chronic inflammatory diseases, such as rheumatoid arthritis and abdominal inflammatory disease, have met with some success: Etanercept (TNF receptor-P75 Fc fusion protein), Infliximab (chimeric human anti-TNF-α monoclonal antibody), Adalimumab (recombinant human anti-TNF-α monoclonal antibody) and Anakinra (recombinant form of human IL-1β receptor antagonist)(22).

Nevertheless, all the anti-inflammatory cytokine reagents available to date are proteins and thus present the disadvantages associated with protein medications, in particular, the high cost of production and problems linked to large-scale production.

Consequently, there is a real need for low molecular weight molecules capable of specifically targeting the synthesis pathways of proinflammatory cytokines.

Surprisingly, the inventors have found that compounds of formula (I), such as those described earlier, have anti-inflammatory activity; in particular, they inhibit the production of TNF-α, IL-6 and IL-8 as well as the expression of ICAM-1 by various cell types stimulated by LPS. These compounds are extremely interesting because, as mentioned earlier:

no toxic effect of these compounds has been observed by the inventor, neither in vitro nor in vivo;

these compounds are easy to synthesize, even on an industrial scale, under easily controlled conditions;

these compounds have sufficient in vivo bioavailability of themselves not to need a particular pharmaceutical form to be developed.

The invention thus relates to the use of a synthetic multivalent compound of formula (I), as defined earlier in any of the embodiments described above, for the preparation of a medication intended for the treatment of inflammatory diseases.

In particular, in formula (I), the support, the number of pseudopeptide units k, the manner in which the pseudopeptide units are grafted on the support, the amino acids X, Y1 and Y2; n and m, or Ψ can be in the form of any embodiment described above.

The term <<inflammatory disease>> means any disease in which an inflammatory reaction has pathological consequences for the organism. In particular, inflammatory diseases in the context of the invention include autoimmune diseases (such as lupus or rheumatoid polyarthritis), septicaemia, septic shock, cardiac inflammatory diseases (carditis, and especially endocarditis, pericarditis, myocarditis, in particular those of an infectious origin such as those caused by *Staphylococcus aureus*), graft rejection, trauma, inflammatory diseases of the joints (notably, different forms of arthritis), inflammatory diseases of the gastrointestinal system (notably, colitis, enteritis, gastritis, gastroenteritis, and chronic inflammatory diseases of the intestine such as Crohn's disease and haemorrhagic rectocolitis (HRC)), inflammatory diseases of the skin (eczema, allergic contact dermatitis, psoriasis, dermatosis), inflammatory diseases of the respiratory system, especially chronic obstructive pulmonary disease (COPD), and allergies.

In an advantageous embodiment, the inflammatory disease is an autoimmune disease, in particular lupus or rheumatoid arthritis. In another advantageous embodiment, the inflammatory disease is septic shock. In yet another advantageous embodiment, the inflammatory disease is an endocarditis, particularly endocarditis of infectious origin, such as that caused by *Staphylococcus aureus*.

The advantages of this invention are illustrated in the figures and examples given below.

EXAMPLES

Anti-Tumour Activity of Pentavalent Compound HB19

Effect of pentavalent compound HB19 on the growth of tumour cells in vitro

Figure 3:
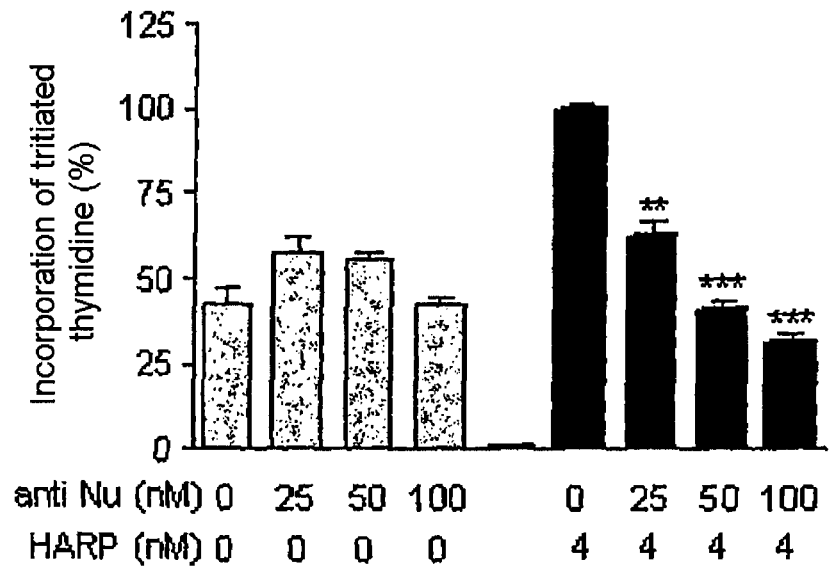
FIG. 3. Effect of A. anti-nucleolin (anti Nu), B. isotypical IgG, C. peptide F3, and D. HB-19 on the proliferation of NIH-3T3 cells stimulated by HARP. Quiescent NIH-3T3 cells are stimulated or not by 4 nM of HARP in the presence or not of HB19 at the concentrations indicated. After 24 hours of incubation, cell proliferation was determined by measuring the incorporation of tritiated thymidine. The results are given as a percentage with respect to the control stimulated by HARP (100%). MSD (threshold), (p<0.01 and *p<0.001).
Figure 3:
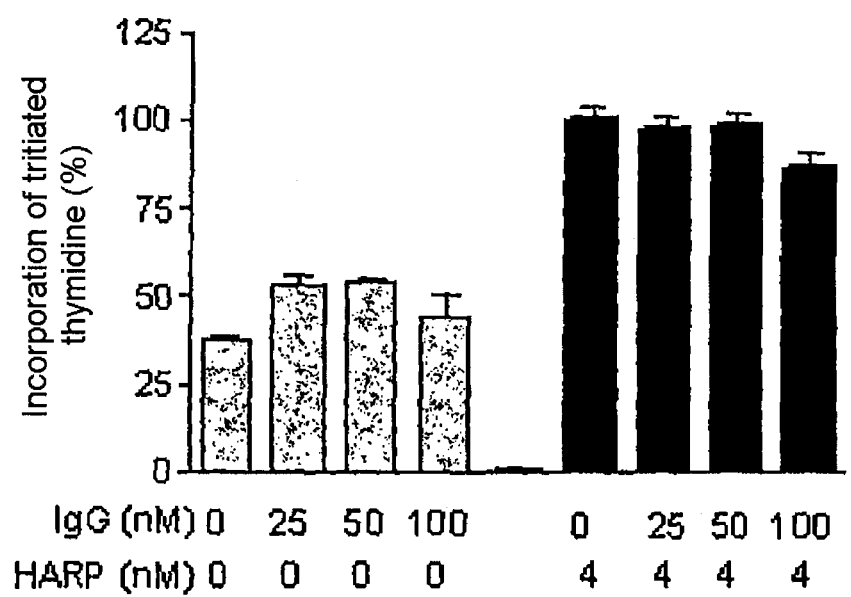
Figure 3:
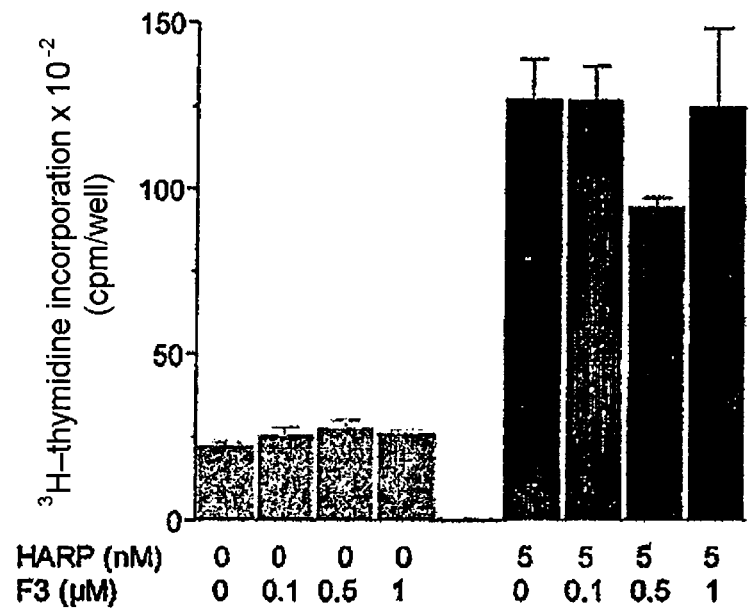
Figure 3:
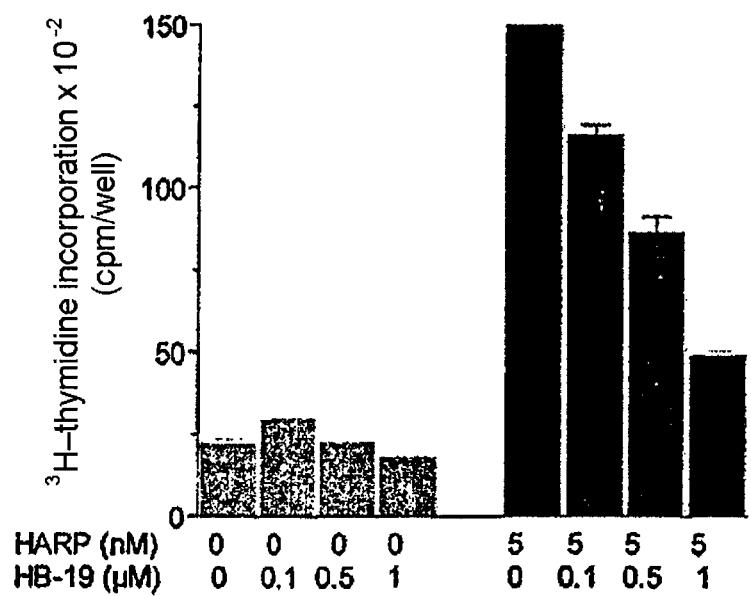

Role of Surface Nucleolin in Anchorage-Dependent Cell Proliferation and Inhibitory Effect of HB-19 on this Proliferation The role played by nucleolin in the biological activity of the HARP molecule was studied in a series of experiments: the mitogenic activity of HARP, tested by measuring the incorporation of tritiated thymidine by NIH 3T3 cells, was evaluated in the presence or absence of a monoclonal antibody which specifically recognizes nucleolin. The results show that this antibody inhibits the mitogenic activity of HARP in NIH 3T3 cells in a dose-dependent manner (FIG. 3A).

The addition of 50 nM of anti-nucleolin antibody completely inhibits mitogenic activity resulting from 4 nM of HARP whereas non-specific antibodies against nucleolin of the same isotype have no effect on proliferation induced by HARP. This is the case whatever the immunoglobulin concentration used, thus demonstrating the specificity of the inhibition observed (FIG. 3B).

Peptide F3 and compound HB19 are two ligands of nucleolin. Peptide F3 binds to the N-terminal part of nucleolin which contains many acid amino acid regions (9), contrary to compound HB19 which binds to the RGG domain located in the C-terminal part of nucleolin (see FIG. 1). It has also been shown that specific binding of compound HB19 to the surface of cells is not affected by the presence of peptide F3 (experiment conducted by the inventors using FACS).

The inventors investigated whether peptide F3 and pentavalent compound HB19 were capable of inhibiting cell proliferation of NIH-3T3 cells triggered by the growth factor HARP. In the same series of experiments, the effects of compound HB19 and peptide F3, which specifically bind to surface nucleolin, were therefore tested.

The results for peptide F3 are given in 1a FIG. 3C and unequivocally show that peptide F3, like IgG antibodies, does not lead to inhibition of NIH 3T3 proliferation triggered by HARP.

The results for HB19 are given in FIG. 3D and show that HB-19 leads to dose-dependent inhibition of NIH 3T3 proliferation triggered by HARP. Addition of 0.5 µM of HB-19 leads to 81% inhibition of the effect triggered by 4 nM of HARP. This clearly shows that it is not enough to have a nucleolin ligand capable of being internalised to bring about inhibition of proliferation and suggests that, in order to be effective, a nucleolin ligand needs to be multivalent and bind to one or more RGG units in the C-terminal domain of one or more nucleolin molecules.

Figure 4:
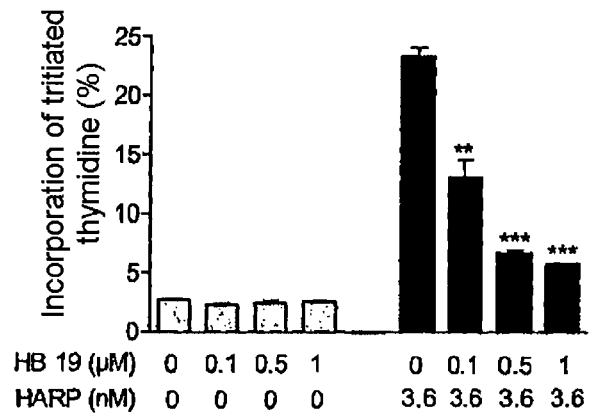
FIG. 4. Effect of pretreatment of NIH-3T3 cells with HB19 for one hour on proliferation induced by HARP. NIH-3T3 cells were treated with HB19 for one hour then washed and stimulated or not by 3.6 nM of HARP. After 24 hours of incubation, cell proliferation was determined by measuring the incorporation of tritiated thymidine. The results are given as a percentage with respect to the control stimulated by HARP (100%). MSD (threshold), (p<0.01 and *p<0.001).

Moreover, it is interesting to note that comparable inhibition is observed when cells are pretreated for one hour with varying concentration of HB-19, washed then stimulated by HARP (FIG. 4). This result shows that HB-19 binds to surface nucleolin present on NIH 3T3, thus blocking cell proliferation induced by HARP one hour later.

In order to study whether the effect of HB-19 on the inhibition of cell proliferation is specific for a given growth factor such as HARP, two series of experiments were carried out which consisted in studying the effect of HB-19 on NIH 3T3 cells stimulated by:

FGF-2, another growth factor, or

5% foetal calf serum containing a mixture of various growth factors.

Figure 5:
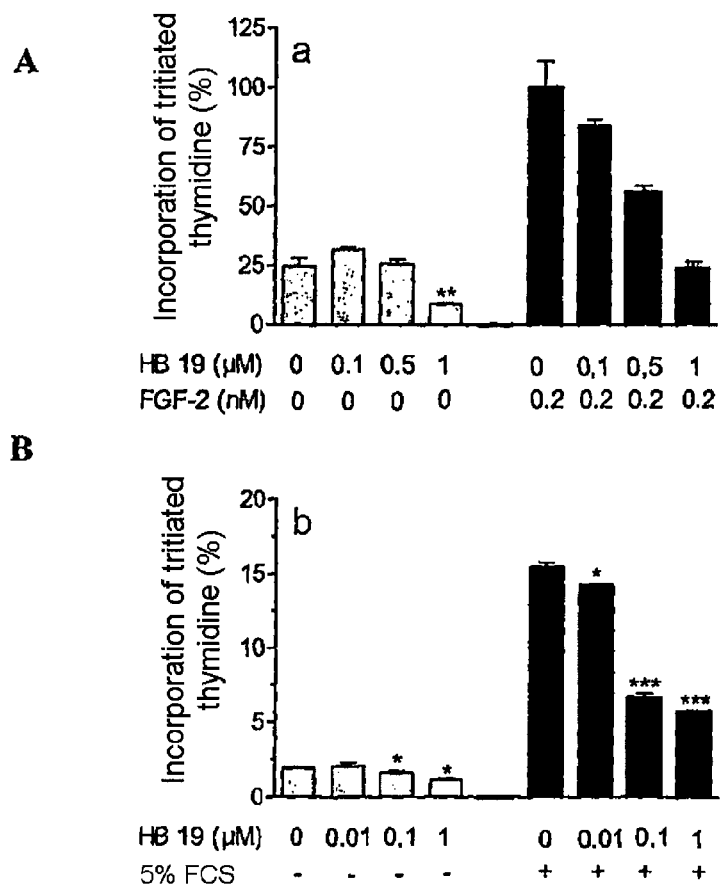
FIG. 5. Effect of HB-19 on the proliferation of NIH-3T3 cells stimulated by 0.2 nM FGF-2 (A) or by 5% foetal calf serum (B). Quiescent NIH-3T3 cells are stimulated by FGF-2 or by 5% serum in the presence or not of HB19 at the concentrations indicated. After 24 hours of incubation, cell proliferation was determined by measuring the incorporation of tritiated thymidine. The results are given as a percentage with respect to the control stimulated by HARP (100%). MSD (threshold), (p<0.01 and *p<0.001).

The results of these experiments are presented in FIG. 5 and show that HB-19 at a concentration de 0.5 µM is capable of inhibiting the proliferation of cells stimulated by FGF-2 (A) or by foetal calf serum (B).

Thus, the results show that overall, HB-19 is capable of in vitro inhibition of the proliferation of tumour cells. This is the case whatever the agent used to trigger cell proliferation.

Role of Nucleolin in Anchorage-Dependent Cell Proliferation and Inhibitory Effect of HB-19 on this Proliferation In parallel to these studies on cell proliferation, the role of nucleolin on anchorage-independent growth, the phenotype characteristic of transformed cells, was tested in a growth model on wet agar using the human mammary carcinoma line, MDA-MB-231, as well as a mouse melanoma line, B16-BL6.

Figure 6:
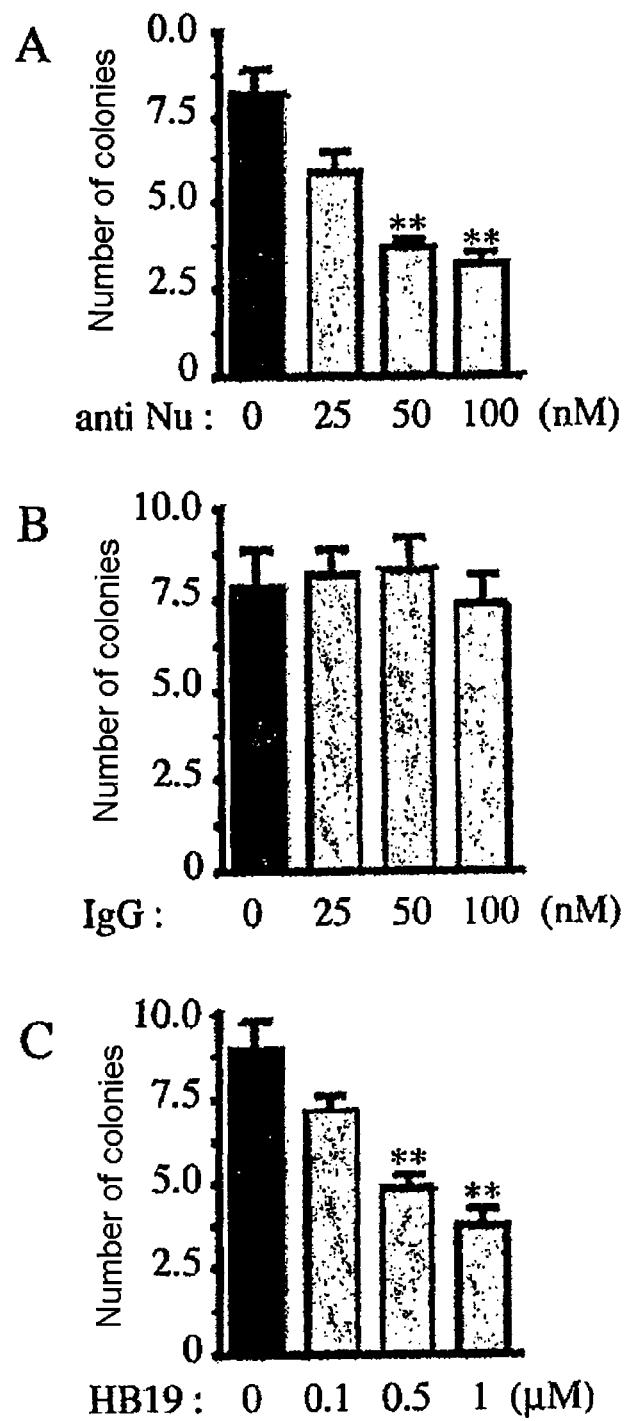
FIG. 6. Effect of anti-nucleolin (anti Nu) (A), isotype IgG (B) and HB-19 (C) on MDA-MB231 growth on wet agar. MDA-MB231 cells are cultured in a culture medium with 0.35% agar on a 0.6% agar matrix. After 10 days in culture, colonies with a diameter greater than 50 μm were counted. 5 areas per well and each point in triplicate, (**p<0.01).

In these experiments, cells were cultured on agar gel in the presence or absence of varying concentrations of the control anti-nucleolin antibodies, control immunoglobulins or compound HB-19. After 10 days of incubation at 37° C., the number of colonies present in each culture plate was counted. As shown in FIG. 6, the number of colonies fell by 60% for cultures treated with 0.1 µM anti-nucleolin (A) whereas no effect was found when cultures were treated with immunoglobulins of the same isotype (B).

More especially, inhibition of the number of colonies with respect to the control was also found for cultures treated with HB-19 and this in a dose-dependent manner. A 59% decrease in the number of colonies in cultures treated with 1 µM of HB-19 (FIG. 6C) was observed.

Figure 7:
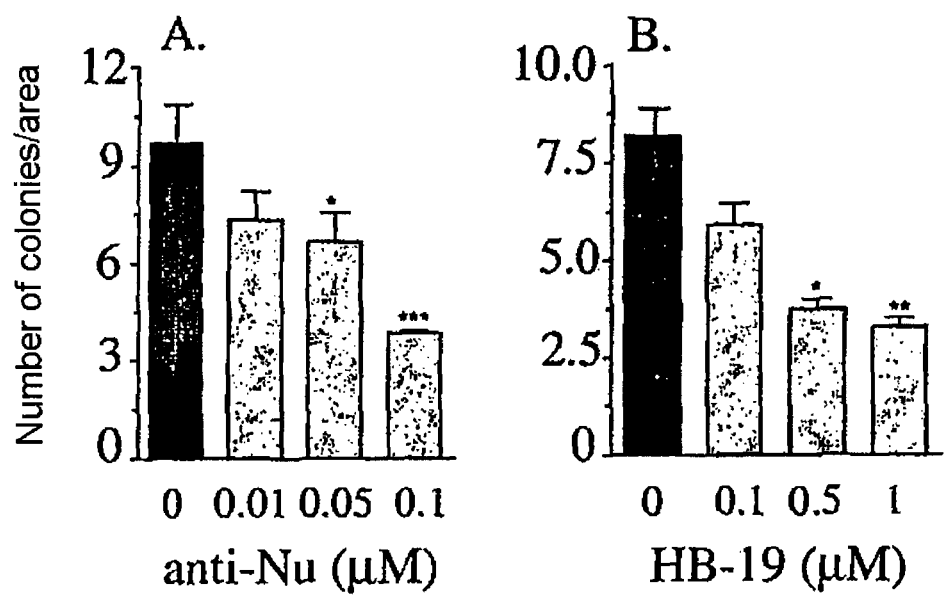
FIG. 7. Effect of anti-nucleolin (anti Nu) (A), and HB-19 (B) on B16-BL6 growth on wet agar. B16-BL6 cells are cultured in a culture medium with 0.35% agar on a 0.6% agar matrix. After 10 days in culture, colonies with a diameter greater than 50 μm were counted. 5 areas per well and each point in triplicate, (*p<0.05 and **p<0.01).

Similar results were obtained using murine melanomas such as B16-BL6 as target cells. The results are presented in FIG. 7. Examination of the results shows that both anti-nucleolin antibodies (A) and the molecule HB-19 (B) inhibit the growth of B16-BL6 on wet agar in a dose-dependent manner Inhibition in excess of 50% of the number of clones is observed in the presence of 1 µM of HB-19.

This set of results demonstrates that the compound HB-19 has an inhibitory effect on anchorage-independent cell growth. This is true of both cell models: human mammary carcinomas and mouse melanomas.

Effect of Pentavalent Compound HB19 on Angiogenesis Triggered by Angiogenic Factors Given that surface nucleolin is present at the surface of activated endothelial cells (9), the effect of HB-19 on the differentiation of endothelial cells was tested.

Firstly, this effect was tested on the in vitro proliferation of endothelial cells (HUVEC: Human umbilical vein endothelial cells). 20000 HUVEC cells per well were cultured and compound HB19 was added in different concentrations on each day. Cells were counted after 6 days of treatment. The results are given in FIG. 8A and show that, contrary to the anti-nucleolin polyclonal antibody preparation used in the article by Huang et al. (16), HB19 leads to inhibition of the proliferation of endothelial cells.

The effect of the presence of HB19 (1 µM) on the differentiation of HUVEC cells in a three-dimensional collagen gel cultured in the presence of HARP angiogens (1 nM), VEGF (1 nM) and FGF-2 (3 nM) were also tested. After 4 days, tubular network structures were counted. The results are presented in arbitrary units in FIG. 8B and show that HB19 also inhibits the differentiation of HUVEC cells in a three-dimensional collagen gel cultured in the presence of angiogenic factors.

Finally, the effect of HB-19 on the differentiation of endothelial cells was tested in an in vivo angiogenesis model. This test mimics the first stages of the process leading to the formation of blood vessels.

Figure 8:
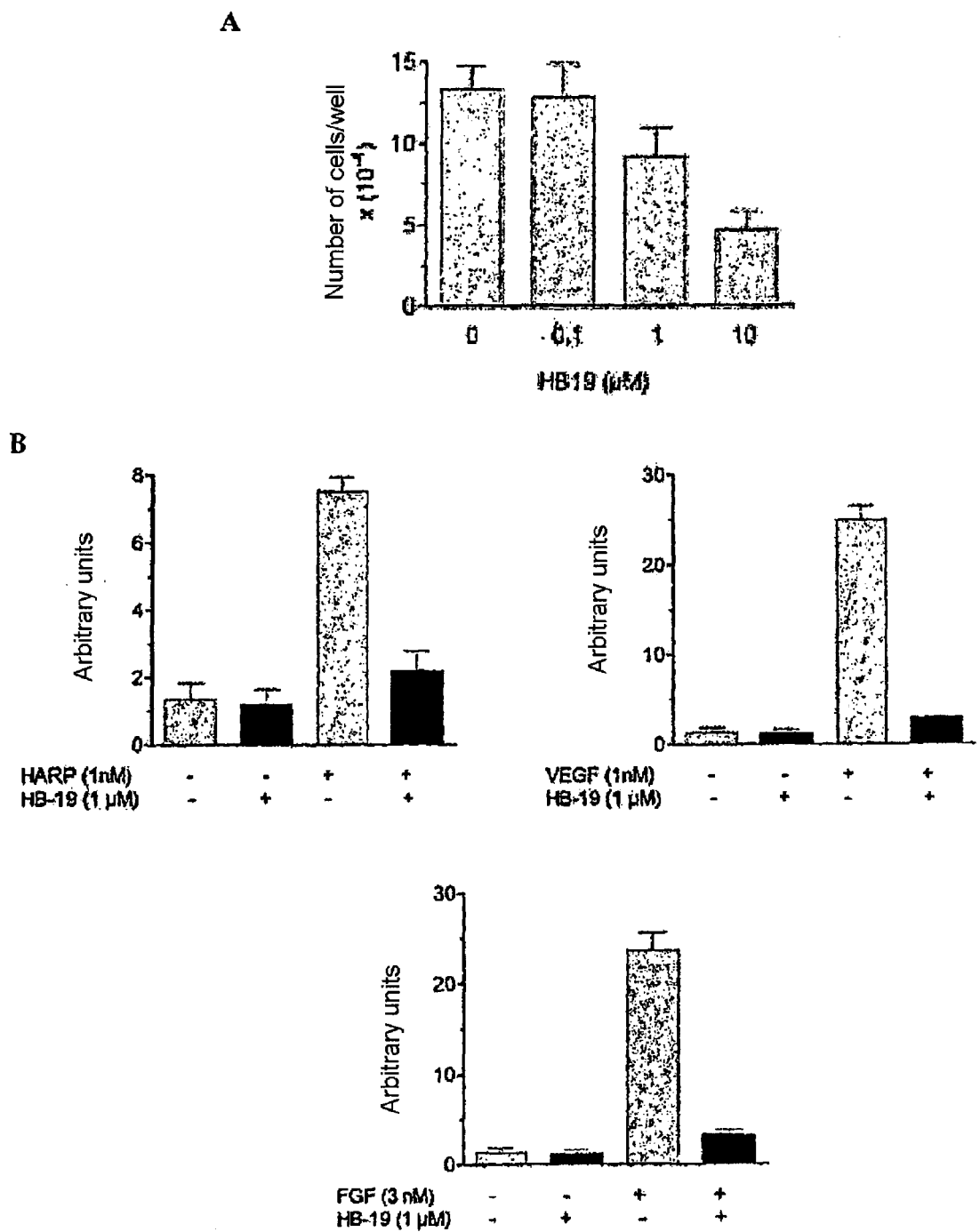
FIG. 8. Effect of HB-19 on angiogenesis. A. Effect of HB19 tested on in vitro proliferation of HUVEC cells. 20000 HUVEC cells were cultured in wells and compound HB19 was added in different concentrations on each day. Cells were counted after 6 days of treatment. B. Effect of HB19 (1 μM) on the differentiation of HUVEC cells in a three-dimensional collagen gel cultured in the presence of HARP angiogenic factors (1 nM); VEGF (1 nM) and FGF-2 (3 nM) were also tested. After 4 days, tubular network structures were counted. The results are presented in arbitrary units. C. Effect of HB-19 on angiogenesis triggered HARP or FGF-2 in an in vivo angiogenesis model (/matrigel <<plug assay>>). Matrigel (300 μl) containing the indicated molecules is injected subcutaneously into mice. Mice were sacrificed after one week and matrigel was removed. 8 μm thick cuts were performed. After staining, the number of endothelial cells is estimated by image analysis. For each matrigel, 5 cuts and 4 mice were analysed per experimental point.
Figure 8:
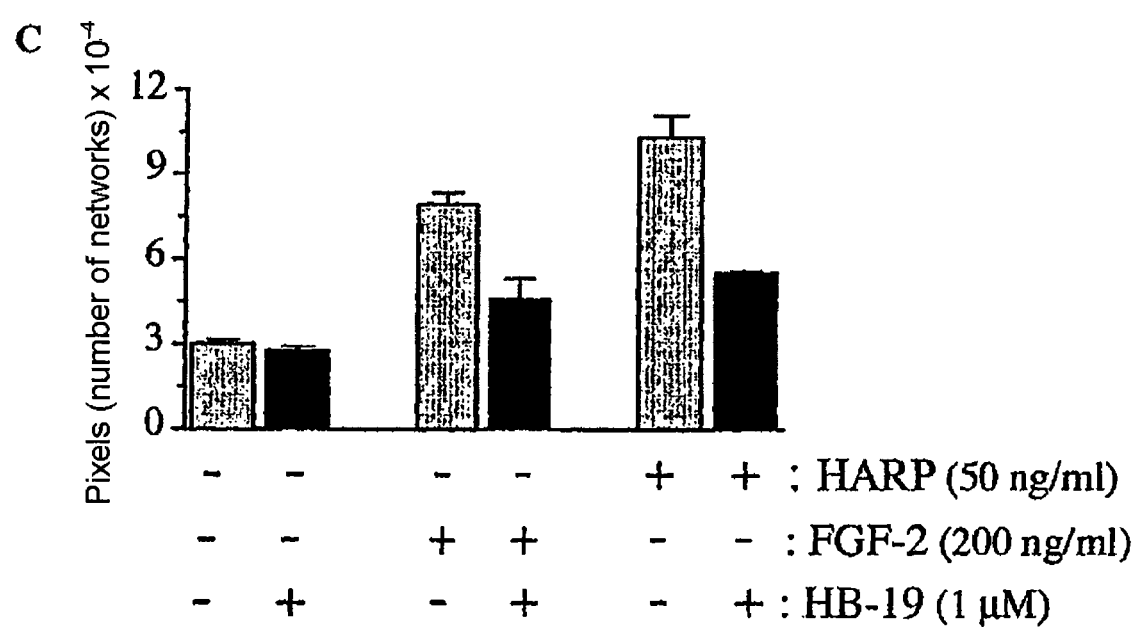

This experimental model of angiogenesis consists in subcutaneously injecting mice with matrigel containing the substance to be analysed for its angiogenesis stimulating or inhibiting properties. Matrigel was removed one week later, histological cuts were taken and the number of endothelial cells (CD31+, factor VIII+) was quantified by image analysis after immunohistochemistry. As can be seen in FIG. 8, HB-19 alone has no effect on the recruitment of endothelial cells in matrigel. On the other hand, it inhibits angiogenesis triggered by HARP or FGF-2.

Analysis of the results shows that HB-19 is capable of inhibiting angiogenesis triggered by proangiogenic factors such as FGF-2 or HARP. This shows a general angiostatic effect of HB-19 specifically targeting endothelial cells involved in angiogenesis.

Thus, compound HB19 drastically inhibits the proliferation and differentiation of HUVEC cells triggered by HARP, VEGF and FGF-2. It therefore has a much more pronounced effect than the anti-nucleolin monoclonal antibodies used in the article by Huang et al. (16).

There are several advantages to using endothelial cells as an anticancer target cell. Contrary to tumour cells presenting genetic instability, endothelial stable are extremely stable genetically, thus limiting the mechanisms of resistance. In addition, since the molecular target is surface nucleolin, HB-19 principally targets activated endothelial cells and therefore those that have entered the neo-angiogenesis phase. It should be noted that the tumoral endothelial cell divide 70 times more quickly than normal endothelial cells, which is why tumoral endothelial cells are a major target, thus limiting potential side effects.

In Vivo Anti-Tumour Effect of Pentavalent Compound HB19

The effect of pentavalent compound HB-19 on tumour growth in vivo was tested in a tumour growth model in athymic mice. In this experiment, the target cells originated from cancers of the human mammary glands: MDA-MB231.

Groups of 4 athymic mice (nude/nude) were injected in the flank with $2\times10^6$ cells. When tumour volume reached at least 200 mm$^3$, mice were either treated or not by injection in the tumour (peritumoral or subcutaneous route) of 100 µl every two days of a PBS solution (control group) or HB-19 solution (5 mg/kg) or a commonly used clinical agent, tamoxifen (also called taxol, 10 mg/kg). Tumour size was measured on days 7, 14, 21, 28, 34 and 40 using a calliper.

The results are presented in FIG. 8 and show that the peptide HB-19, used at a dose of 5 mg/kg, leads to inhibition of tumour growth with respect to untreated control mice which had a ×7 larger tumour size.

Figure 9:
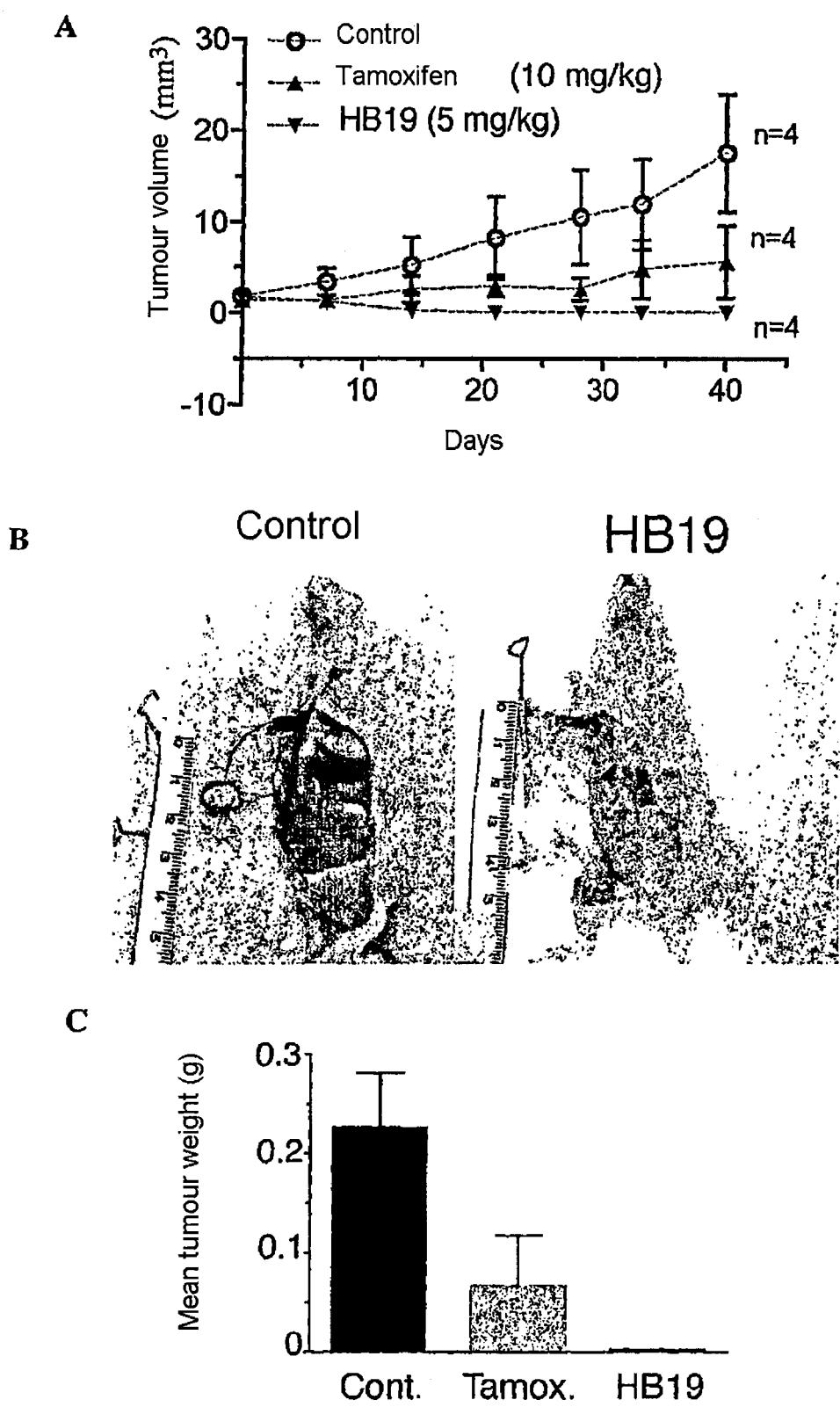
FIG. 9. Effect of HB-19 on tumour growth in an MDA-MB231 xenograft model. Human mammary carcinoma MDA-MB231 cells were injected subcutaneously athymic mice (nude). When the tumour reached a volume of 200 mm$^3$, mice were treated by subcutaneous route as shown in graph in A. B. Observation and measurement of tumours in mice sacrificed at day 40. C. Tumour weight in mice sacrificed at day 40.

Moreover, whereas tumour volume in mice treated with tamoxifen did not change in a significant manner from the start of treatment, tumours in mice treated with HB-19 were undetectable after 21 days of treatment (FIG. 9A). Although tamoxfen at 10 mg/kg only leads to stabilisation of tumour volume or partial regression, pentavalent compound HB-19 at 5 mg/kg actually leads to apparently total tumour regression.

In order to control these results, mice were sacrificed after 40 days of treatment and tumours were removed then weighed. Average weight of tumours in untreated mice was 0.22 g (distribution 0.083-0.34 g), 0.06 g in those treated with tamoxifen 10 mg/kg (distribution 0.006-0.22 g) and no tumours were found in mice treated with HB-19 (FIGS. 9B and C), thus confirming the estimation of tumour volume carried out by extracorporeal measurement of size.

Figure 10:
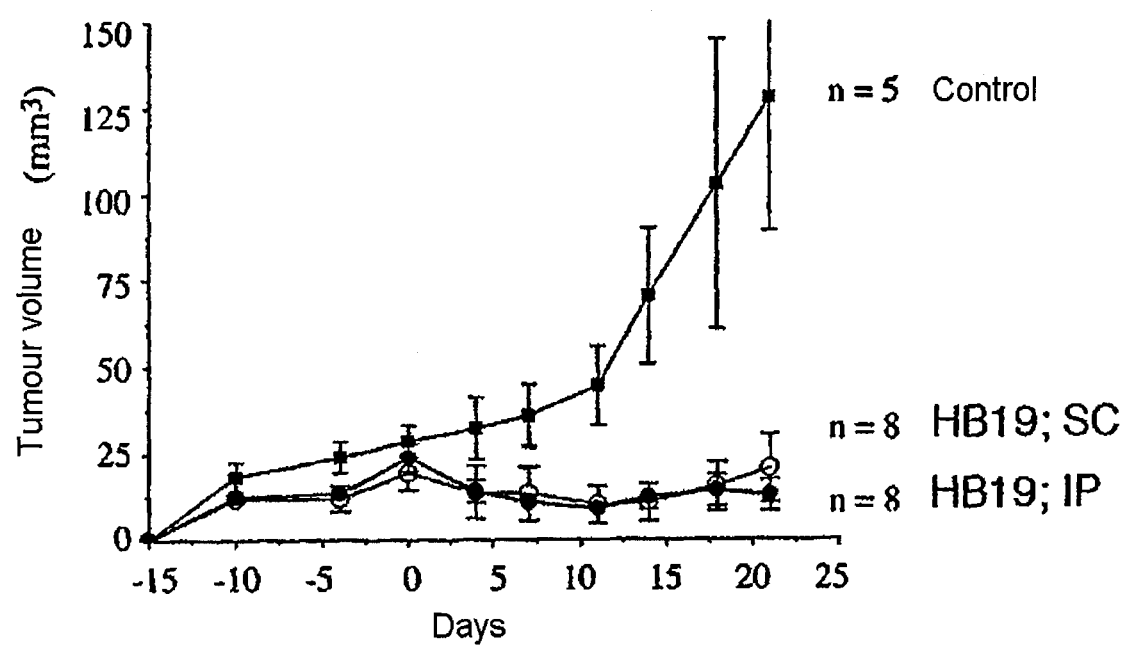
FIG. 10. Effect of HB-19 on tumour growth in an MDA-MB231 xenograft model. Changes in tumour growth. Intraperitoneal (IP) or subcutaneous (SC) injections.

In another experiment, HB19 (5 mg/kg) was administered by intraperitoneal route (IP) and peritumoral route (SC) (FIG. 10). The results show that the anti-tumour action of HB-19 is equally effective by intraperitoneal route (IP) and peritumoral route, demonstrating not only the unexpected efficacy of pentavalent compound HB-19 but also its bioavailability in vivo at the tumour site, including in the case of systemic administration.

It should also be noted that in the course of treatment by HB-19, no abnormal physiological or behavioural sign was observed in treated mice. In addition, anatomical examination of the organs at the end of the experiment did not reveal any visible sign of tissue toxicity nor any change in blood formula or platelet count.

Figure 11:
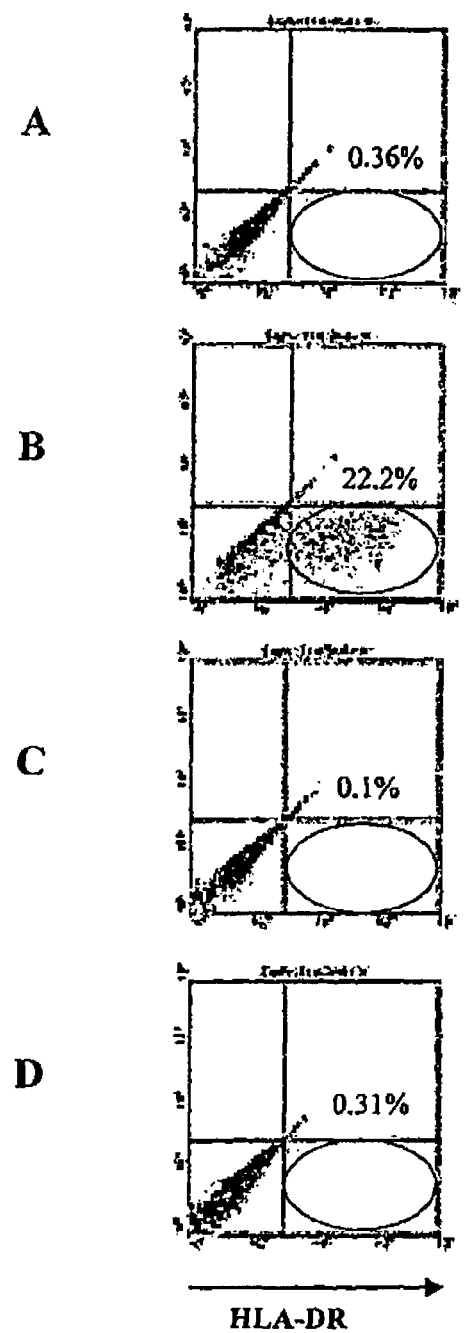
FIG. 11. Effect of HB-19 on metastatic tumour cells in a MDA-MB231 xenograft model. Investigation of MDA-MB231 cells in the blood of xenografted mice and treated or not with HB-19 was performed by flux cytometry (FACS) using anti HLA-DR antibodies. HLA-DR$^+$ are surrounded and the percentage of HLA-DR$^+$ cells among blood cells is indicated. A. Blood of mice without an MDA-MB231 xenograft, untreated, percentage of HLA-DR$^+$ cells among peripheral blood cells: 0.36% B. Blood of mice without an MDA-MB231 xenograft, untreated, percentage of HLA-DR+ cells among peripheral blood cells: 22.2% C. Blood of mice with MDA-MB231 xenograft, treated with HB-19 by subcutaneous route, percentage of HLA-DR+ cells among peripheral blood cells: 0.1% D. Blood of mice with an MDA-MB231 xenograft, treated with HB-19 by intraperitoneal route, percentage of HLA-DR+ cells among peripheral blood cells: 0.31%.
Figure 12:
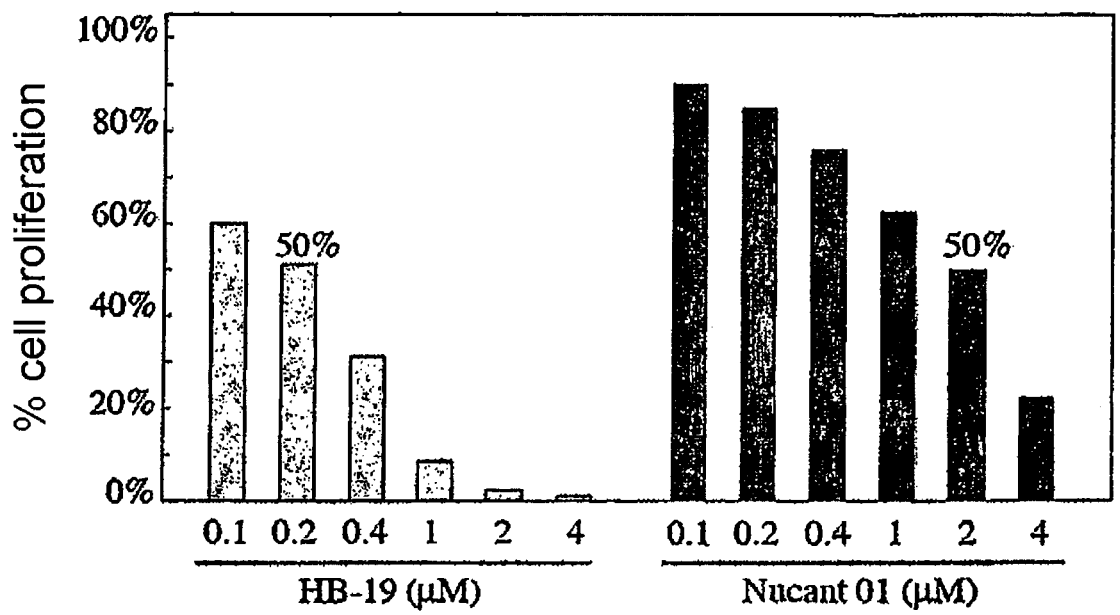
FIG. 12. Effect of HB-19 and Nucant 01 on the growth of NIH-3T3 cells stimulated by HARP. Quiescent NIH-3T3 cells were stimulated or not by 4 nM of HARP in the presence of HB19 or Nucant 01 at the concentrations indicated. After 24 hours of incubation, cell proliferation was determined by measuring the incorporation of tritiated thymidine. The results (mean of 3 points) are given as the percentage of cell proliferation with respect to the control stimulated by HARP in the absence of HB19 and Nucant 01 (100% cell proliferation).
Figure 13:
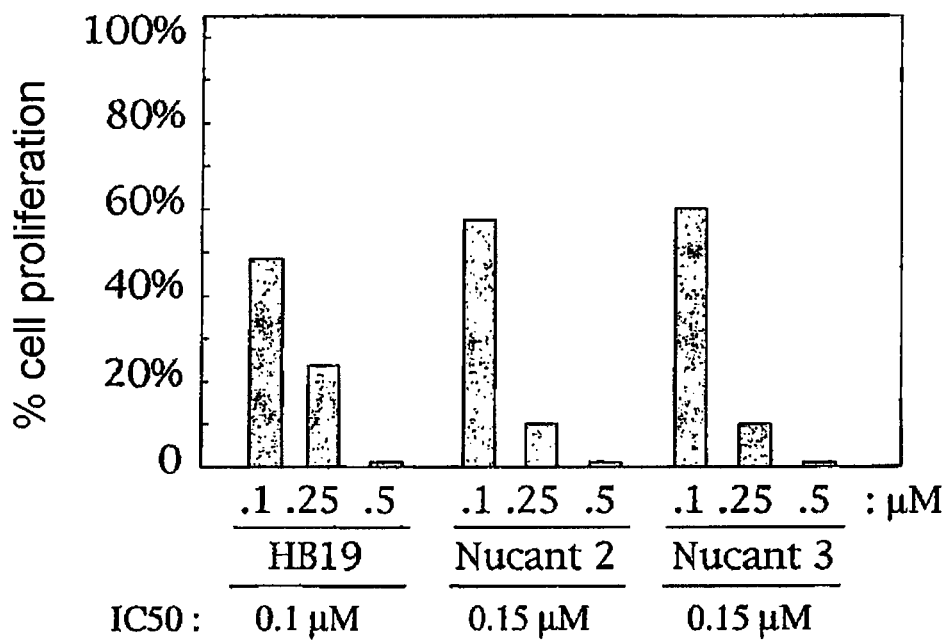
FIG. 13. Effect of HB-19, Nucant 2 and Nucant 3 on the growth of NIH-3T3 cells stimulated by HARP. Quiescent NIH-3T3 cells were stimulated or not by 4 nM of HARP in the presence of HB19, Nucant 2 or Nucant 3 at the concentrations indicated (0.1, 0.25 and 0.5>M). After 24 hours of incubation, cell proliferation of NIH-3T3 cells was determined by measuring the incorporation of tritiated thymidine. The results (mean of 3 points) are given as the percentage of cell proliferation with respect to the control stimulated by HARP (100% cell proliferation). The IC50 concentrations (concentration leading to 50% inhibition of cell proliferation with respect to the control stimulated by HARP) are also given.

Moreover, it was not possible to detect HLA-DR$^+$ human cells (therefore MDA-MB231 tumour cells) in the peripheral blood cells of xenografted mice treated with HB-19 (FIG. 11). In fact, contrary to untreated mice (PBS) in which the proportion of MDA-MB231 cells (HLA-DR$^+$) represents 22.2% of peripheral blood cells, this proportion is only 0.1% to 0.31% in the case of mice treated with HB-19 by subcutaneous or intraperitoneal route. These results suggest that HB-19 is also capable of preventing the circulation of tumour cells in the blood and, consequently, of preventing metastatic phenomena.

Conclusion

The results presented in Example 2 show that pentavalent compound HB-19 is a powerful inhibitor of cell proliferation as a result of its dual tumour growth and angiogenesis effects. These observations have been confirmed in an in vivo model showing that treatment by peritumoral injection of HB-19 is capable of inducing inhibition and even regression of tumours in a PC3 cell xenograft model in athymic mice, and this without tissue toxicity.

Compared to conventionally used treatments in cancer therapy, such as taxol, HB-19 in the experimental model used appears to be much more efficacious. This greater efficacy of HB-19 compared to tamoxifen may be the consequence of the inhibitory effect of HB-19 on both tumour growth and the formation of the vessels needed for tumour proliferation. Whether in the case of tumour cells or activated endothelial cells, HB-19 targets and blocks the proliferation of these two types of cells.

Many cells exist which have the property of inhibiting the proliferation of tumour cells. These molecules often have an effect without really having a cell target. In fact, for many chemotherapy agents, the molecular target present in a tumour cell is also found in normal cells which explains the many side effects of such treatments. Targeted biological agents have fewer side effects as they block a target that is not present or only minimally present in normal cells. Nucleolin present on the surface of activated cells responds to this property and therefore constitutes an ideal therapeutic target in the treatment of cancer. It is also important to note that we target not only tumour cells but also activated endothelial cells. Moreover, surface nucleolin does not appear to be restricted to a particular type of cancer.

The efficacy of dual targeting (tumour cells themselves and activated endothelial cells) should be compared with the results of a study conducted by Genentech which showed, in a randomized trial, that an antiproliferative agent (5-fluorouracile) combined with an anti-angiogenic agent (Avastin) was highly effective in cases of human colorectal cancer (28). In a phase III trial, Avastin treatment as a complement to chemotherapy (irinotecan/5-fluorouracile/leucovorin) prolonged survival rates highly significantly by five months on average (20.3 months compared to 15.6 months) in individuals with previously untreated metastatic colorectal cancer. In these patients, it was found that the length of time during which the tumour did not grow increased from 6.2 months to 10.6 months compared to patients receiving only chemotherapy (29).

This dual effect on tumour cells and endothelial cells makes HB-19 a molecule of choice in the treatment of cancer.

Anti-tumour activity of trivalent compound Nucant 01

Synthesis of Trivalent Compound Nucant 01

The chemical structure of trivalent compound Nucant 01 is given in FIG. 2B. This compound has as a support a cyclic hexapeptide consisting of alternate alanine (A) residues of configuration D and lysine residues (K) of configuration L. Three pseudopeptide units KΨPR (with Ψ=CH$_2$—NH) are covalently bound to the ε amino group of each of the 3 lysine residues (K).

The synthesis of compound Nucant 01 involves covalent coupling of the KΨPR unit to a C3-symmetric cyclic <<core>> molecule. Synthesis of the core molecule is described by S. Fournel et al. (30). The protected KΨPR unit was assembled on a chlorotrityl type resin using a standard solid phase synthesis technique according to Fmoc type chemistry then cleaved from the resin under weak acid conditions. The protected KΨPR unit was then coupled to the epsilon NH2 group of each lysine residue (K) of the core molecule on the basis of 1.1 KΨPR/1 cyclic molecule stoechiometry. Coupling was carried out in accordance with a BOP/HoBt activation procedure for 48 hours. At the end of the reaction, the groups protecting KΨPR were cleaved in trifluoroacetic acid and the final compound precipitated in ether. The Nucant 01 molecule obtained at the end of the procedure was purified by HPLC and fully characterised by mass spectrometry.

Inhibitory Activity of Nucant 01 on the Proliferation of Tumour Cells In Vitro

The effect of Nucant 01 on the proliferation of NIH-3T3 cells stimulated by HARP was compared with that of pentavalent compound HB-19. Quiescent NIH-3T3 cells were stimulated or not by 4 nM of HARP in the presence of HB19 or Nucant 01 at the concentrations indicated (0.1, 0.2, 0.4, 1, 2 and 4 µM). After 24 hours of incubation, cell proliferation of NIH-3T3 cells was determined by measuring the incorporation tritiated thymidine as described earlier.

Compared to the control stimulated by HARP in the absence of HB19 and Nucant 01 (100% cell proliferation), it is found that the compound Nucant 01, which is only trivalent for KPR units, also leads to 50% inhibition of cell proliferation of NIH-3T3 cells stimulated HARP at a concentration of 2 µM. This result therefore demonstrates that synthetic multivalent compounds with at least 3 pseudopeptide units of formula (I) grafted on a cyclic peptide also make it possible, in the same way as pentavalent compound HB-19 whose support is a linear peptide, to inhibit tumour cell proliferation triggered by HARP.

The required concentration is 10 times higher than that needed to obtain the same level of inhibition with HB-19 (0.2 µM) but the compound Nucant 01 only has 3 pseudopeptide units of formula (I) whereas compound HB-19 has 5.

It is therefore probable that increasing the number of pseudopeptide units of formula (I) grafted on a cyclic peptide of the kind used in Nucant 01, to 4 or 5 would further increase the efficacy of the compound, possibly up to 100 times.

Conclusion

These results clearly demonstrate the importance of a multivalent form of the pseudopeptides of formula (I) for the activity of the compounds used in the invention, with the possibility of using a variety of supports, and linear peptides or cyclic peptides can be used without affecting the efficacy of the compounds.

Other acceptable supports can therefore be used equally well as long as they allow at least 3, preferably 3 to 8, preferably 4 to 6, preferably 5 or 6 pseudopeptide units of formula (I) to be grafted on.

Anti-tumour activity of pentavalent compounds Nucant 2 and Nucant 3

Synthesis of Pentavalent Compounds Nucant 2 and Nucant 3

Two peptide supports known to adopt a helicoidal structure on which KΨPR units were anchored were assembled by solid phase synthesis. These supports were made up of repeated units of sequence Aib-Lys-Aib-Gly for NUCANT 2 and Lys-Aib-Gly for NUCANT 3 linked together five times, in which Aib represents 2-amino-isobutyric acid. Assembly was carried out by means of Boc type chemistry. Protective Fmoc groups of the lysine residue side chain were then cleaved by treatment with piperidine (3 times 5 minutes) in DMF. The five εNH2 groups of lysine then acted as anchors for the KΨPR units (with Ψ=CH$_2$—N). Final acid cleavage was carried out in hydrofluoric acid. After precipitation of peptides in ether, dissolution in aqueous conditions and freeze-drying, NUCANT 2 and NUCANT 3 analogues were purified by HPLC and analysed by mass spectrometry then freeze dried.

Inhibitory Activity of Nucant 2 and Nucant 3 on the Proliferation of Tumour Cells In Vitro The effect of Nucant 2 and Nucant 3 on the proliferation NIH-3T3 cells triggered by HARP was compared to that of pentavalent compound HB-19. Quiescent NIH-3T3 cells were stimulated or not by 4 nM by HARP in the presence of HB19, Nucant 2, or Nucant 3 at the concentrations indicated (0.1, 0.25 and 0.5 µM). After 24 hours of incubation, cell proliferation of NIH-3T3 cells was determined by measuring the incorporation tritiated thymidine as described earlier.

In this experiment, HB19 inhibits with IC50 at 0.1 µM. Nucant 2 and Nucant 3 inhibit cell proliferation in a dose-dependent manner with IC50 at 1.5 µM.

The pentavalent compounds Nucant 2 and Nucant 3 are therefore capable of inhibiting cell proliferation in a dose-dependent manner, with a IC50 (concentration leading to 50% inhibition of cell proliferation) very similar to that of compound HB19.

The effect of Nucant 3 on the proliferation of NIH-3T3 cells treated by 5% of FCS was also compared to that of compound HB-19. NIH-3T3 cells made quiescent by serum deprivation were stimulated by 5 FCS in the presence or not of different concentrations of NUCANT 3, 6 or 7 ranging from 0.125 to 2 µM. After 24 hours in incubation, cell proliferation is determined by measuring the incorporation of tritiated thymidine as described earlier.

Figure 14:
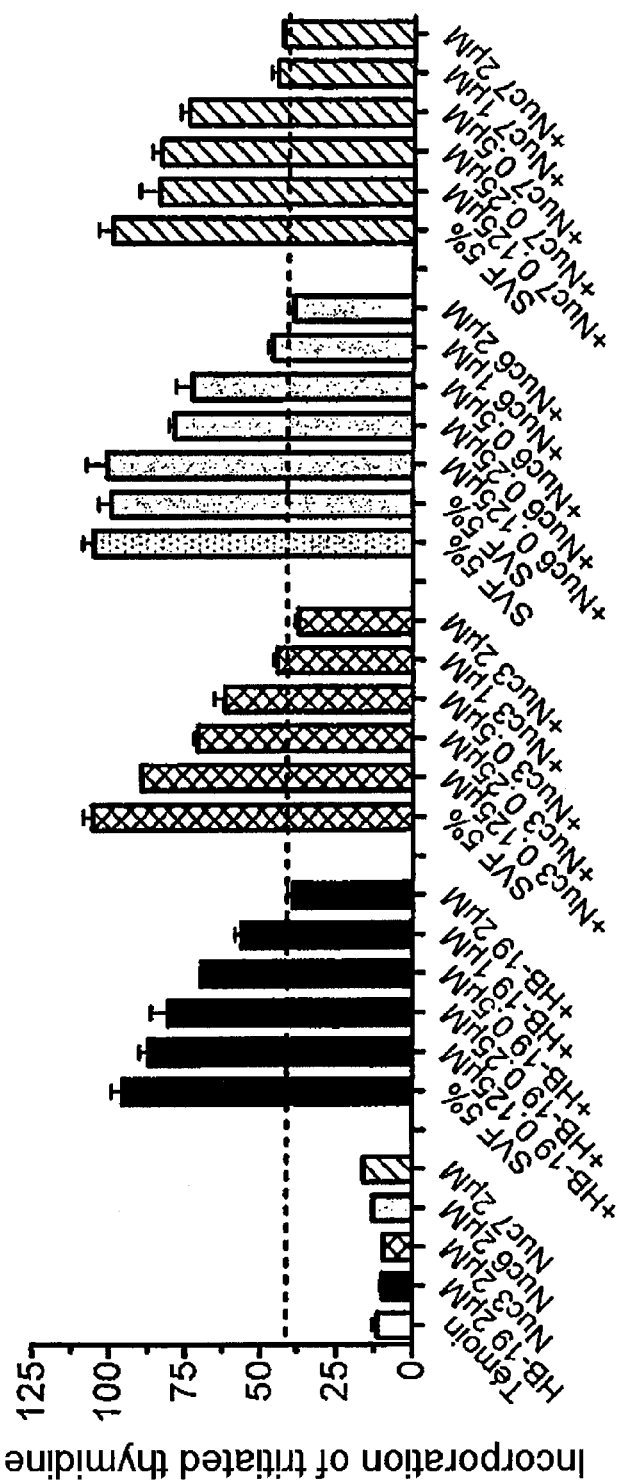
FIG. 14. Effect of NUCANT 3, 6 and 7 on the proliferation of NIH-3T3 cells stimulated by 5% FCS. NIH-3T3 cells are made quiescent by serum deprivation are stimulated by 5% FCS in the presence or not of various NUCANT 3, 6 and 7 concentrations ranging from 0.125 to 2 µM. After 24 hours of incubation, cell proliferation was determined by measuring the incorporation of tritiated thymidine. The results are given as a percentage with respect to the control cells stimulated by 5% FCS. $ID_{50}$ is indicated by the dotted line.

The results are presented in FIG. 14 as a percentage with respect to control cells stimulated by 5 FCS. The results show that NUCANT 3 has an inhibitory effect on cell proliferation. Analysis of the graph shows that NUCANT 3 has an ID$_{50}$ value (Inhibitory Dose at 50%) that is similar but slightly lower than that of the HB-19 molecule and is therefore slightly less effective than HB-19. No effect was observed with NUCANT 3 on non-stimulated cells, indicating the absence of any toxicity of these molecules.

Conclusion

These results also demonstrate the importance of a multivalent form of pseudopeptides of formula (I) for the activity of the compounds used in the invention, the support used equally well being a linear peptide which contains or not structural elements (13 fold, (3 sheets), a linear peptide with a helicoidal structure or even a cyclic compound, without this affecting the efficacy of the structure.

Various acceptable supports can thus be used interchangeably as long as they allow at least 3, preferably between 3 and 8, preferably between 4 and 6, preferably 5 or 6 pseudopeptide units of formula (I) to be grafted on.

Anti-tumour activity of hexavalent compounds Nucant 6 and Nucant 7

Synthesis of Hexavalent Compounds Nucant 6 and Nucant 7

These hexavalent compounds were obtained using the same synthesis process as that used for pentavalent compounds Nucant 2 and 3.

Inhibitory Activity of Nucant 6 and Nucant 7 on the Proliferation of Tumour Cells In Vitro The effect of hexavalent compounds Nucant 6 and Nucant 7 on the proliferation of NIH-3T3 cells triggered by 5% FCS was compared with that of pentavalent compound HB-19. NIH-3T3 cells made quiescent by serum deprivation stimulated by 5% FCS in the presence of various concentrations of NUCANT 3, 6 or 7 ranging from 0.125 to 2 µM. After 24 hours of incubation, cell proliferation was determined by measuring the incorporation of tritiated thymidine as described above.

The results are given in FIG. 14 as a percentage with respect to control cells stimulated by 5 FCS. The results show that NUCANT 6 and 7 have an inhibitory effect on cell proliferation. NUCANT 6 and 7 have an $ID_{50}$ value (Inhibitory Dose at 50%) that is similar but slightly lower than that of the HB-19 molecule and are therefore slightly less effective than HB-19. No effect was observed with NUCANT 6 or 7 on non-stimulated cells, indicating the absence of any toxicity of these molecules.

Conclusion

These results are a further demonstration of the importance of a multivalent form of pseudopeptides of formula (I) for the activity of the compounds used in the invention, the support used equally well being a linear peptide which contains or not structural elements (13 bend, (3 sheets), a linear peptide with a helicoidal structure or even a cyclic compound, without this affecting the efficacy of the construction.

In particular, the form with 6 pseudopeptide units appears to be highly effective in obtaining the desired anti-proliferation and anti-angiogenic effects.

Nucant 6 and Nucant 7 are more powerful inhibitors of surface nucleolin than HB-19

Nucant 6 and Nucant 7 are More Powerful Inhibitors than HB-19 and Inhibit The Activity of Surface Nucleolin The activity of surface nucleolin was tested in HeLa P4 cells using the technique we have described previously (13).

Figure 15:
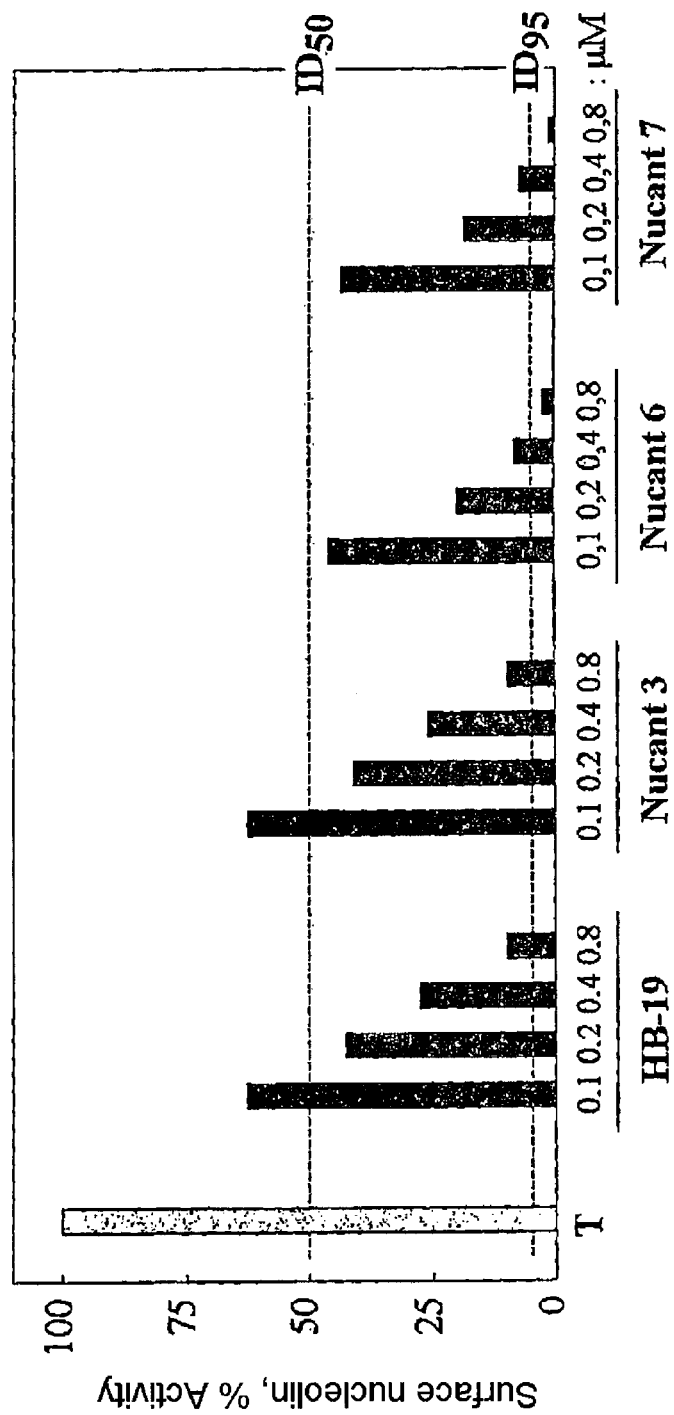
FIG. 15. Nucant 6 and Nucant 7 show better anti-surface nucleolin activity than HB-19. $ID_{50}$: concentration in µM which inhibits surface nucleolin by 50%. $ID_{95}$: concentration in µM which inhibits surface nucleolin by 95%.

The results presented in FIG. 15 show that inhibition of surface nucleolin activity by Nucant 3 is comparable to that of HB-19. On the other hand, Nucant 6 and Nucant 7 have greater surface anti-nucleolin activity than HB-19. HB-19 and Nucant 3 have an $ID_{50}$ value (Inhibitory Dose at 50%) which is between 0.1-0.2 μM, whereas Nucant 6 and Nucant 7 have an $ID_{50}$ value below 0.1 μM. Moreover, Nucant 6 and Nucant 7 used at 0.8 μM lead to over 95% inhibition of surface nucleolin activity.

HB-19, Nucant 3, 6, and 7 Lead to Inhibition of Surface Nucleolin in Human Breast Cancer Cells, MDA-MB 231

Surface nucleolin plays an important role in proliferation and tumour angiogenesis. HB-19 as well as related molecules Nucant 3, Nucant 6 and Nucant 7 specifically bind to surface nucleolin, thus blocking tumour growth and angiogenesis. After these pseudopeptides bind to surface nucleolin, the [pseudopeptide-nucleolin] complex is rapidly internalised by means of an active process. These results are presented in FIG. 16A and show that treatment of cells with HB-19 (line 1), Nucant 3 (line 2), Nucant 6 (line 3) or Nucant 7 (line 4), result in a reduction in the presence of surface nucleolin compared to untreated cells. This reduction is observed after 24 hours of treatment but also after 48 hours of treatment in which case nucleolin becomes non-detectable.

Figure 16:
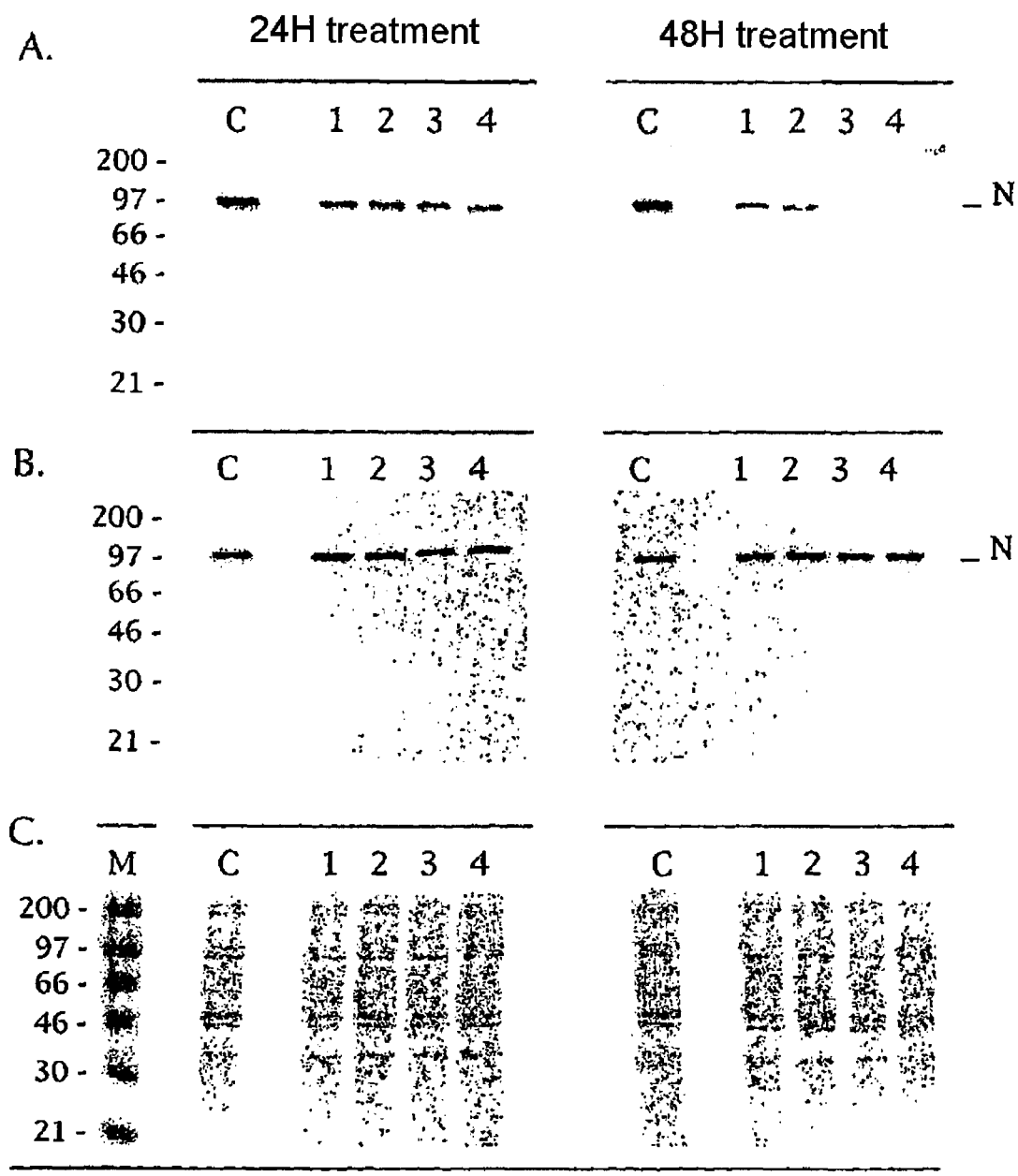
FIG. 16. Inhibitory effect of HB-19, Nucant 3, Nucant 6 and de Nucant 7 on cell expression of nucleolin by MDA-MB 231 cells. MDA-MB 231 cells were cultured in 75 cm$^2$ in DMEM containing 10% foetal calf serum. After 2 days in culture, subconfluent cells (about 3×10$^6$ cell per vial) were treated with 10 µM of HB-19 (line 1), Nucant 3 (line 2), Nucant 6 (line 3) or Nucant 7 (line 4) for 24 or 48 hours. Lines C represent untreated cells. After 24 or 48 hours of treatment, cells were washed in PBS and incubated with 10 ml of DMEM containing 1% foetal calf serum and biotinylated HB-19 (5 µM) for 45 minutes at room temperature. After intensive washing in PBS containing 1 mM EDTA (PBS-EDTA), cytoplasmic extracts were prepared using a lysis buffer containing 20 mM Tris HCl, pH 7.6, 150 mM NaCl, 5 mM $MgCl_2$, 0.2 mM phenylmethylsulfonyl fluoride, 5 mM β-mercaptoethanol, aprotinin (1000 U/ml) and 0.5% Triton X-100. The complex formed between surface nucleolin and biotinylated HB-19 was isolated purification of the extracts using avidine-agarose (100 µl; ImmunoPure Immobilized Avidin, Pierce Chemical Company, USA) in PBS-EDTA. After 2 hours of incubation at 4° C., the avidine-agarose samples were thoroughly washed with PBS-EDTA. These samples containing purified surface nucleolin (A material corresponding to 2×10$^6$ cells) and crude cell extracts (B and C; material corresponding to 4×10$^5$ cells) were denatured by heating in electrophoresis buffer containing SDS and analysed by SDS-PAGE. The presence of surface nucleolin was revealed by immunoblotting using D3 monoclonal antibodies (A and B). Electrophoresis analysis after staining with Coomassie Blue is shown in C. Line M corresponds to molecular weight markers.

It is interesting to note that there is a considerably greater reduction in surface nucleolin when cells are treated for 24 hours with pseudopeptides Nucant 6 and Nucant 7 (lines 3 and 4) compared to cells treated with HB-19 and Nucant 3 (lines 1 and 2). The same observation is made after 48 hours of treatment. It is important to note that the reduction in surface nucleolin is not the result of a reduction in the intracellular amount of surface nucleolin. In fact, identical amounts of nucleolin are found in cell extracts of cells either treated or not by HB-19 or by the various types of Nucant (FIG. 16B). Similarly way, it is found that there is no difference between the electrophoresis profiles of proteins extracted from cells whether treated or not by HB-19 or the different types of Nucant. This result illustrates that protein synthesis is not affected by HB-19 or the different types of Nucant studies. Moreover, it is interesting to note that HB-19 and the different types of Nucant studied have no cytotoxic effect that might explain the observed reduction in surface nucleolin.

Conclusions

This set of results shows that:
a) nucleolin is expressed in large quantities at the surface of tumour cells, for example in human breast cancer cells (MDA-MB231).
b) treatment by HB-19, Nucant 3, Nucant 6 and Nucant 7 triggers a marked decrease in the nucleolin <<pool>> present at the surface of cells.
c) the pseudopeptides Nucant 6 and Nucant 7 are more effective in producing a reduction in the nucleolin <<pool>> present at the surface of cells, as well as in inhibiting the activity of surface nucleolin.

Effect of HB-19 and Nucant 7 on Angiogenesis

Methods

The effect of HB-19 and Nucant 7 on angiogenesis was tested in an ex vivo model of angiogenesis, the chorio-allantodoin membrane (CAM) of chicken embryo.

Figure 17:
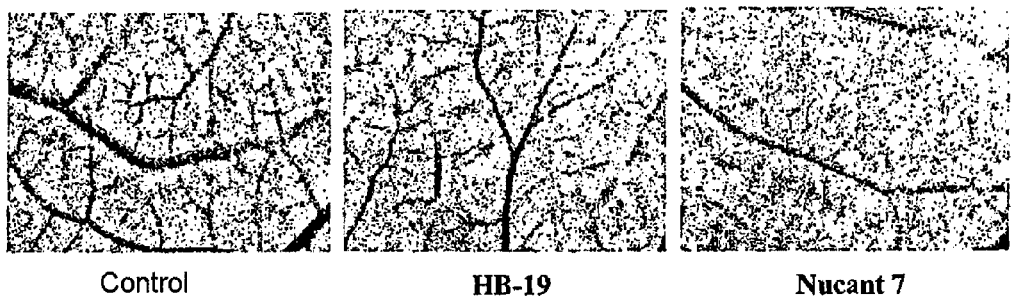
FIG. 17. Inhibition of angiogenesis in an ex vivo CAM model. 20 µl of water containing or not (control) HB-19 (10 µM; 0.6 µg) or Nucant 7 (10 µM; 0.8 µg) are deposited on the surface of CAM. Observation of vessels is carried out after 48 hours of incubation.

20 μl of water containing or not (control) HB-19 (10 μM; 0.6 μg) or Nucant 7 (10 μM; 0.8 μg) are deposited on the surface of CAM. Observation of vessels was carried out after 48 h of incubation Results The results are presented in FIG. 17 and show that after 48 hours of incubation, HB-19 and Nucant 7 clearly lead to inhibition of angiogenesis. An image analysis study, taking into consideration not only capillary length but also the number of branches, suggests inhibition in the region of 50% compared to the control.

Anti-inflammatory activity of compounds HB19 and Nucant 7

Inhibition by HB-19 of the Production TNF-α by Human Primary PBMC Stimulated by LPS.

Methods

PBMCs were isolated by centrifugation on a Ficoll density gradient using whole human blood EDTA-potassium and resuspended in RPMI 1640 containing 1% human serum AB (Invitrogen). Cells at a concentration of $10^6$ cell/0.5 ml, in the absence (0) or presence (1 and 5 μM) of HB-19, were stimulated with 100 ng/ml of LPS from *Escherichia coli* type 0111:B4 and 055:B5, and LPS from *Salmonella enterica* serotype Re 595. The same PBMCs were stimulated with PMA: Ionomycin (Phorbol 12-myristate 13-acetate:Ionomycin) at 20 ng/ml:1 μM. PBMC cultures were incubated at 37° C. in an incubator with 5% $CO_2$. The level of TNF-α protein was measured by ELISA in culture supernatants collected after 20 hours of incubation.

Results

Figure 18:
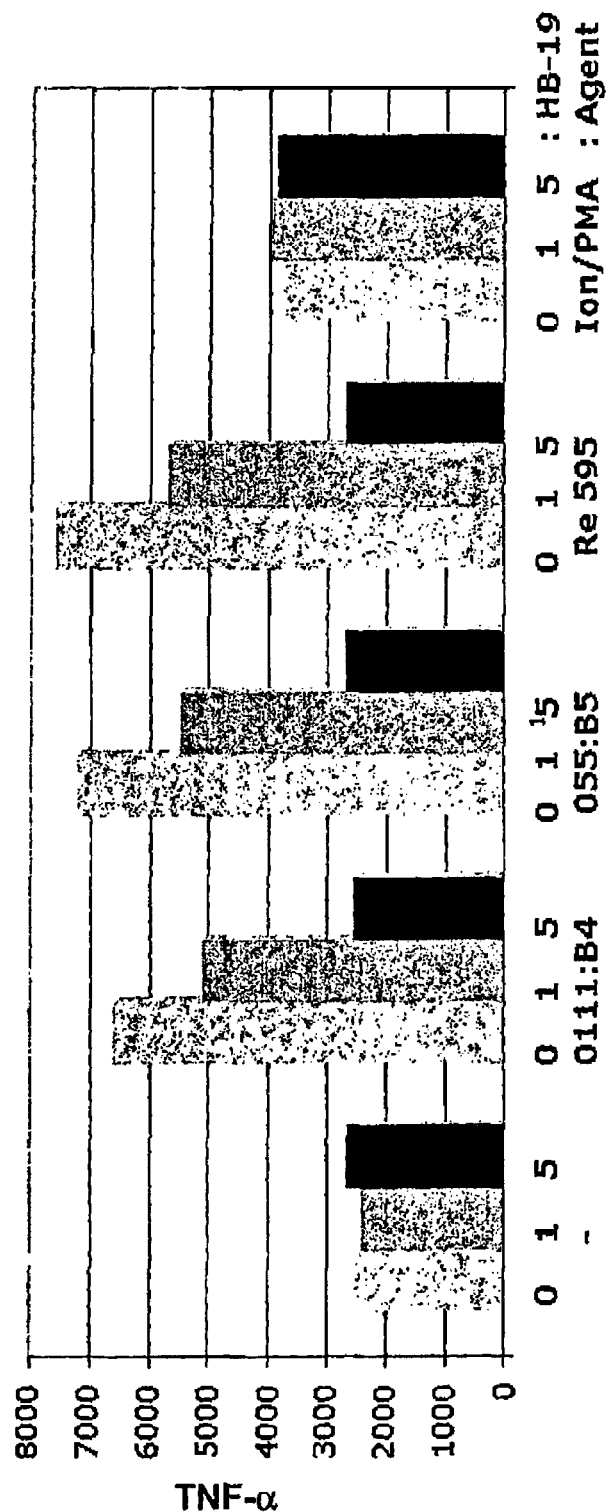
FIG. 18. Inhibition by HB-19 of the production of TNF-α by primary human mononuclear peripheral blood cells (PBMC) stimulated by various LPS preparations. PBMCs were isolated by centrifugation on a Ficoll density gradient using whole human blood EDTA-potassium and resuspended in RPMI 1640 containing 1% human serum AB (Invitrogen). Cells at a concentration of 10$^6$ cell/0.5 ml, in the absence (O) or presence (1 and 5 µM) of HB-19, were stimulated with 100 ng/ml of LPS from *Escherichia coli* type 0111: B4 and 055: B5, and LPS from *Salmonella enterica* serotype Re 595. The same PBMCs were stimulated with PMA: Ionomycin (Phorbol 12-myristate 13-acetate: Ionomycin) at 20 ng/ml:1 µM. PBMC cultures were incubated at 37° C. in an incubator with 5% $CO_2$ Levels of TNF-α protein were measured by ELISA in culture supernatants collected after 20 hours of incubation.

The results (see FIG. 18) show that freshly isolated PBMC produces TNF-α and that this constitutive production of TNF-α is not affected by HB-19. On the other hand, HB-19 inhibits the production of TNF-α by PBMC in a dose-dependent manner in response to stimulation by various LPS preparations from *Escherichia coli* or *Salmonella enterica*. This effect is specific because HB-19 does not have an effect on the production of TNF-α by PBMC in response to stimulation by PMA-Ionomycin.

At 5 μM of HB-19, the production TNF-α by human PBMC in response to stimulation by various LPS preparations is inhibited to a similar degree to the base level observed in the absence of stimulation by LPS.

Inhibition by HB-19 and Nucant 7 of the Production of TNF-α and IL-6 by Murine Macrophages from Primary Peritoneum Stimulated by LPS Method In order to obtain stimulated macrophages, 7 to 8 week old balb/c mice received and intra-peritoneal injection 4 days prior to the experiment using 1.5 ml of a thioglycolate solution (3% saline solution). Macrophages were collected in the peritoneal cavity by washing the peritoneum with 5 ml of RPMI medium containing 1% foetal calf serum. Cells were then placed on plates at a density of $10^6$ cells/0.5 ml in RPMI 1640 medium, incubated at 37° C. in an incubator with 5% $CO_2$, and non-adhering cells were removed 2 hours later.

Macrophages, in the absence (−) or presence (+) of 4 µM HB-19 or 10 µM Nucant 7, were either non-stimulated or stimulated with LPS from *Escherichia Coli* serotype 0111:B4 at 10 ng/ml, 100 ng/ml and 1000 ng/ml. Cell cultures were incubated at 37° C. in an incubator with 5% $CO_2$ for 20 hours. TNF-α and IL-6 protein levels were measured by ELISA.

Results

Figure 19:
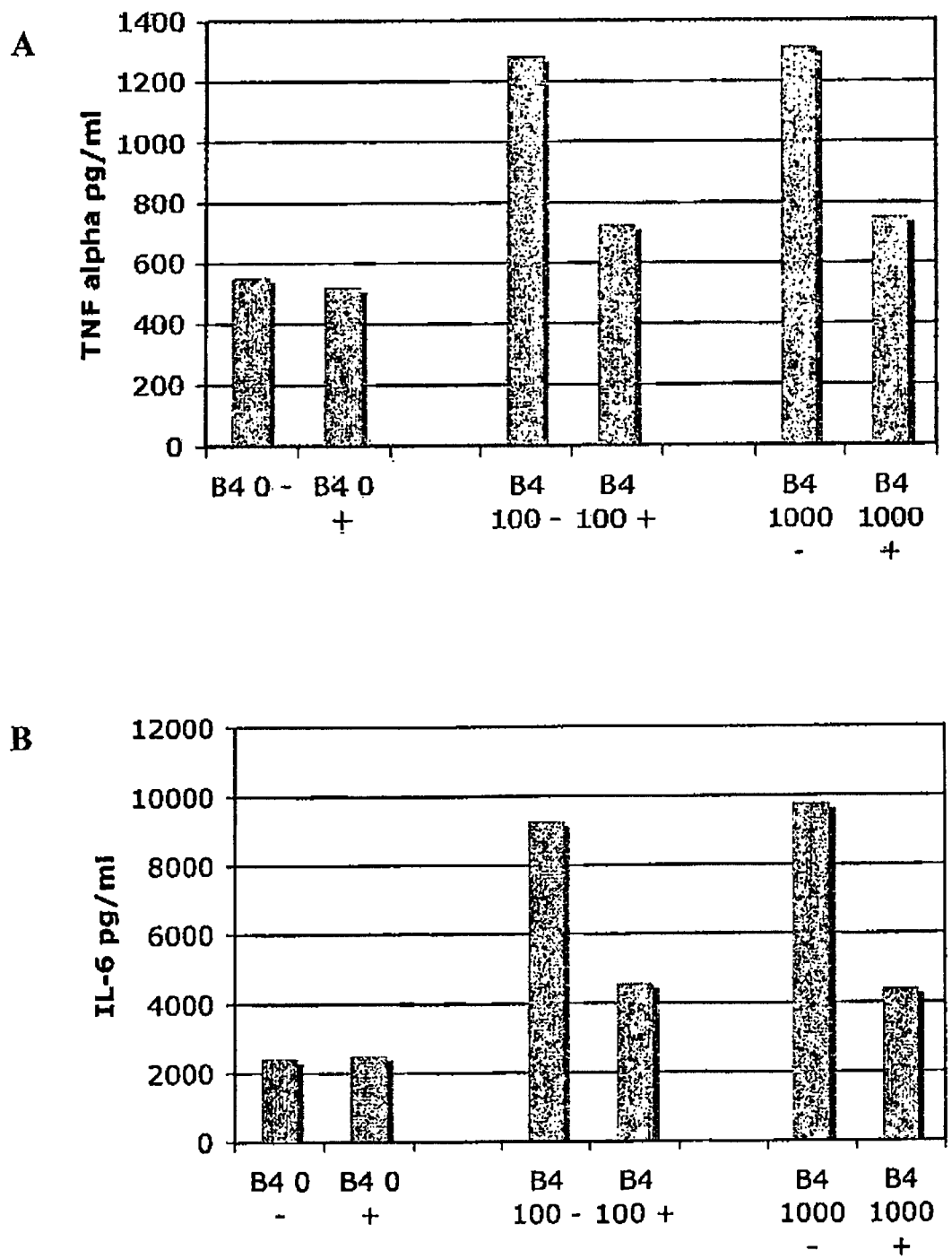
FIG. 19. Inhibition by HB-19 of the production of TNF-α and IL-6 by primary peritoneal murine macrophages stimulated by various LPS preparations. Peritoneal murine macrophages in the absence (−) or presence (+) of 4 µM of HB-19 were either not stimulated (B4 0) or stimulated with LPS from *Escherichia coli* type 0111:B4 at 100 ng/ml (B4 100) and 1000 ng/ml (B4 1000). Cell cultures were incubated at 37° C. in an incubator with 5% $CO_2$ for 20 hours and levels of TNF-α (A) and IL-6 (B) were measured by ELISA.

The results obtained for HB-19 are presented in FIG. 19. At 4 µM of HB-19, the production of TNF-α and IL-6 by murine peritoneal macrophages in response to stimulation by LPS is significantly inhibited. If the base level observed in the absence of stimulation by LPS is taken into account, the net degree of inhibition is 72-75% for TNF-α and 68-71% for IL-6.

Figure 20:
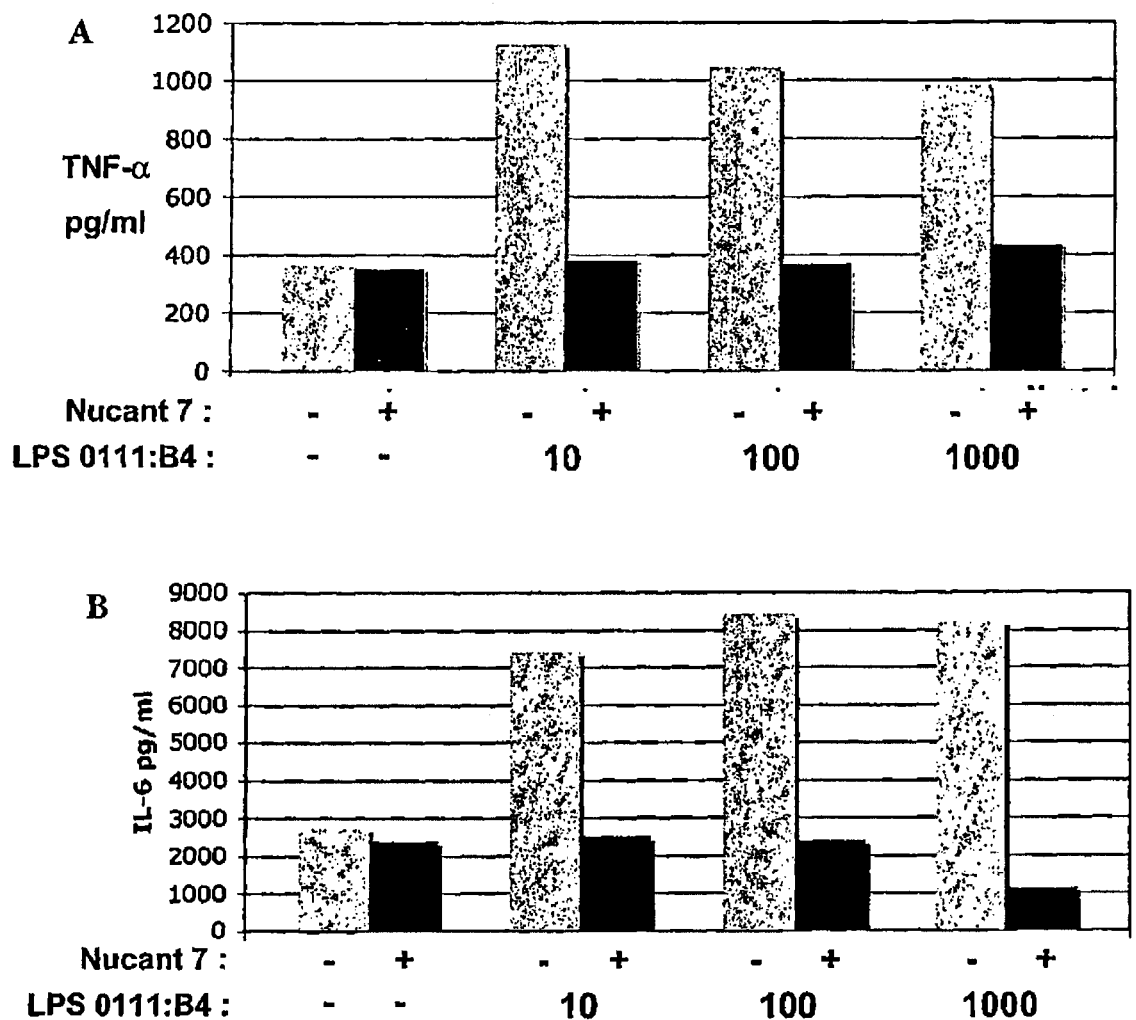
FIG. 20. Inhibition by Nucant 7 of the production of TNF-α and IL-6 by primary peritoneal murine macrophages stimulated by various LPS. Peritoneal murine macrophages in the absence (−) or presence (+) of 10 µM of Nucant 7 were either not stimulated (−) or stimulated (+) with LPS from *Escherichia coli* type 0111:B4 at 10 ng/ml, 100 ng/ml and 1000 ng/ml. Cell cultures were incubated at 37° C. in an incubator with 5% $CO_2$ for 20 hours and levels of TNF-α (A) and IL-6 (B) were measured by ELISA.

The results obtained with Nucant 7 are presented in FIG. 20. At 10 µM of Nucant 7, the production of TNF-α and IL-6 by murine peritoneal macrophages in response to stimulation by LPS is almost completely inhibited because the cytokine production level observed in cultures treated with Nucant 7 in response to stimulation by LPS is similar to that observed in the absence of LPS.

If the base level observed in the absence of stimulation by LPS is taken into account, the degree of inhibition at 10 µM of Nucant 7 is over 95% in cultures stimulated by 10,100 and 1000 ng/ml of LPS. The fact that the degree of inhibition is not altered in the presence of a 100 times greater LPS concentration suggests that the mechanism of inhibition by Nucant 7 is principally due to binding to surface nucleolin. In fact, if the mechanism of inhibition by Nucant 7 were the result of interaction with LPS, the inhibitory effect would be lower at 100 ng/ml of LPS than 10 ng/ml of LPS.

Inhibition by HB-19 of the Production of IL-8 and Expression of ICAM-1 by HUVEC Cells Stimulated by LPS.

Method

HUVEC cells at a concentration of 10 000 cells/cm$^2$ were cultured in 96-well plates in EBM-2 medium containing 2% foetal calf serum. Cells in the absence or presence of 5 µM of HB-19 were stimulated by LPS from *Escherichia coli* serotype 055:B5 at 100 ng/ml. Cell cultures were incubated at 37° C. in an incubator with 5% $CO_2$ for 20 hours. Levels of IL-8 and ICAM-1 were measured by ELISA. HUVEC cells in the absence or presence of 5 µm of HB-19 were used as a control to show the base level.

Results

Figure 21:
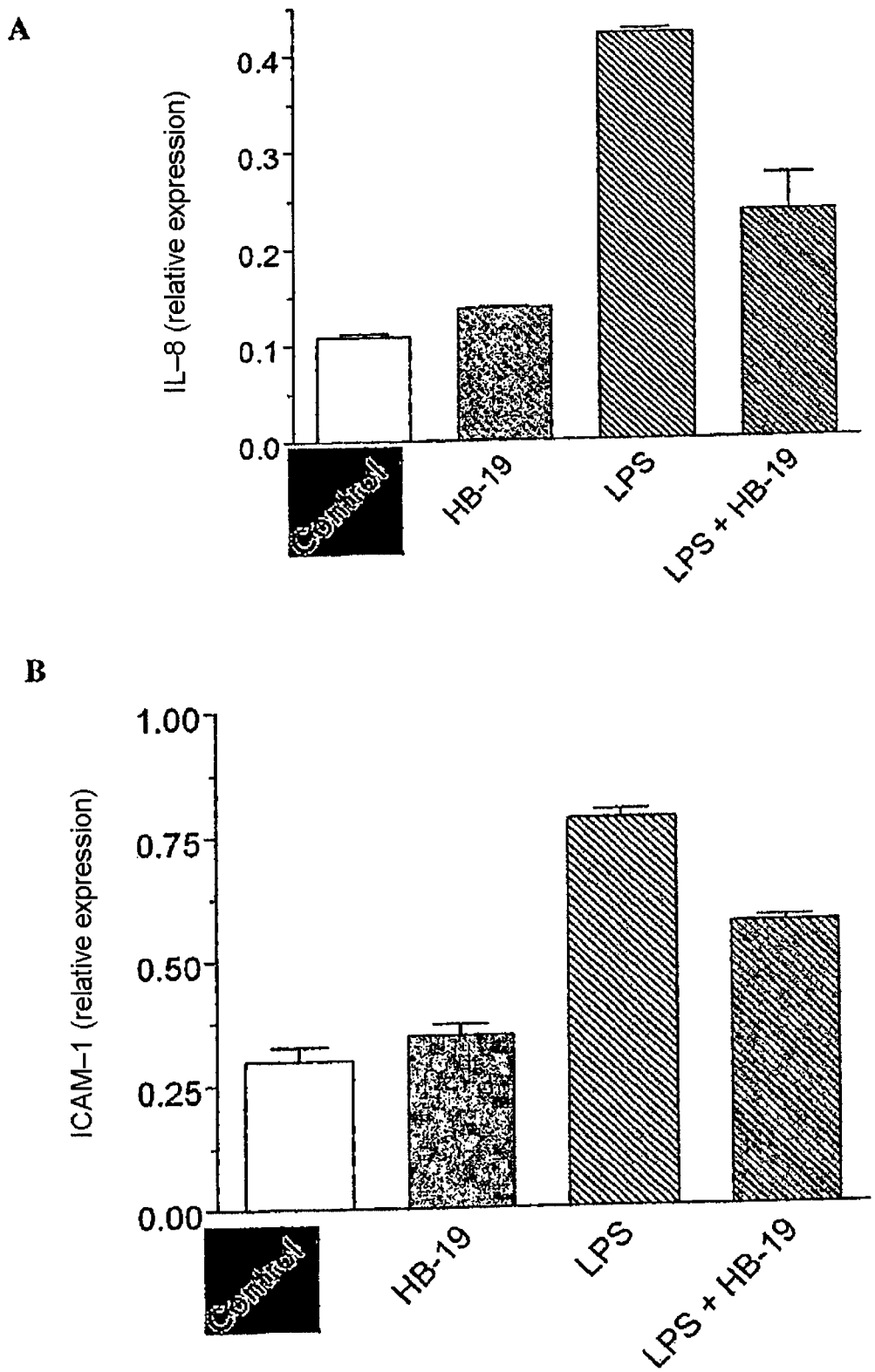
FIG. 21. Inhibition by HB-19 of IL-8 production and ICAM-1 expression by human umbilical vascular endothelial cells (HUVEC) stimulated by LPS. HUVEC cells at 10 000 cells/cm$^2$ were cultured in 96-well plates in EBM-2 medium containing 2% foetal calf serum. Cells in the absence or presence of 5 µM of HB-19 were stimulated with *Escherichia coli* serotype 055:B5 at 100 ng/ml. Cell cultures were incubated at 37° C. in an incubator with 5% $CO_2$ for 20 hours and IL-8 and ICAM-1 protein levels were measured by ELISA. HUVEC cells in the presence or absence of 5 µM of HB-19 were used as the control for base levels.

If the base level observed in the absence of stimulation by LPS is taken into account, the degree of inhibition of IL-8 and ICAM-1 production at 5 µM of HB-19 is around 50%. These results therefore demonstrate the potential efficacy of HB-19 and related compounds of the Nucant type as inhibitors of the production of IL-8 and ICAM-1 (see FIG. 21).

Inhibition by HB-19 of the Production TNF-α by Human Primary PBMC Stimulated by Inactivated *Staphylococcus aureus* Bacteria Infection by *Staphylococcus aureus* has been shown to be one of the major causes in endocarditis (24, 25).

The inventors therefore measured TNF-α and IL-6 levels in human primary PBMC cultures in response to *Staphylococcus aureus* bacteria inactivated by heat (HKSA, <<heat-killed *Staphylococcus aureus*>>), in the absence (control) or presence of 10 µM of the compounds HB-19, Nucant 3, Nucant 6, or Nucant 7. As the positive control (Dex.), PBMC was also treated with dexamethasone which is a glucocorticosteroid with known anti-inflammatory and immunosuppressant activity.

Method

PBMC was isolated by centrifugation on a Ficoll density gradient using whole human blood EDTA-potassium and re-suspended in RPMI 1640 medium containing 1% human serum AB (Invitrogen). Cells at a concentration of $10^6$ cells/ 0.5 ml in the absence (Control) or presence (10 µM) of HB-19, Nucant 3, Nucant 6, Nucant 7, and dexamethasone (1 µg/ml) were stimulated with $10^8$ HKSA/ml particles (InvivoGen, San Diego, USA). PBMC cultures were incubated at 37° C. in an incubator with 5% $CO_2$ The level of TNF-α and IL-6 protein was measured by ELISA in culture supernatants collected after 20 hours of incubation.

Results

Figure 22:
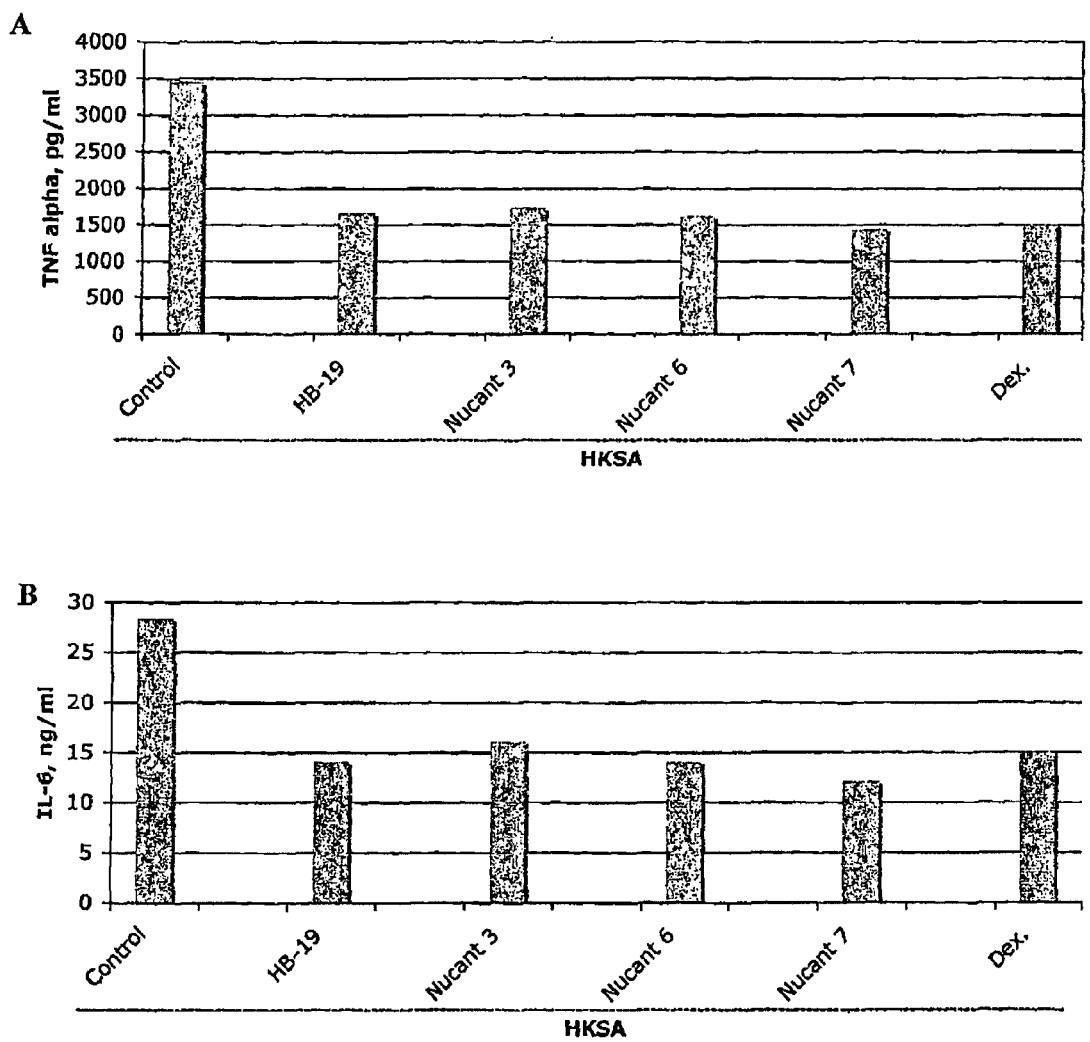
FIG. 22. Inhibition by HB-19 of the production of TNF-α and IL-6 by primary human mononuclear peripheral blood cells (PBMC) stimulated by *Staphylococcus aureus* bacteria inactivated by heat (HKSA, <<heat-killed *Staphylococcus aureus*>>). PBMCs were isolated by centrifugation on a Ficoll density gradient using whole human blood EDTA-potassium and resuspended in RPMI 1640 containing 1% human serum AB (Invitrogen). Cells at a concentration of 10$^6$ cell/0.5 ml, in the absence (control) or presence (10 µM) of HB-19, Nucant 3, Nucant 6 or Nucant 7 or Dexamethasone (Dex. 1 μg/ml), were stimulated with $10^8$ HKSA/ml particles (InvivoGen, San Diego, USA). PBMC cultures were incubated at 37° C. in an incubator with 5% $CO_2$ and TNF-α (A) and IL-6 (B) levels were measured by ELISA in culture supernatants collected after 20 hours of incubation.

The results are presented in FIG. 22 and show that all the pseudopeptides tested (HB-19, Nucant 3, Nucant 6, and Nucant 7) make it possible to obtain significant inhibition of TNF-α and IL-6 production in response to stimulation by heat killed *Staphylococcus aureus* bacteria. The pseudopeptides are as effective as standard anti-inflammatory treatment such as dexamethasone.

Thus the pseudopeptides of formula (I) such as HB-19, Nucant 3, Nucant 6 and Nucant 7, can also be used as treatment for cardiac inflammation, particularly in the treatment of endocarditis of infectious origin.

Conclusion

The results obtained by the inventors therefore show that the compounds HB-19 and Nucant 7 are capable of inhibiting the production of both proinflammatory cytokines such as TNF-α and IL-6, and the production of chemokine IL-8 and adhesion molecule ICAM-1 by various cell types in response to stimulation by LPS.

Moreover, these compounds also lead to significant inhibition of the production of production proinflammatory cytokines such as TNF-α and IL-6 in response to stimulation by *Staphylococcus aureus* bacteria, one of the agents responsible for numerous forms of endocarditis of infectious origin.

Consequently, these compounds as well as the related compounds of formula (I) described in this invention are capable of inhibiting the production of proinflammatory cytokines and molecules involved in the recruitment of leukocytes to the site of inflammation. These compounds can thus be used in anti-inflammatory applications, notably in the treatment of the various diseases mentioned in the general description.

BIBLIOGRAPHY

Hovanessian, A. G., Puvion-Dutilleul, F., Nisole, S., Svab, J., Perret, E., Deng, J. S., and Krust, B. The cell-surface-expressed nucleolin is associated with the actin cytoskeleton. (2000) Exp. Cell Res. 261, 312-328

Nisole, S., Krust, B., Callebaut, C., Guichard, G., Muller, S., Briand, J. P., and Hovanessian, A. G. The anti-HIV compose HB-19 forms a complex with the cell-surface-expressed nucleolin independent of heparan sulfate proteoglycans. (1999) J. Biol. Chem. 274, 27875-27884

Ginisty, H., Sicard, H., Roger, B., and Bouvet, P. Structure and functions of nucleolin. (1999) J. Cell Science 112, 761-772

Srivastava, M., and Pollard, H. B. Molecular dissection of nucleolin's role in growth and cell proliferation: new insights. (1999) FASEB J. 13, 1911-1922

Nisole, S., Krust, B., and Hovanessian, A. G. Anchorage of HIV on permissive cells leads to coaggregation of viral particles with surface nucleolin at membrane raft microdomains. (2002) Exp. Cell Res. 276, 155-173

Semenkovich, C. F., Ostlund, R. E. J., Olson, M. O., and Yang, J. W. A protein partially expressed on the surface of HepG2 cells that binds lipoproteins specifically is nucleolin. (1990) Biochemistry 29, 9708-9713

Callebaut, C., Jacotot, E., Krust, B., Guichar, G., Blanco, J., Svab, J., Muller, S., Briand, J. P., and Hovanessian, A. G. Compose TASP inhibitors of HIV entry bind specifically to a 95-kDa cell surface protein. (1997) J. Biol. Chem. 272, 7159-7166

Callebaut, C., Blanco, J., Benkirane, N., Krust, B., Jacotot, E., Guichard, G., Seddiki, N., Svab, J., Dam, E., Muller, S., Briand, J. P., and Hovanessian, A. G. Identification of V3 loop-binding proteins as potential receptors implicated in the binding of HIV particles to CD4(+) cells. (1998) J. Biol. Chem. 273, 21988-2199

Christian, S., Pilch, J., Akerman, M. E., Porkka, K., Laakkonen, P., and Ruoslahti, E. Nucleolin expressed at the cell surface is a marker of endothelial cells in angiogenic blood vessels. (2003) J. Cell Biol. 163, 871-878

Said, A. E., Krust, B., Nisole, S., Briand, J. P., and Hovanessian, A. G. The anti-HIV cytokine midkine binds the cell surface-expressed nucleolin as a low affinity receptor. (2002) J. Biol. Chem. 277, 37492-37502

Said, E. A., Courty, J., Svab, J., Delbé, J., Krust, B., and Hovanessian, A. G. Pleiotrophin inhibits HIV infection by binding the cell surface-expressed nucleolin. (2005) FEBS J. 272, 4646-4659

Legrand, D., Vigie, K., Said, E. A., Elass, E., Masson, M., Slomianny, M. C., Carpentier, M., Briand, J. P., Mazurier, J., and Hovanessian, A. G. Surface nucleolin participates in both the binding and endocytosis of lactoferrin in target cells. (2004) Eur. J. Biochem. 271, 303-317

Nisole, S., Krust, B., Dam, E., Blanco, A., Seddiki, N., Loaec, S., Callebaut, C., Guichard, G., Muller, S., Briand, J. P., and Hovanessian, A. G. The HB-19 compose 5[Kpsi(CH2N)PR]-TASP inhibits attachment of T lymophocyte- and macrophage-tropic HIV to permissive cells. (2000) AIDS Res. Hum. Retroviruses 16, 237-249

Nisole, S., Said, E. A., Mische, C., Prevost, M. C., Krust, B., Bouvet, P., Bianco, A., Briand, J. P., and Hovanessian, A. G. The anti-HIV pentameric compose HB-19 binds the C-terminal end of nucleolin and prevents anchorage of virus particles in the plasma membrane of target cells. (2002) J. Biol. Chem. 277, 20877-20886

Bates, P. J., Kahlon, J. B., Thomas, S. D., Trent, J. O., and Miller, D. M. Antiproliferative activity of G-rich oligonucleotides correlates with protein binding. (1999) J. Biol. Chem. 274, 26369-26377

Huang Y, Shi H, Zhou H, Song X, Yuan S, Luo Y. The angiogenesis function of nucleolin is mediated by vascular endothelial growth factor and nonmuscle myosin. (2006) Blood 107, 3564-3571.

Seko Y, Cole S, Kasprzak W, Shapiro B A, Ragheb J A. The role of cytokine mRNA stability in the pathogenesis of autoimmune disease. Autoimmun Rev 2006; 5:299-305.

Rot A. Neutrophil attractant/activation protein-1 (intrleukin-8) induces in vitro neutrophil migration by haptotactic mechanism. Eur J Immunol 1993; 23:303-06.

Elass E, Masson M, Mazurier J, Legrand D. Lactoferrin inhibits the lipposaccharaide-induced expression and proteoglycan-binding ability of IL-8 in human entothelial cells. Infect Immun 2002; 70:1860-66.

Kevil C G, Patel R P, Bullard D C. Essential role of ICAM-1 in mediating monocyte adhesion to aortic endothelial cells. Am J Physiol Cell Physiol 2001; 281:C1442-47.

Bucklin S E, Silverstein R, Morrison D C. An interleukin-6-induced acute-phase response does not confer protection against lipopolysaccharide lethality. Infect Immun 1993; 61:3184-89.

Karima R, Matsumoto S, Higashi H, Matsushima K. The molecular pathogenesis of endotoxic shock and organ failure. Mol Med Today 1999; 5:123-32.

Zanotti S, Kulmar A, Kumar A. Cytokine modulation in sepsis and septic shock. Expert Opin Investig Drugs 2002; 11:1061-75.

Alter, P, Hoeschen, J., Ritter, M., Maisch, B. Usefulness of cytokines interleukin-6 and interleukin-2R concentrations in diagnosing active infective endocarditis involving native valves. (2002) Am. J. Cardiol. 89, 1400-1404

Shun, C. T., Lu, S. Y., Yeh, C. Y., Chaing, C. P., Chia, J. S., Chen, J. Y. Glucosyltransferases of viridans streptococci are modulins of interleukin-6 induction in infective endocarditis. (2005) Infec. Immun 73, 3261-3270.

Kannan K, Ortmann R A, Kimpel D Animal models of rheumatoid arthritis and their relevance to human disease. Pathophysiology 2005; 12:167-81.

Peifer C, Wagner G, Laufer S, New approaches to the treatment of inflammatory disorders small molecule inhibitors of p38 MAP kinase. Curr Top Med Chem 2006; 6(2):113-49 2006; 6:113-49.

Kabbinavar, F., Hurwitz, H. I., Fehrenbacher, L., Meropol, N. J., Novotny, W. F., Lieberman, G., Griffing, S., and Bergsland, E. Phase II, randomized trial comparing bevacizumab plus fluorouracil (FU)/leucovorin (LV) with FU/LV alone in patients with metastatic colorectal cancer. (2003) J Clin Oncol 21, 60-65.

Hurwitz, H. I. New agents in colon cancer. (2003) Clin Adv Hematol Oncol 1, 404-405

Fournel, S. et al. C3-symmetric peptide scaffolds are functional mimetics of trimeric CD40L. (2005) Nat Chem Biol 1, 377-382.

---

The invention claimed is:

1. A method for treating cancer comprising the administration of an effective amount of a polyvalent synthetic compound comprising a support on which at least 3 pseudopeptide units are grafted, said compound being of formula (I):

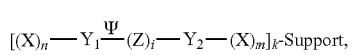

$$[(X)_n-Y_1 \stackrel{\Psi}{-} (Z)_i - Y_2-(X)_m]_k\text{-Support,} \quad (I)$$

wherein the support is a linear peptide, and wherein grafted support residues are separated by at least one amino acid;
each X independently represents any amino acid;
$Y_1$ and $Y_2$ are selected independently from arginine (R) and lysine (K);
Z is proline;
n and i are independently 0 or 1;
m is an integer between 0 and 1;
k is an integer between 3 and 8; and
Ψ represents a modified peptide bond selected from the group consisting of a reduced bond (—CH$_2$NH—), a retro-inverso bond (—NHCO—), a methyleneoxy bond (—CH$_2$—O—), a thiomethylene bond (—CH$_2$—S—), a carba bond (—CH$_2$CH$_2$—), a ketomethylene bond (—CO—CH$_2$—), a hydroxyethylene bond (—CHOH—CH$_2$—), an E-alkene bond or a (—CH═CH—) bond, to a patient in need thereof.

2. The method according to claim 1, wherein said support is selected from a linear peptide of sequence SEQ ID NO:1, SEQ ID NO:2, SEQ ID NO:3, SEQ ID NO:4, SEQ ID NO:8, SEQ ID NO:9, SEQ ID NO:13, SEQ ID NO:14, SEQ ID NO:15, SEQ ID NO:18, or SEQ ID NO:19.

3. The method according to claim 1, wherein said pseudopeptide units are grafted directly on said support.

4. The method according to claim 1, wherein said pseudopeptide units are grafted on said support by means of a spacer.

5. The method according to claim 1, wherein k is between 5 and 6.

6. The method according to claim 1, wherein i equals 1 and Z is proline (P).

7. The method according to claim 1, wherein $Y_1$ is lysine (K) and $Y_2$ is arginine (R).

8. The method according to claim 1, wherein n and m are equal to 0.

9. The method according to claim 1, wherein the compound is selected from the following compounds:

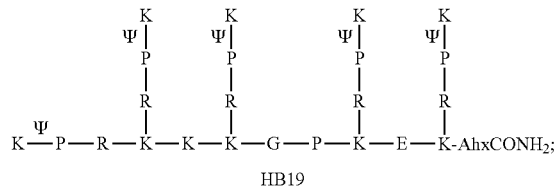
HB19

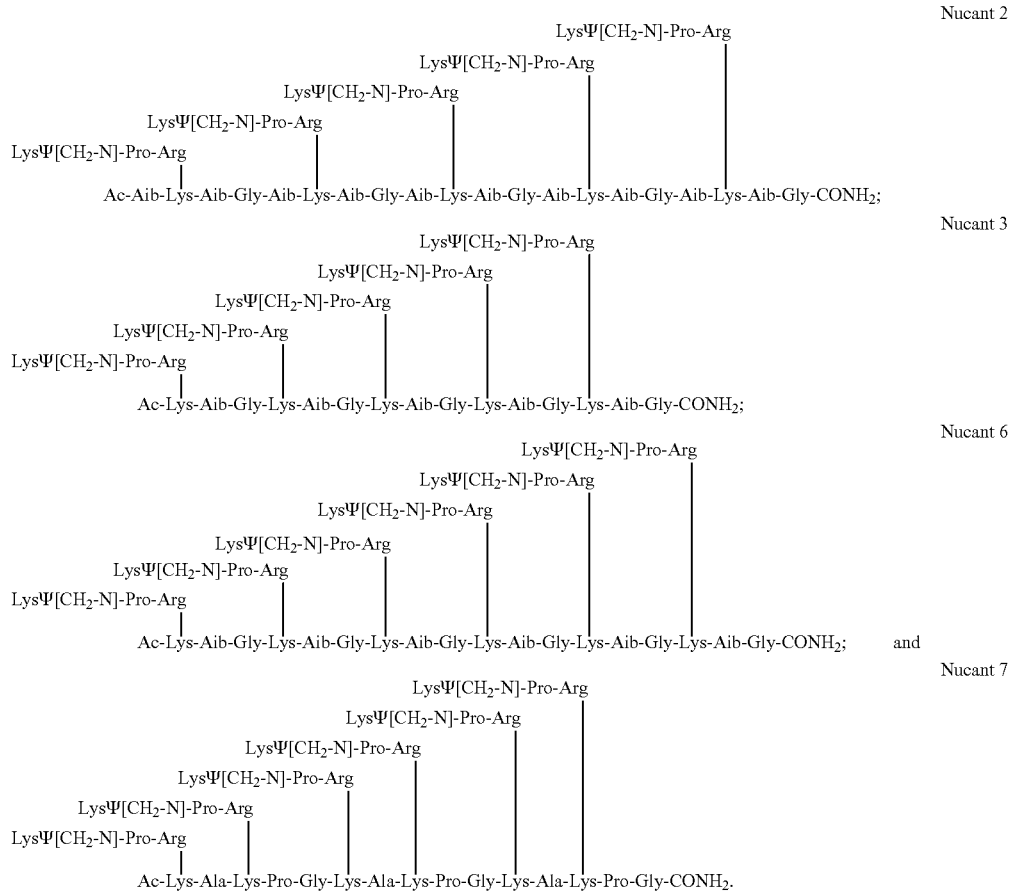

10. A method for treating cancer comprising the administration of an effective amount of a polyvalent synthetic compound comprising a support on which at least 3 pseudopeptide units are grafted, said compound being of formula (I):

$$[(X)_n - Y_1 \stackrel{\Psi}{-} (Z)_i - Y_2 - (X)_m]_k\text{-Support}, \quad (I)$$

wherein the support is a linear peptide including at least 3 lysine residues, each pseudopeptide unit being grafted to a lysine residue of the linear peptide support, and wherein grafted lysine residues are separated by at least one amino acid;

each X independently represents any amino acid;

$Y_1$ and $Y_2$ are selected independently from arginine (R) and lysine (K);

Z is proline;

n and i are independently 0 or 1;

m is an integer between 0 and 1;

k is an integer between 3 and 8; and $\Psi$ represents a modified peptide bond selected from the group consisting of a reduced bond (—CH$_2$NH—), a retro-inverso bond (—NHCO—), a methyleneoxy bond (—CH$_2$—O—), a thiomethylene bond (—CH$_2$—S—), a carba bond (—CH$_2$CH$_2$—), a ketomethylene bond (—CO—CH$_2$—), a hydroxyethylene bond (—CHOH—CH$_2$—), an E-alkene bond or a (—CH=CH—) bond, to a patient in need thereof.

11. A method for treating cancer comprising the administration of an effective amount of a polyvalent synthetic compound comprising a support on which at least 3 pseudopeptide units are grafted, said compound being of formula (I):

$$[(X)_n - Y_1 \stackrel{\Psi}{-} (Z)_i - Y_2 - (X)_m]_k\text{-Support}, \quad (I)$$

wherein the support is a linear peptide and each pseudopeptide unit is grafted to a lysine residue on said support, and wherein grafted lysine residues are separated by at least one amino acid;

each X independently represents any amino acid;

$Y_1$ and $Y_2$ are selected independently from arginine (R) and lysine (K);

Z is proline;

n and i are independently 0 or 1;

m is an integer between 0 and 1;

k is an integer between 3 and 8; and

Ψ represents a modified peptide bond selected from the group consisting of a reduced bond ($-CH_2NH-$), a retro-inverso bond ($-NHCO-$), a methyleneoxy bond ($-CH_2-O-$), a thiomethylene bond ($-CH_2-S-$), a carba bond ($-CH_2CH_2-$), a ketomethylene bond ($-CO-CH_2-$), a hydroxyethylene bond ($-CHOH-CH_2-$), an E-alkene bond or a ($-CH=CH-$) bond, to a patient in need thereof.

* * * * *

UNITED STATES PATENT AND TRADEMARK OFFICE
CERTIFICATE OF CORRECTION

PATENT NO.        : 8,497,349 B2  
APPLICATION NO.   : 12/298511  
DATED             : July 30, 2013  
INVENTOR(S)       : Jose Courty et al.

Page 1 of 1

It is certified that error appears in the above-identified patent and that said Letters Patent is hereby corrected as shown below:

Title Page

Item (22), PCT Filed: delete "Apr. 22, 2007" and insert --Apr. 27, 2007--

Signed and Sealed this  
Twenty-ninth Day of October, 2013

Teresa Stanek Rea  
*Deputy Director of the United States Patent and Trademark Office*

UNITED STATES PATENT AND TRADEMARK OFFICE
CERTIFICATE OF CORRECTION

PATENT NO. : 8,497,349 B2
APPLICATION NO. : 12/298511
DATED : July 30, 2013
INVENTOR(S) : Courty et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1217 days.

Signed and Sealed this
Fifteenth Day of September, 2015

Michelle K. Lee
*Director of the United States Patent and Trademark Office*